United States Patent [19]
Sharpless et al.

[11] Patent Number: 5,939,568
[45] Date of Patent: Aug. 17, 1999

[54] ACCELERATED CATALYSIS OF OLEFINIC EPOXIDATIONS

[75] Inventors: K. Barry Sharpless, La Jolla, Calif.; Joachim Rudolph, Krefeld, Germany

[73] Assignee: The Scripps Research Institute, La Jolla, Calif.

[21] Appl. No.: 08/842,732

[22] Filed: Apr. 16, 1997

Related U.S. Application Data

[60] Provisional application No. 60/036,804, Jan. 31, 1997.
[51] Int. Cl.$^6$ .................................................. C07D 303/00
[52] U.S. Cl. ............................................. 549/512
[58] Field of Search ............................................. 549/512

[56] References Cited

U.S. PATENT DOCUMENTS 5,618,958   4/1997   Tucker et al. .............................. 556/45

OTHER PUBLICATIONS

Herrmann et al, Angew. Chem., Int. Ed. Eng. (1991), 30, 1638–1641, 1991.

Herrmann et al, J. Mol. Catal., (1994), 86, 243–266, 1994.

*Primary Examiner*—Amelia Owens
*Attorney, Agent, or Firm*—Donald G. Lewis

[57] ABSTRACT

Rhenium-catalyzed epoxidation of olefinic substrates is accelerated by the use of acclerants having a nitrogenous aromatic heterocyclic structure. Use of the accelerants also enables the use of aqueous hydrogen peroxide as an oxidant. To achieve optimum acceleration, the accelerant should have a concentration within a range from 2.0 mole percent to 100 mole percent of the acclerant with respect to 1 mole of the olefinic substrate. Use of the accelerant also results in an increased yield with respect to the conversion of the olefinic substrate to epoxide product.

9 Claims, 16 Drawing Sheets

1) Non Cyclic Olefins

2) Endocyclic Olefins

3) Exocyclic Olefins

| entry | substrate | time (h) | conversion (%) | selectivity (%) |
|---|---|---|---|---|
| 1[c] | CH₂=CHCH₃ (propene) | 12 | 60 | 100 |
| 2[b] | 1-octene | 48 | 82 | 98 |
| 3[b] | styrene | 16 | 80 | 100 |
| 4[c] | α-methylstyrene | 4 | 97 | 99 |
| 5[b] | methylenecyclohexane | 3 | 99 | 100 |
| 6[c] | 1,1-diphenylethylene | 15 | 75 | 99 |

FIGURE 5

| entry | substrate | time (h) | conversion (%) | selectivity (%) |
|---|---|---|---|---|
| 7[b] | (trans-3-hexene) | 24 | 97 | 100 |
| 8[c] | (trans-β-methylstyrene) | 5 | 100 | 100 |
| 9[c] | (trans-stilbene) | 30 | 85 | 100 |
| 10[b] | (cis-3-hexene) | 6 | 99 | 99 |
| 11[c] | (cis-β-methylstyrene) | 4 | 100 | 100 |
| 12[c] | (cis-stilbene) | 30 | 99 | 100 |
| 13[c] | (indene) | 5 | 92 | 99 |
| 14[b] | (cyclohexene) | 6 | 96 | 100 |
| 15[b,c] | (1,2-dihydronaphthalene) | 4 | 100 | 100 |
| 16[c] | (6-cyano-2,2-dimethylchromene) | 30 | 60 | 99 |
| 17[c] | (norbornene) | 8 | 97 | 100 (only exo) |
| 18[b] | (cycloheptene) | 3 | 100 | 100 |
| 19[b] | (cyclooctene) | 2 | 100 | 100 |

FIGURE 6

| entry | substrate | time (h) | conversion (%) | selectivity (%) |
|---|---|---|---|---|
| 20[c] | (phenylcyclohexene) | 4 | 100 | 100 |
| 21[c] | (4-isopropylmethylcyclohexene) | 5 | 100 | 99 |
| 22[c] | (cholesteryl acetate) | 6 | 99 | 99[d] |
| 23[b] | (2-methyl-2-octene) | 2 | 100 | 100 |
| 24[c] | (isopropylidenecyclohexane) | 3 | 100 | 100 |

FIGURE 7

| entry | substrate | product | time (h) | conversion (%) | selectivity (%) | diastereomeric ratio |
|---|---|---|---|---|---|---|
| 25 | | | 8 | 91 | 99[b] | only anti |
| 26 | | | 6 | 100 | 100 | 96:4 (anti:syn) |
| 27 | | | 9 | 99 | 99[b] | only anti |
| 28 | | | 5 | 99 | 97 | only syn |
| 29 | | | 7 | 98 | 99 | only syn |
| 30 | | | 12 | 99 | 98 | 1:1 |
| 31 | | | 6 | 98 | 99 | 3:1 |
| 32 | | | 11 | 96 | 98 | 1:1 |
| 33 | | | 10 | 99 | 99 | 2.5:1 |

FIGURE 8

| Entry | Alkene | Conversion[b] | Yield[c] | Time |
|---|---|---|---|---|
| 1[d] | PhCH=CH2 (styrene) | 97% | 85% | 6 h |
| 2 | CH3(CH2)6CH=CH2 | >99% | 97% | 17 h |
| 3 | cyclohexyl-CH=CH2 | >99% | 86% | 30 h |
| 4 | neohexyl-type alkene (CH3CH2C(CH3)2CH=CH2) | 99% | 78% | 30 h |
| 5 | cyclohexyl-CH2-CH=CH2 | >99% | 89% | 20 h |
| 6 | HO-(CH2)8-CH=CH2 | >99% | 89% | 19 h |
| 7[e] | CH3(CH2)4CH(OH)CH=CH2 | >99% | 94% | 27 h |
| 8[e] | CH3(CH2)4CH(OH)CH2CH=CH2 | >99% | 88% | 17 h |
| 9[f] | HO-(CH2)2-CH=CH2 | >99% | 0% | 18 h |
| 10 | AcO-(CH2)2-CH=CH2 | >99% | 94% | 20 h |
| 11 | Cl-(CH2)8-CH=CH2 | >99% | 86% | 30 h |
| 12 | EtO2C-(CH2)8-CH=CH2 | >99% | 89% | 20 h |
| 13 | (Et)2N-C(O)-(CH2)8-CH=CH2 | >99% | 90% | 19 h |
| 14 | CH3CH2C(O)-(CH2)8-CH=CH2 | >99% | 96% | 24 h |

FIGURE 15

| Entry | Alkene | Conversion[b] | Yield[c] | Time |
|---|---|---|---|---|
| 1 | (but-2-enyl propyl alkene) | >99% | 89% | 8 h |
| 2 | (internal alkene) | >99% | 91% | 7 h |
| 3 | (tert-butyl propenyl) | >99% | 89% | 15 h |
| 4 | (diisopropyl alkene) | >99% | 85% | 8 h |
| 5[d,e] | Ph⁀⁀ | 94% | 84% | 2 h |
| 6[d,f] | Ph⁀⁀Ph | >99% | 92% | 17 h |
| 7 | ⁀⁀⁀OH | >99% | 80% | 6 h |
| 8[g] | ⁀⁀⁀OH | >99% | 78% | 3 h |
| 9[d] | Ph⁀⁀OH | >99% | 93% | 3 h |
| 10[d] | Ph⁀⁀OAc | >99% | 80% | 26 h |
| 11[g] | Ph⁀⁀C(O)OEt | 20% | 20% | 17 h |
| 12 | ⁀⁀⁀C(O)OEt | >99% | 86% | 25 h |

ACCELERATED CATALYSIS OF OLEFINIC EPOXIDATIONS

This application claims Provisional Application No. 60/036,804, filed Jan. 31, 1997.

GOVERNMENT RIGHTS

This invention was made with government support under Grant No. GM 28384 awarded by the National Institutes of Health and Grant No. CHE-9296055 awarded by the National Science Foundation. The U.S. government has certain rights in the invention.

TECHNICAL FIELD

The present invention relates to the epoxidation of olefins. More particularly, the present invention relates to the acceleration of organorhenium catalyzed olefinic epoxidations using nitrogenous aromatic heterocycles as accelerants, hydrogen peroxide as an oxidant, and water as a solvent.

BACKGROUND

Many catalyzed reactions may be accelerated by the use of ligands which bind to the catalyst and enhance its catalytic activity. Ligand acceleration of catalytic transformations is a desirable phenomenon since, in addition to increasing the rate of the reaction, the ligand may also influence the selectivity features of the reaction. (Berrisford et al. *Angew. Chem.* 1995, 107, 1159–1171; Berrisford et al. *Angew. Chem., Int. Ed. Engl.* 1995, 34, 1059–1070.)

Use of aqueous $H_2O_2$ as the oxidant in transition metal-catalyzed epoxidations was first described by Venturello et al. (Venturello et al. *J. Org. Chem.* 1983, 48, 3831–3833; Venturello et al. *J. Org. Chem.* 1988, 53, 1553–1557; Prandi et al. *Tetrahedron Lett.* 1986, 27, 2617–2620.) Venturello disclosed the use of a tungstate catalyst under phase transfer conditions. This method is unemployable for less reactive olefins. However, Noyori recently introduced a solvent-free variation which is more effective. (Sato et al. *J. Org. Chem.* 1996, 61, 8310–8311.) However, the scope of the Noyori variation is limited by epoxide opening-problems caused by the slight acidity of the reaction milieu. This is a recurring problem encountered by most epoxidation methods in use today.

An industrial metal-catalyzed epoxidation process which uses 30% aqueous $H_2O_2$ is disclosed by Romano et al. (*Chim. Ind.* (Milan) 1990, 72, 610–616; Clerici et al. *J. Catal.* 1993, 140, 71–83.) The method is based on the heterogeneous titanium-substituted silicalite catalyst (TS-1) developed by Enichem. The process is best employed with small, unbranched terminal olefins.

Commercial bulk production of alkyl-epoxides is achieved by oxidation of alkenes using t-butyl peroxide as an oxidant and $Mo^{+6}$ as a catalyst. Supplies and pricing of t-butyl peroxide are undependable because t-butyl peroxide is a by-product of another process. Furthermore, the range of substrates that can be oxidized by this procedure to form epoxides is highly limited.

Inorganic rhenium compounds such as $Re_2O_7$ or $ReO_3$ are known to exhibit modest catalytic activity for $H_2O_2$-based oxidations (Applied Homogeneous Catalysis with Organometallic Compounds, Cornils et al. (Eds.), VCH Weinheim, 1996). Herrmann et al. disclose that the catalysis of $H_2O_2$-based oxidations of olefins may be significantly enhanced by the use of alkylrhenium oxide as a catalyst. (Hoechst et al. DE 3.902.357 (1989); *Angew. Chem., Int. Ed. Engl.* 1991, 30, 1638–1641; Herrmann et. al. *J. Mol. Catal.* 1994, 86, 243–266; Adam et al. *Angew. Chem.* 1996, 108, 78–581; *Angew. Chem., Int. Ed.* 1996, 35, 533–535; Boelow et al. *Tetrahedron Lett.* 1996, 37, 2717–2720.) Herrmann discloses that organometallic oxorhenium(VII) species are powerful epoxidation catalysts with $H_2O_2$ as oxidant. Methyltrioxorhenium (MTO or $CH_3ReO_3$) is a particularly active catalyst. Methyltrioxorhenium (MTO) was first prepared by Beattie and Jones. (Beattie et al. *Inorg. Chem.* 1979, 18, 2318–2319.)

Herrmann discloses that epoxides produced by his alkylrhenium oxide catalyzed reaction are stabilized by basic ligand additives, e.g. pyridine. However, Herrmann also discloses that these same basic ligand additives have the undesirable property of inhibiting the alkylrhenium catalysis. The addition of either tertiary nitrogen bases or pyridine (basic ligand additives) was found to suppress epoxide ring opening processes. Moreover, the stabilizing effects of these additives is characterized as occurs at the expense of a strong detrimental effect on catalyst activity. In balance, Herrmann does not recommend the use of basic ligand additives in connection with his alkylrhenium oxide catalyzed epoxidation process.

Herrmann also discloses that his alkylrhenium oxide catalyzed olefinic epoxidation reaction should be performed under anhydrous conditions. Hermann's work focuses on the use of anhydrous $H_2O_2$ (particularly in t-BuOH) because water was detrimental, presumably due to hydrolytic epoxide ring opening. Such "anhydrous" $H_2O_2$ solutions would probably be unsuitable for large scale applications. A more serious limitation of their process is the strong tendency for the epoxide product to be destroyed through ring opening reactions. Furthermore, the prior art teaches that an excess of olefin is needed to drive epoxidation reactions. These problems have not been overcome by Herrmann or others. (Pestovsky et al. *J. Chem. Soc.*, Dalton Trans. 2 1995, 133–137; Al-Ajlouni et al. *J. Org. Chem.* 1996, 61, 3969–3976; ARCO Chemical Technology US 5.166.372 (1992)).

Tucker et al. (U.S. Pat. No. 5,618,958) disclose the use of alkylrhenium oxide catalysts with chiral ligands, including imine ligands, for catalyzing asymmetric epoxidations of olefins using pressurized oxygen and organic solvents. However, Tucker does not disclose the use of nitrogenous aromatic heterocycles as accelerants in connection with organorhenium oxide catalyzed epoxidations of olefin. Furthermore, Tucker does not disclose the use of aqueous solvents or of hydrogen peroxide as an oxidant.

What is needed is a process which overcomes the limitations of the rhenium oxide catalyzed epoxidation which are undesired hydrolytic epoxide ring opening, the requirement of excess olefinic substrate, the requirement of anhydrous conditions, the use of specific olefinic substrates, low yields, and the inhibition of the rhenium oxide catalyst by the basic ligand additives.

Furthermore, an accelerated epoxidation process is needed which employs commercially available accelerants, commercial grade hydrogen peroxide as an oxidant and a commercially available organorhenium oxide as a catalyst in mild aqueous solvent conditions and at ambient temperatures.

SUMMARY OF THE INVENTION

The invention is directed to an improved method for catalyzing olefinic epoxidations. The olefinic epoxidations are of a type which employ organorhenium oxide as a catalyst and hydrogen peroxide as an oxidant. The improvement is directed to the use of accelerants for accelerating the rate of the epoxidation reaction and increasing the overall yield. More particularly, the accelerants are nitrogenous aromatic heterocycles and are employed at concentrations above 2.0 mole percent with respect to the olefin substrate. In a preferred mode, the accelerants are employed in conjunction with the use of non-coordinating polar solvents and of aqueous hydrogen peroxide.

The mechanism whereby the nitrogenous aromatic heterocycles accelerate the organorhenium oxide catalyzed olefinic epoxidations is not fully understood. However, several factors may synergistically contribute to the acceleration effect. Firstly, the nitrogenous aromatic heterocyclic accelerants may act as ligands which bind to and accelerate the organorhenium oxide catalyst. This phenomenon is known as ligand accelerated catalysis (LAC). Secondly, nitrogenous aromatic heterocyclic accelerants may act as buffers which neutralize acidic by-products which can destablize the epoxide products and reduce the yield. Thirdly, the nitrogenous aromatic heterocyclic accelerants may enhance the solubility of the olefinic substrates and reactants.

Catalysis of olefinic epoxidations by organorhenium oxides is significantly accelerated by the presence of elevated concentrations of accelerants having a nitrogenous aromatic heterocyclic structure. As discussed above, Herrmann discloses that, at low concentrations of ligand, the ligand inhibits the organorhenium oxide catalysis of the olefinic epoxidation. In particular, at a catalyst to ligand ratio of 1:1, no ligand accelerated effect is observed. Additionally, we verify herein that tertiary amines inhibit the organorhenium oxide catalysis, independent of the amount used.

An alternative aspect of the invention is directed to olefinic epoxidations using organorhenium oxide as a catalyst, nitrogenous aromatic heterocycles as an accelerant, and aqueous (water containing) solvent systems.

A further alternative aspect of the invention is directed to olefinic epoxidations using organorhenium oxide as a catalyst and nitrogenous aromatic heterocycles as an accelerant wherein no excess of olefinic substrate is needed to drive the epoxidation reaction. The elimination of the need for excess olefinic substrate is an unexpected consequence of two synergetic activities of the nitrogenous aromatic heterocyclic accelerants, viz.:

a. The stabilization of the epoxide product and reaction intermediate by the accelerant; and b. The acceleration of the epoxidation reaction.

A further alternative aspect of the invention is directed to olefinic epoxidations using organorhenium oxide as a catalyst and nitrogenous aromatic heterocycles as an accelerant wherein the oxidant is an aqueous hydrogen peroxide having a concentration within a range of 10 to 85% or more preferably a concentration of 30% accelerant may be employed.

A) an epoxidation of the exocyclic olefin, α-methylstyrene, using MTO as a catalyst and pyridine as an accelerant on a 100 mM scale; and B) an epoxidation of the endocyclic olefin, 1-phenylcyclohexene, using MTO as a catalyst and pyridine as an accelerant on a 50 mM scale.

Figure 2:
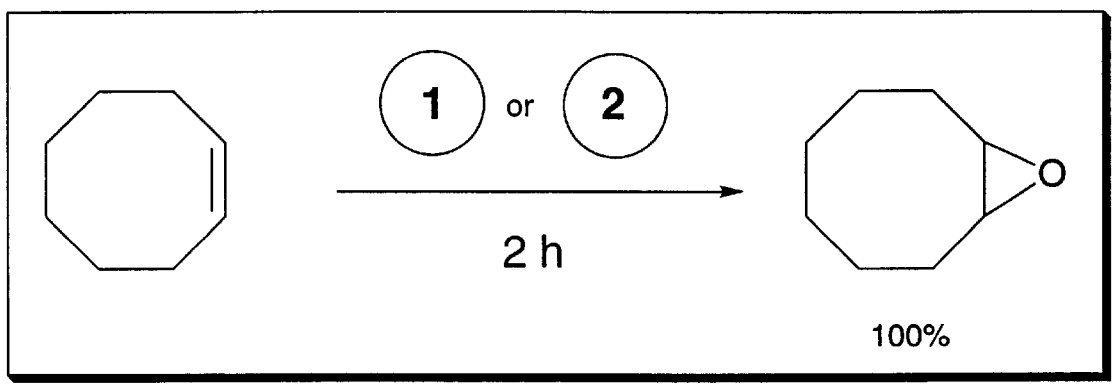

FIG. 2 illustrates a $CH_3ReO_3$-catalyzed epoxidation on cyclooctene comparing the prior art conditions with the conditions of the present invention:

Condition (1): (Present invention): ranges: $CH_3ReO_3$ (MTO) (0.1 to 1.0 mol %), pyridine or pyridine based ligand (2–100%), 1 to 2.5 equivalent aqueous 10 to 85% $H_2O_2$, to [0.0025] Molar solvent selected from the group consisting of $CH_3NO_2$, methylene chloride, chloroform, carbon tetrachloride, see synthetic protocols for complete list.

Condition (2): (Prior art: Herrmann): $CH_3ReO_3$ (0.5%), 1.5 equivalents anhydrous $H_2O_2$, t-BuOH.

Figure 3:
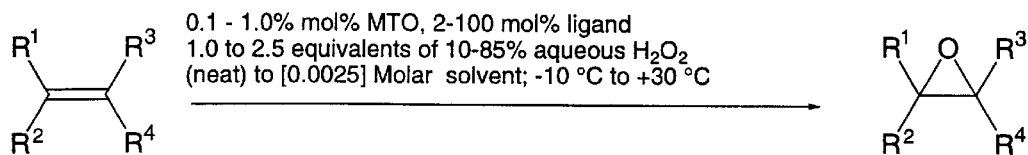
Figure 3:
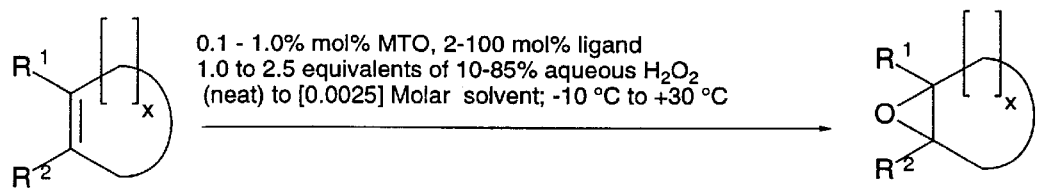
Figure 3:
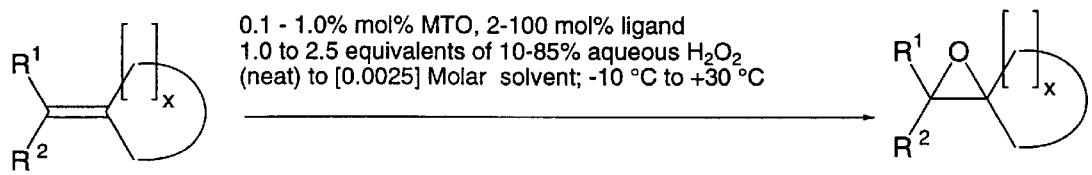

FIG. 3 illustrates the various substrate olefins which are compatible with organorhenium catalyzed epoxidations using the nitrogenous aromatic heterocyclic accelerants disclosed herein using the indicated rage of conditions. A representative but nonexhaustive example of substitutions on the indicated olefin are included as follows, wherein $R_1$, $R_2$, $R_3$ and $R_4$ of said olefin, FIG. 3, equations 1–3, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, Br, OH, and $C_1$-$C_6$ alkyl containing the following substitutions: F, Cl, Br, CN, OH, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, OR, NRR', etc. The variable "x" represents a range of rings including $C_4H_4$ to $C_8H_{16}$ (cyclobutane to cyclodecene-derivatives [cis and trans]), etc.

Figure 4:
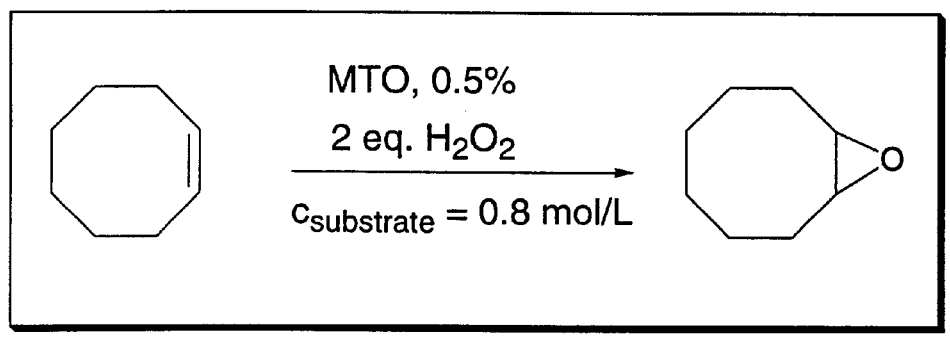
Figure 4:
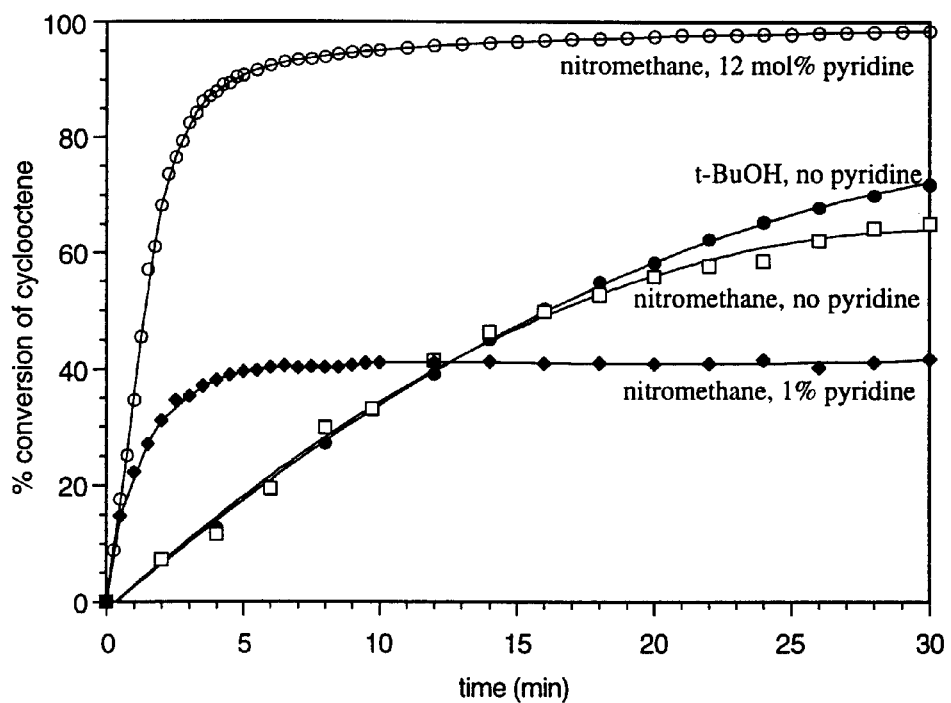

FIG. 4 illustrates a reaction profile of the MTO-catalyzed epoxidation of cyclooctene in different solvents with different amounts of pyridine added (0.5 mol % MTO, 2 equivalents 30% $H_2O_2$, $c_{substrate}$=0.8 mol/L); analysis via GC after quenching the aliquots with $MnO_2$.).

FIG. 5 shows a table of exemplary terminal olefins which show good to excellent conversion to epoxide using the MTO-pyridine catalyzed epoxidation process with aqueous hydrogen peroxide wherein [a] represents reaction conditions: $c_{substrate}$=1.5 mol/L; 0.5% MTO, 12% pyridine, 1.5 equivalents 30% aqueous $H_2O_2$, $CH_2Cl_2$, 10° C. to room temperature; [b] Conversion and selectivity determined via GC; [c] Conversion and selectivity determined via $^1$H-NMR (400 MHZ).

FIG. 6 shows a table of exemplary reactions of the MTO/pyridine-catalyzed epoxidation process using 1,2-disubstituted olefins wherein [a] represents reaction conditions: $c_{substrate}$=1.5 mol/L; 0.5% MTO, 12% pyridine, 1.5 equivalents 30% aqueous $H_2O_2$, $CH_2Cl_2$, 10° C. to room temperature; [b] Conversion and selectivity determined via GC; [c] Conversion and selectivity determined via $^1$H-NMR (400 MHZ).

FIG. 7 shows a table of exemplary reactions of the MTO/pyridine-catalyzed epoxidation process using tri- and tetra substituted olefins wherein [a] represents reaction conditions: $c_{substrate}$=1.5 mol/L; 0.5% MTO, 12% pyridine, 1.5 equivalents 30% aqueous $H_2O_2$, $CH_2Cl_2$, 10° C. to room temperature; [b] Conversion and selectivity determined via GC; [c] Conversion and selectivity determined via $^1$H-NMR (400 MHZ); [d] Ratio of diastereoisomers: 1:1.

FIG. 8 shows a table of exemplary reactions of the MTO/py-catalyzed epoxidation using various dienes wherein [a] represents reaction conditions: $c_{substrate}$=1.5 mol/L; 0.5% MTO, 12% pyridine, 2.5 equivalents 50% aqueous $H_2O_2$, $CH_2Cl_2$, 10° C. to room temperature; conversions and selectivities have been determined via $^1$H-NMR (400 MHZ); [b] In these cases monoepoxide can be found too. Selectivity refers to overall epoxide formation.

Figure 9:
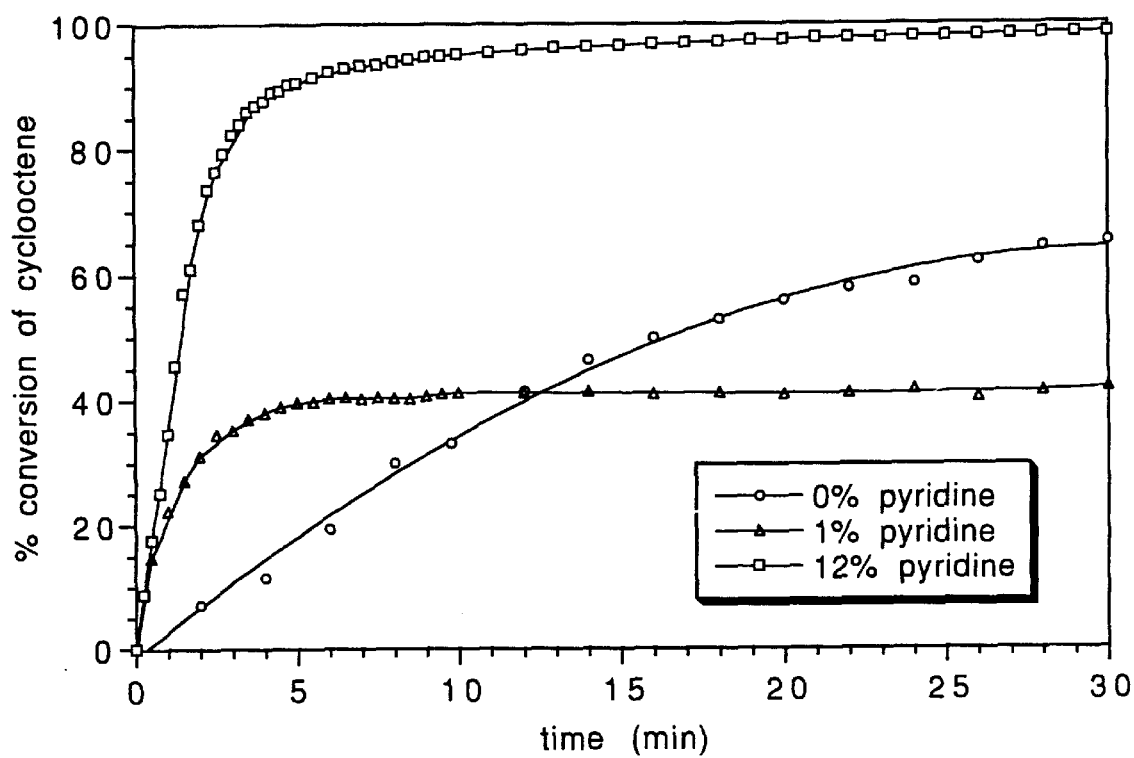

FIG. 9 shows a reaction profile of MTO/pyridine catalyzed epoxidation of cyclooctene using 2.0 equivalents 30% hydrogen peroxide in nitromethane wherein pyridine, 2 equivalents 30% $H_2O_2$ in nitromethane (two phase system): with 1 or 12 mol % pyridine added a clear-cut reaction acceleration with respect to the ligand free reaction can be observed (~15 fold). With 1% added however, the catalyst is decomposed quickly, whereas with 12 mol % pyridine added the catalyst lifetime is fully preserved to ensure reaction completion.

Figure 10:
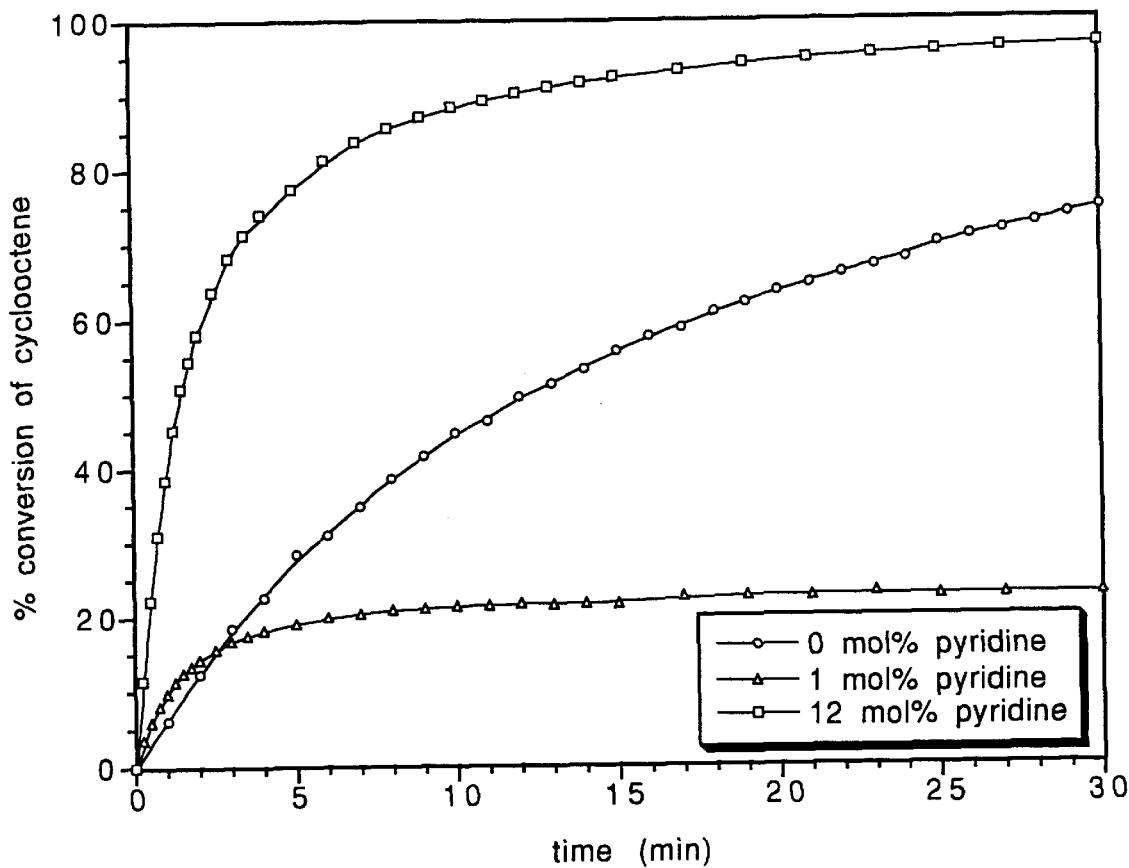

FIG. 10 shows a reaction profile of MTO/pyridine catalyzed epoxidation of cyclooctene using 1.3 equivalents 50% $H_2O_2$ in $CH_3NO_2$/t-BuOH (85:15 v/v) (homogeneous system): the analogous effects can be observed in this homogeneous system. The effects are probably less pronounced than in FIG. 9 because t-BuOH might serve as a competing ligand (compare with FIG. 11). The idea of this experiment was to show that the main role of pyridine is not the function as a phase transfer reagent.

Figure 11:
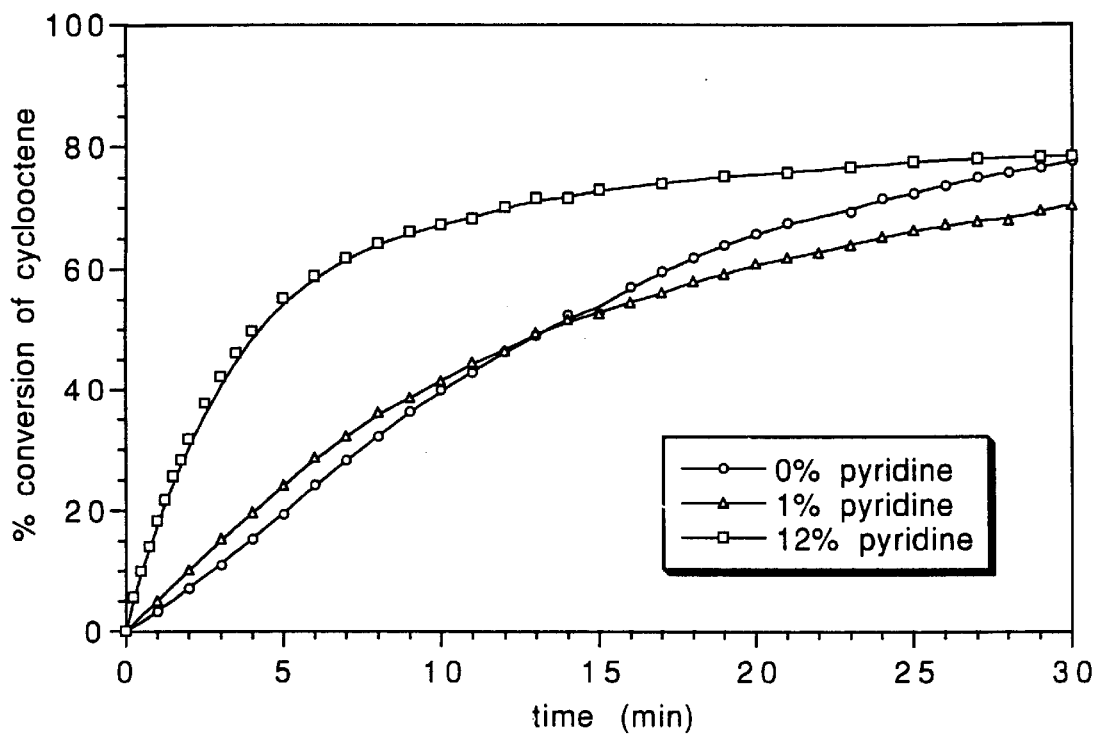

FIG. 11 shows a reaction profile of MTO/pyridine catalyzed epoxidation of cyclooctene using 2.0 equivalents 30% $H_2O_2$ in t-BuOH wherein pyridine, 2 equivalents 30% $H_2O_2$ in t-BuOH (homogeneous system): t-BuOH has been used as solvent in MTO-catalyzed oxidation reactions by Herrmann et others. The reaction profile shows that the pyridine (when using 12 mol %) still mediates a striking acceleration effect. When using 1 mol % almost no difference to the ligand-free condition can be seen, probably due to a competition of t-BuOH as ligand. t-BuOH is considerably less suitable for the acceleration effect to take place.

Figure 12:
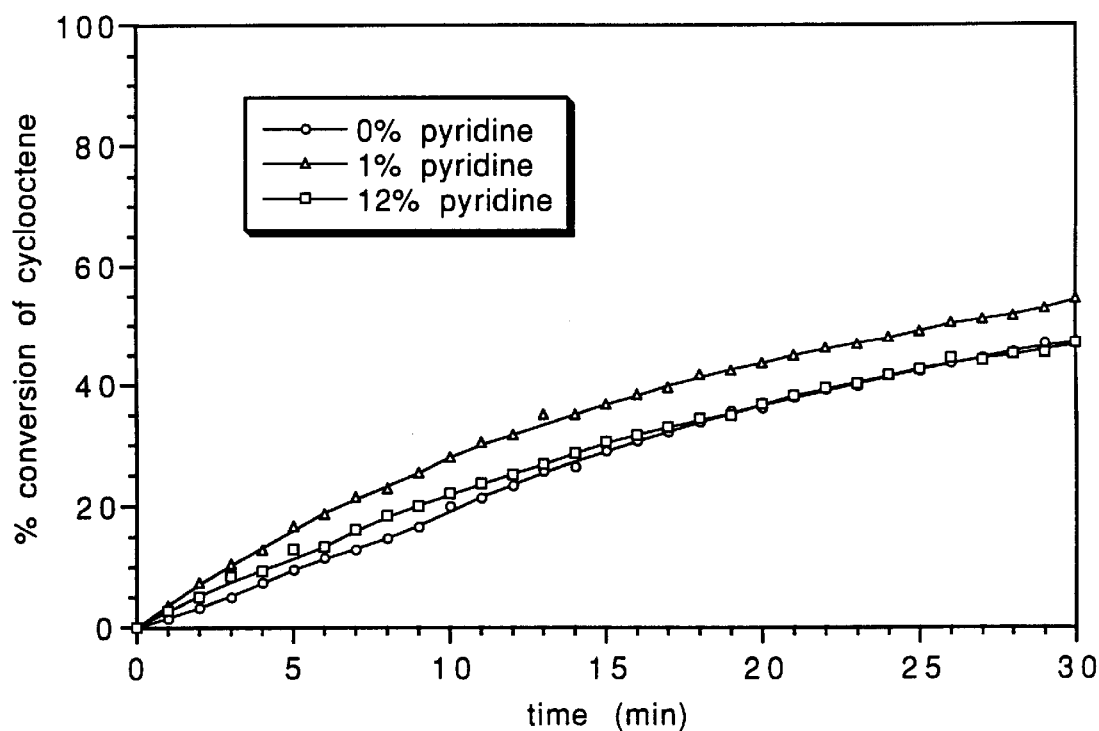

FIG. 12 shows a reaction profile of MTO/pyridine catalyzed epoxidation of cyclooctene using 2.0 equivalents anhydrous $H_2O_2$ in t-butanol wherein pyridine, 2 equivalents "anhydrous" $H_2O_2$ in t-BuOH (homogeneous system): t-When using "anhydrous" $H_2O_2$ no remarkable ligand effect can be observed. The reactions with and without ligand proceed quite similar. They are very slow and catalyst decomposition cannot be observed.

Figure 13:
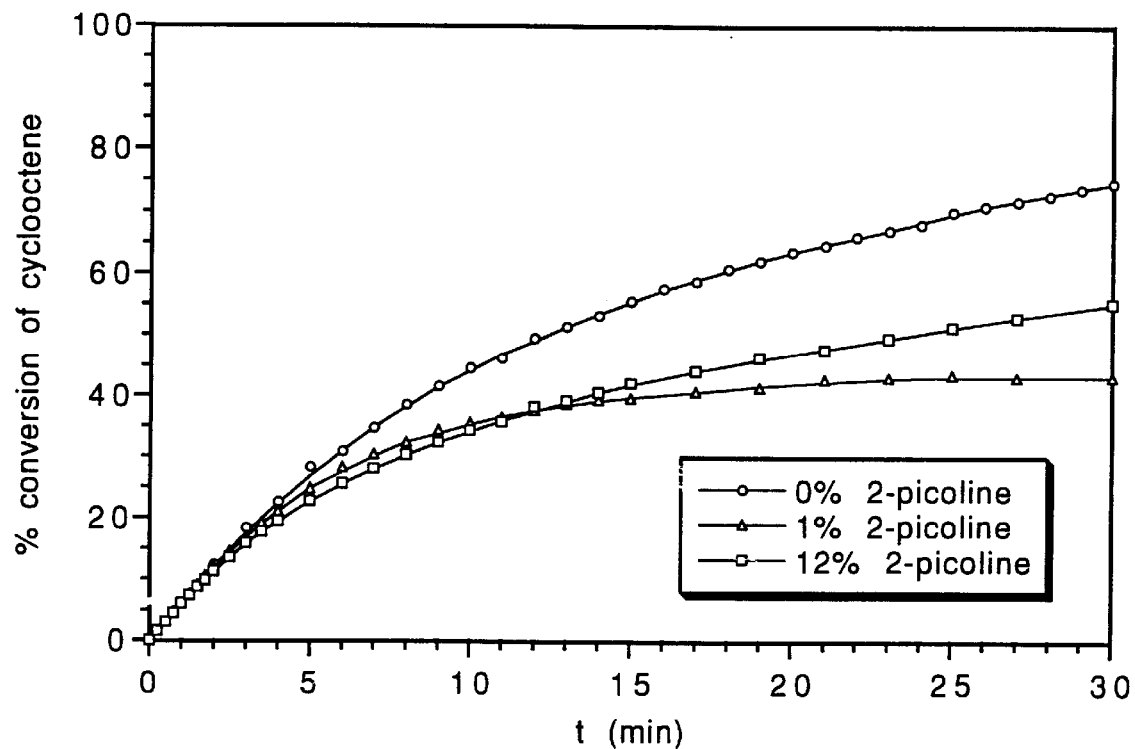

FIG. 13 shows a reaction profile of MTO/pyridine catalyzed epoxidation of cyclooctene using 1.3 equivalents 50% $H_2O_2$ in nitromethane/t-butanol 85:15 v/v (homogeneous conditions) wherein 2-picoline, 1.3 equivalents 50% $H_2O_2$ in $CH_3NO_2$/t-BuOH (85:15 v/v) (homogeneous system): 2-picoline is sterically very different from pyridine and less likely to coordinate. This is an example wherein the rate enhancement is substantially reduced using sterically hindered ligands. Unlike in the case of pyridine absolutely no initial rate enhancement can be seen here. The hypothesis of ligand acceleration thus got a stronger evidence: the basicity of pyridine (pKs=5.25) and 2-picoline (pKs=5.97) is relatively similar and, as the system is homogeneous no phase partition equilibria have to be considered: steric effects leading to different coordination behavior are likely to be the reason for the different rates.

Figure 14:
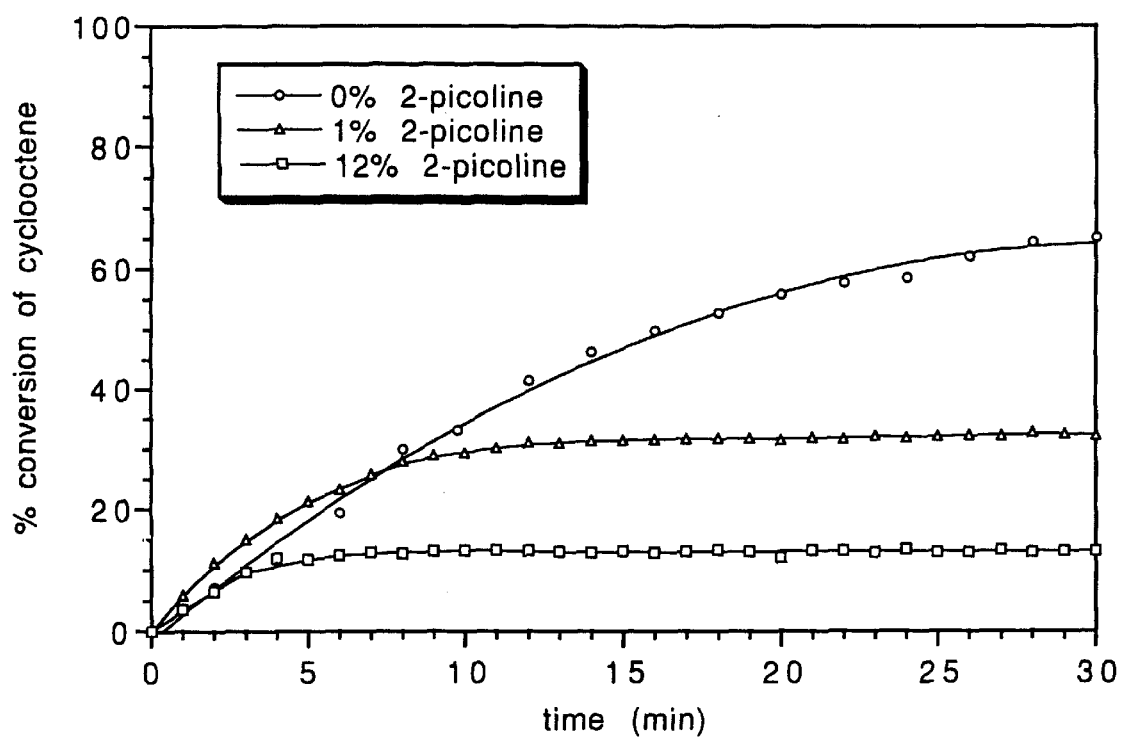

FIG. 14 shows a reaction profile of MTO/pyridine catalyzed epoxidation of cyclooctene using 2.0 equivalents 30% $H_2O_2$ and different amounts 2-picoline in nitromethane (two phase) wherein 2-picoline, 3 equivalents 30% $H_2O_2$ in $CH_3NO_2$ (2-phase-conditions): the reaction profiles under these solvent conditions are quite similar to those as shown in FIG. 13, however catalyst decomposition when using ligand occurs very early. Note that the use of 12% ligand is even worse than the use of 1% ligand underlining again the completely different behavior of 2-picoline than pyridine in MTO catalysis.

FIG. 15 shows a table of exemplary reactions of the MTO/3-cyanopyridine-catalyzed epoxidation process on terminal olefins wherein a) reaction conditions: Alkene (1 eq), MTO (0.5 mol %), 3-cyanopyridine (10 mol %), 30% $H_2O_2$ (aq) (2 eq) in dichloromethane. Alkene concentration: 1.3 M. b) Determined by GLC analysis with respect to internal standard; c) Isolated yield; d) A mixture of 3-cyanopyridine and pyridine (10 mol % of each) was employed. Alkene concentration: 4 M. e) The epoxides were formed in a 1:1 diastereomeric mixture. f) The formed tetrahydrofurfuryl alcohol was isolated in 97%.

FIG. 16 shows a table of exemplary reactions of the MTO/3-cyanopyridine-catalyzed epoxidation process on trans alkenes wherein [a] represents reaction conditions: Alkene (1 eq), MTO (0.5 mol %), 3-cyanopyridine (10 mol %), 30% $H_2O_2$ (aq) (2 eq) in dichloromethane. Alkene concentration: 1.3 M. b) Determined by GLC analysis with respect to internal standard. c) GLC yield given with respect to internal standard, response factors not determined. d) A mixture of 3-cyanopyridine (10 mol %) and pyridine (5 mol %) was used. e) No sample taken after 2 hours. f) Isolated yield. g) MTO (0.25 mol %) 3-cyanopyridine (5%). g) Same conversion after 30 hours.

DETAILED DESCRIPTION OF THE INVENTION

The invention is directed to the use of accelerants having a nitrogenous aromatic heterocyclic structure in connection with a process for methyltrioxorhenium (MTO)-catalyzed olefin epoxidations. A key concept of the invention is that, above a certain accelerant concentration (2.0 mol percent accelerant with respect to the olefin substrate), the accelerant, especially pyridine and the like, enhances the activity of alkyl rhenium catalysts including $CH_3ReO_3$ (MTO) in the epoxidation of alkenes. This effect is very solvent-dependent and up until now, has not been recognized. The result is full conversion of a range of substrates within a short period of time. Kinetic experiments underline these facts and clearly indicate that the phenomenon of ligand accelerated catalysis (LAC) contributes to the overall activity of the accelerants.

Non-coordinating polar solvents show the most advantageous effect. Among these solvents dichloromethane and nitromethane have been found to give by far the best results. The use of these two solvents has never been described in connection with MTO-catalysis.

Besides its significant activation effect the accelerant also suppresses epoxide opening (leading to 1,2-diols) completely. Even with very sensitive epoxides, ring opening is not observed. With few exceptions the existing catalytic and stoichiometric epoxidation reagents are most reactive in acidic environments, which very often mediate the decomposition of the epoxide products.

The invented process does not need anhydrous conditions. Commercially available aqueous 30% $H_2O_2$ (the process works in a range from 10%–85%) can be used rendering this system highly practical. This is in contrast to the prior art which uses anhydrous systems. The catalyst can be used in a range from 0.1–1.0 mol % with respect to the substrate and the accelerant can be used in a range from 2–100 mole percent with respect to the substrate.

The observation of such an LAC-phenomenon opens up the possibility of enantioselective catalytic epoxidation by using suitable chiral nitrogenous aromatic heterocyclic accelerants.

We report herein that a range of saturated nonaromatic tertiary amines strongly inhibit catalyst activity. This effect is independent of the solvent, the amount of amine, and the presence or absence of water. However, unlike Herrmann and Adam, we found that pyridine, and pyridine derivatives in sufficient amounts exhibited a remarkable acceleration effect on the epoxidation rate.

In a preferred embodiment of the invention, aqueous $H_2O_2$ is the oxidant and the accelerant is pyridine or a pyridine based derivative at elevated concentrations (above 2.0 mole % or greater overall concentration) in specific solvent systems such as nitromethane or methylene chloride. The acceleration effect of pyridines is most pronounced in aprotic and noncoordinating solvents (such as $CH_2Cl_2$ and $CH_3NO_2$). In addition to its beneficial effect on rate, the pyridine accelerant shuts down the acid-catalyzed ring opening reactions which can be detrimental to epoxide yield and purity. This accelerant-modified process also affords excellent space-time yields as a consequence of both the rate enhancement and the optimal reaction concentration (circa 1–2 molar in olefin). The standard procedure is exemplified in FIG. 1 (equation B) for 1-phenyl-cyclohexene whose epoxide is sensitive to acid-catalyzed destruction, and is difficult to prepare by most existing epoxidation methods (Berti et al. *Tetrahedron* 1965, 21, 3277–3283).

While the reaction profile for the epoxidation of cyclooctene (FIG. 4) clearly shows the rate enhancing effect of the pyridine accelerant, it also reveals that catalyst lifetime is critically dependent on the amount of pyridine present. The initial rates using either 1 mol % or 12 mol % pyridine in $CH_3NO_2$ (or $CH_2Cl_2$, not shown) as solvent are nearly the same but in the former case the catalyst decomposes completely within about 5 minutes, resulting in poor conversion. With $CH_3NO_2$ or $CH_2Cl_2$ as solvent and about 3 or more mol % pyridine present, the catalyst is preserved and cyclooctene is more than 95% converted to the epoxide within 15 minutes (Results show that the amount of water present (delivered with $H_2O_2$ and/or generated in the course of the reaction) has a major influence on catalyst activity, both turnover rate and lifetime).

Pyridine and pyridine base accelerants play three crucial roles in enhancing this process: 1) it speeds catalytic turnover, 2) it prevents decomposition of epoxide products, and 3) in sufficient concentration, it increases catalyst lifetime. The fact that pyridine actually accelerates catalyst decomposition until a threshold concentration is reached, probably explains why earlier workers did not see its dramatic beneficial effects. Furthermore, we find that with t-butanol as the solvent the enhancing effects of pyridine are only evident at much higher pyridine concentrations.

The wide scope of this process is revealed in FIGS. 5–8 and 15–16. Due to practical considerations, we used $CH_2Cl_2$ as solvent for all examples even though $CH_3NO_2$ is slightly superior with regard to reaction rate. Standard experimental procedure (exemplified for the epoxidation of 1-phenyl-cyclohexene) is as follows: In a 50 mL flask equipped with a magnetic stirrer, 7.9 g (50 mmol) of 1-phenylcyclohexene and 63 mg (0.25 mmol, 0.5 mol %) of MTO are dissolved in 25 mL $CH_2Cl_2$. To this solution is added 0.48 mL (6 mmol, 12 mol %) of pyridine followed by 7.6 mL (75 mmol; 1.5 equivalents) of 30% aqueous $H_2O_2$ added dropwise from a syringe (circa 5–10 minutes). During the $H_2O_2$-addition the temperature is kept at 20–25° C. by applying an external cooling bath. The reaction is complete after 6 h and the aqueous phase is separated and discarded. The remaining $H_2O_2$ in the yellow organic phase is decomposed to $O_2$ and $H_2O$ by stirring with a catalytic amount of $MnO_2$ (circa 5 mg). After the yellow color has completely disappeared the mixture is dried over $Na_2SO_4$, concentrated, and purified by filtration through a short column of silica gel which has been deactivated with $NEt_3$. The column is washed with hexane/$CH_2Cl_2$ and concentration of the eluate affords 7.9 g (91%) of 1-phenyl-1,2-epoxycyclohexane as a colorless oil).

Even epoxides which are very sensitive to ring opening, such as the products from α-methylstyrene, indene, and 1-phenylcyclohexene (FIGS. 5 and 6, entries 3, 11, and 17) do not undergo hydrolytic ring opening (Such substrates yield only products derived from acid-catalyzed epoxide opening under the ligand-free conditions of the original MTO-catalyzed procedure even though anhydrous $H_2O_2$ is the oxidant). A further useful feature of the reaction is that it can be easily scaled up, as demonstrated for a number of the olefins in Table 1 on a 50 millimole scale.

Epoxidation of selected cyclic dienes provides high diastereoselectivities for the cases studied (FIG. 8) (Diastereoselective MTO-catalyzed epoxidations of allylic alcohols and other chiral olefins using the $H_2O_2$-urea-complex as oxidant, have already been reported by Adam et al. *Angew. Chem.* 1996, 108, 78–581; *Angew. Chem., Int. Ed.* 1996, 35, 533–535 and Boelow et al. *Tetrahedron Lett.* 1996, 37, 2717–2720. Compare to the peracid mediated bis-epoxidation of 1,4-cyclohexadiene and 1,5-cyclooctadiene, respectively: Craig et al. *J. Org. Chem.* 1967, 32, 3743–3749; Cope et al. *J. Org. Chem.* 1969, 34, 2231–2234). Note that 50% $H_2O_2$ was used in these experiments to increase reactivity by reducing the overall water content. Even so, epoxidation of the two 1,3-dienes (entries 1 and 3) was incomplete.

There are multiple advantages of this new epoxidation method over the m-chloroperbenzoic acid (m-CPBA) method, the latter being the one in widest use for research scale epoxidations at present: 1) the MTO/pyridine process is more economical as well as safer than the m-CPBA process; 2) both selectivity and scope are much greater, due largely to the fact that the epoxide products, even in the most acid sensitive cases (e.g. entries 3, 11 and 17, FIGS. 5 and 6), do not suffer ring opening or rearrangement reactions; 3) the new system is more reactive, can be run with significantly less solvent, and workup/product isolation is substantially easier; finally, 4) the only by-product is water. The buffered m-CPBA procedures partly overcome the "acidity problem" but not as efficiently as this new MTO/pyridine system. See for example: Camps et al. *J. Org. Chem.* 1982, 47, 5402–5404; Imuta et al. *J. Org. Chem.* 1979, 44, 1351–1352; Anderson et al. *J. Org. Chem.* 1973, 38, 2267–2268. Only the Payne epoxidation process (vida infra) and the Murray DMDO reagent (vida infra) are of comparable effectiveness. Payne et al. *Tetrahedron* 1962, 18, 763–765. For a variety of reasons, the Payne epoxidation is often the method of choice for industrial batch-type applications, but on a small scale the need for continuous pH-control is inconvenient. Murray et al. *Org. Syntheses* 1996, 74, 91–100.

The use of nitrogenous aromatic accelerants for accelerating the rhenium-catalyzed epoxidation process appears to be the first example of rate enhancement by a basic ligand of an oxidative transformation involving peroxometal species. The mechanistic basis for this pyridine effect deserves careful study but could take years to work out. However, the importance of decoupling epoxidation activity from acidity will be immediately apparent to all synthetic chemists. An accelerating effect for teriary amine ligands in catalytic epoxidations is well documented for systems involving $d^2$, $d^3$, and $d^4$ oxo-metal species: see reviews in Meunier et al. *Bull. Soc. Chim. Fr.* 1986, 578–594; McMurry et al. In *Cytochrome P-450: structure, mechanism, and biochemistry*; Ortiz de Montellano, P. R. (Ed.); Plenum Press: New York, 1986, p. 1–28. With few exceptions (e.g. Payne and Murray reagents), the existing catalytic and stoichiometric epoxidation systems are most reactive under acidic conditions and of course the latter often cause destruction of the epoxide product.

The search for a simple, catalytic epoxidation process which functions optimally under neutral-to-basic conditions has been a constant, albeit elusive, goal of ours for the past 25 years. Having found such a system, wherein the Rappé-Goddard-"spectator oxo" concept has been a key guiding principle ever since it was first published in 1980: Rappé et al. Nature 1980, 285, 311–312; Rappé et al. J. Am. Chem. Soc. 1982, 104, 448–456; Rappé et al. Goddard III et al. J. Am. Chem. Soc. 1982, 104, 3287–3294, we are of course interested in understanding and exploiting the new reactivity features it offers.

A representative example of the process is as follows: In a standard reaction vessel, the olefin substrate (1.0 equivalent; applicable olefins are listed vida infra) is dissolved in the solvent (the process works in concentrations ranging from 0.0025 Molar to Neat (preferred embodiment at 1.5 Molar); applicable solvents are listed vida infra) and the organorhenium oxide is added (the process works in catalytic amounts ranging from 0.10 mole percent to 1.0 mole percent of the organo rheniumoxide with respect to the olefin substrate (preferred embodiment 0.5 mole percent); applicable organorhenium oxides are listed vida infra).

To this solution is added the accelerant wherein the process works in amounts ranging from 2.0 mole percent to mole 100 mole percent of the accelerant with respect to the olefin substrate (preferred embodiment 12.0 mole percent accelerant); applicable accelerants are listed vida infra. The process works optimally in a range from −10° C. to +30° C. wherein the temperature is stabilized by using a cooling bath (note that the process can be carried out at room temperature). External cooling with cold water is generally recommended, especially in large scale applications. Applying temperatures of approximately 5–10° C. in the initial state of the reaction gives, in some cases better results (the lifetime of catalyst might be enhanced). Applying temperatures in the range of 50° C. and higher diminishes the catalyst activity dramatically.

To this solution is added dropwise hydrogen peroxide wherein the process works in amounts ranging from 1.0 equivalents to 3.0 equivalents of commercially available 30% hydrogen peroxide with respect to the olefin substrate (alternative concentrations from 10% to 85% hydrogen peroxide in amounts ranging from 1.0 equivalents to 3.0 equivalents are also reasonable; preferred embodiment 1.5 equivalents of 30% hydrogen peroxide for monoenes). The color of the solution turns yellow which indicates the formation of a catalytic active ligand-rhenium-peroxo species. When the yellow color has disappeared no further conversion is observed. In addition, the order of addition does not seem to play a role, except that $H_2O_2$ has to be added at last.

Accelerants

The preferred embodiment uses 12.0 mole percent pyridine accelerant with respect to the olefin substrate, although the process observes the acceleration effect in a range from 2.0 mole percent to 100 mol percent accelerant with respect to the olefin substrate. Nitrogenous aromatic heterocycles, especially pyridine based accelerants, work exceptionally well in the acceleration of epoxidation of olefins and increase yields by reducing side products.

Accelerants which improve the process by acceleration and reduction of side products comprise the following compounds which are commercially available from Aldrich, Sigma, Fluka or other chemical sources: pyridine, 3-cyanopyridine, 2-cyanopyridine, cotinine, 2-picoline, 2-ethylpyridine, 2-propylpyridine, 2-phenylpyridine, 2-(p-tolyl)pyridine, 2-benzylpyridine, 2-acetylpyridine, 2-benzoylpyridine, 2-fluoropyridine, 2-chloropyridine, 2-bromopyridine, 2-hydroxypyridine, 2-pyridylcarbinol, 2-pyridineethanol, 2-pyridinepropanol, 2-pyridylacetic acid, 2-pyridylacetonitrile, pyridine-2-carboxylic acid, methyl picolinate, ethyl picolinate, n-propyl picolinate, i-propyl picolinate, n-butyl picolinate, t-butyl picolinate, phenyl picolinate, benzyl picolinate, picolinamide, 3-hydroxypicolinamide, N-methylpicolinamide, N-ethylpicolinamide, N,N-dimethylpicolinamide, N,N-diethylpicolinamide, 3-methylpyridine, 3-ethylpyridine, 3-butylpyridine, 3-phenylpyridine, 3-benzylpyridine, 3-acetylpyridine, 3-benzoylpyridine, 3-fluoropyridine, 3-chloropyridine, 3-bromopyridine, 3-pyridylcarbinol, 3-hydroxypyridine, 3-pyridinepropanol, 3-pyridylacetonitrile, 3-pyridylacetic acid, pyridine-3-carboxylic acid, methyl nicotinate, ethyl nicotinate, n-propyl nicotinate, i-propyl nicotinate, n-butyl nicotinate, t-butyl nicotinate, phenyl nicotinate, benzyl nicotinate, nicotinamide, 6-methylnicotinamide, thionicotinamide, N-methylnicotinamide, N-ethylnicotinamide, N,N-dimethylnicotinamide, N,N-diethylnicotinamide, N-(hydroxymethyl)-nicotinamide, 6-chloronicotinamide, 2-chloronicotinamide, 4-methylpyridine, 4-fluoropyridine, 4-chloropyridine, 4-bromopyridine, 4-cyanopyridine, 4-ethylpyridine, 4-isopropylpyridine, 4-t-butylpyridine, 4-(1-butylpentyl)pyridine, 4-phenylpyridine, 4-benzylpyridine, 4-(4-chlorobenzyl)pyridine, 4-pyridylacetic acid, 4-acetylpyridine, 4-benzoylpyridine, 4-(4-chlorobenzoyl)pyridine, 4-pyridylacetonitrile, isonicotinic acid, methyl isonicotinate, ethyl isonicotinate, n-propyl isonicotinate, i-propyl isonicotinate, n-butyl isonicotinate, t-butyl isonicotinate, phenyl isonicotinate, benzyl isonicotinate, isonicotinamide, N-methylisonicotinamide, N-ethylisonicotinamide, N,N-dimethylisonicotinamide, N,N-diethylisonicotinamide, thioisonicotinamide, N-(2-hydroxymethyl)-isonicotinamide, N,N-bis(2-hydroxymethyl)-isonicotinamide, 4-hydroxypyridine, 4-methoxypyridine, 4-nitropyridine, 4-pyridylcarbinol, pyridine-4-carboxylic acid, 2,3-lutidine, 2,4-lutidine, 2,5-lutidine, 2,6-lutidine, 3,4-lutidine, 3,5-lutidine, 3-methyl-2-phenylpyridine, 5-ethyl-2-methylpyridine, 2,6-di-tert-butylpyridine, 2,6-di-tert-butyl-4-methylpyridine, 2,6-diacetylpyridine, 2,6-difluoropyridine, pentafluoropyridine, 2,3,5,6-tetrafluoropyridine, pentachloropyridine, 2,3-dichloropyridine, 2,5-dichloropyridine, 2,6-dichloropyridine, 3,5-dichloropyridine, 2,3,5-trichloropyridine, 2,5-dibromopyridine, 2,6-dibromopyridine, 3,4-dicyanopyridine, 5-chloro-3-pyridinol, 2,3-pyridinedicarboxylic acid, dimethyl 2,3-pyridinedicarboxylate, diethyl 2,3-pyridinedicarboxylate, dipropyl 2,3-pyridinedicarboxylate, dibutyl 2,3-pyridinedicarboxylate, 2,4-pyridinedicarboxylic acid, dimethyl 2,4-pyridinedicarboxylate, diethyl 2,4-pyridinedicarboxylate, dipropyl 2,4-pyridinedicarboxylate, dibutyl 2,4-pyridinedicarboxylate, 2,5-pyridinedicarboxylic acid, dimethyl 2,5-pyridinedicarboxylate, diethyl 2,5-pyridinedicarboxylate, dipropyl 2,5-pyridinedicarboxylate, dibutyl 2,5-pyridinedicarboxylate, 3,5-pyridinedicarboxylic acid, dimethyl 3,5-pyridinedicarboxylate, diethyl 3,5-pyridinedicarboxylate, dipropyl 3,5-pyridinedicarboxylate, dibutyl 3,5-pyridinedicarboxylate, 2,6-pyridinedicarboxylic acid, dimethyl 2,6-pyridinedicarboxylate, diethyl 2,6- pyridinedicarboxylate, dipropyl 2,6-pyridinedicarboxylate, dibutyl 2,6-pyridinedicarboxylate, 2,6-diphenylpyridine, 2,6-di-p-tolylpyridine, 3,4-pyridinedicarboxylic acid, dimethyl 3,4-pyridinedicarboxylate, diethyl 3,4-pyridinedicarboxylate, dipropyl 3,4-pyridinedicarboxylate, dibutyl 3,4-pyridinedicarboxylate, 2-pyridine-ethansulfonic acid, 4-pyridineethanesulfonic acid, 2,3-cyclopentenopyridine, 2,3-cyclohexenopyridine, 2,3-cycloheptenopyridine, diphenyl-2-pyridylmethane, diphenyl-4-pyridylmethane, 6-chloro-2-picoline, 2-chloro-5-(trifluoromethyl)-pyridine, 2-chloro- 3,5-bis(trifluoromethyl)pyridine, 2-chloro-4,5-bis(trifluoromethyl)pyridine, 2-chloro-4,6-bis(trifluoromethyl)pyridine, 4-chloro-2,6-bis(trifluoromethyl)pyridine, 2,3-dichloro-5-(trifluoromethyl)pyridine, 2,3,5,6-tetrafluoro-4-methylpyridine,3-chloro-2,4,5,6-tetrafluoropyridine, 3,5-dichloro-2,4,6-trifluoropyridine, 4-bromo-2,3,4,6-tetrafluoropyridine, 2-(2-isopropoxyethyl)-pyridine, 2-(2-propoxyethyl)pyridine, 2-(2-hydroxyethyl)pyridine, 2,3-di-2-pyridyl-2,3-butanediol, 2,3-di-3-pyridyl-2,3-butanediol, α-4-pyridylbenzhydrol, 2-hydroxy-4-methylpyridine, 2-hydroxy-6-methylpyridine, 6-methyl-2-pyridinepropanol, 2-[3-(6-methyl-2-pyridyl)propoxy]ethanol, 3-hydroxy-2-methylpyridine, 6-chloro-2-pyridinol, 5-chloro-2-pyridinol, 2,3-dihydroxypyridine, 2,6-dihydroxypyridine, 5-chloro-2,3-pyridinediol, 2,2'-bipyridine-3,3'-diol, 2,4-dihydroxypyridine, 5-hydroxy-2-methylpyridine, 5-chloro-3-pyridinol, 2-chloro-3-pyridinol, 2-bromo-3-pyridinol, 3-hydroxy-2-(hydroxymethyl)-pyridine, 2,6-pyridinedimethanol, 2,6-lutidine-2,3-diol, pyridoxine, 4-amino-3,5-dichloro-2,6-difluoropyridine, 4-(4-nitrobenzyl)pyridine, 2-chloro-3-nitropyridine, 2-chloro-5-nitropyridine, 2-bromo-5-nitropyridine, 2-hydroxy-3-nitropyridine, 3-ethoxy-2-nitropyridine, 2-chloro-4-methyl-3-nitropyridine, 3-hydroxy-2-nitropyridine, 2,6-dichloro-3-nitropyridine, 2-hydroxy-4-methyl-3-nitropyridine, 2-chloro-3,5-dinitropyridine, 2-hydroxy-5-nitropyridine, 2-hydroxy-4-methyl-5-nitropyridine, 2-chloro-4-methyl-5-nitropyridine, 3-hydroxy-6-methyl-2-nitropyridine, α-pyridoin, 2-methyl-1,2-di-3-pyridyl-1-propanone, 3-acetyl-2,6-bis(tert-butylamino)-4-methylpyridine, 2,2'-bipyridine-4,4'dicarboxylic acid, 2-methylnicotinic acid, 6-methylnicotinic acid, fusaric acid, 2-chloronicotinic acid, 5-bromonicotinic acid, 6-chloronicotinic acid, 2-chloro-6-methylnicotinic acid, 2,6-dichloronicotinic acid, 5,6-dichloronicotinic acid, 6-hydroxynicotinic acid, 3-hydroxypicolinic acid, 2-hydroxynicotinic acid, 2-hydroxy-6-methylpyridine-3-carboxylic acid, 5-chloro-6-hydroxynicotinic acid, 4-pyridoxic acid, 2,6-dimethoxynicotinic acid, citrazinic acid, 6-methyl-2,3-pyridinedicarboxylic acid, methyl-2-pyridylacetate, ethyl 2-pyridylacetate, 3-acetoxypyridine, methyl 6-methylnicotinate, ethyl 2-methylpicolinate, ethyl 3-pyridylacetate, 3,4-pyridinedicarboxamide, 3,4-pyridinedicarboximide, methyl 3-pyridylcarbamate, 1-(3-pyridylmethyl)urea, 1,3-bis(3-pyridylmethyl)-2-thiourea, trans-4-cotininecarboxylic acid, 3-(3-pyridylmethylamino)-propionitrile, 3,4-pyridinedicarbonitrile, 2-chloro-6-methyl-3-pyridinecarbonitrile, 3-cyano-4,6-dimethyl-2-hydroxypyridine, 2,6-dihydroxy-4-methyl-3-pyridinecarbonitrile, 2,3,5,6-tetrafluoro-4-pyridinecarbonitrile, 2,4,6-collidine, pyrazine, 2,3-pyrazinedicarbonitrile, pyrazinecarbonitrile, 2,6-dichloropyrazine, pyrazinecarboxylic, methyl pyrazinecarboxylate, ethyl pyrazinecarboxylate, propyl pyrazinecarboxylate, butyl pyrazinecarboxylate, 2,3-dimethylpyrazine, 2,5-dimethylpyrazine, 2,6-dimethylpyrazine, 2,3-di-2-pyridylpyrazine, 2-methylpyrazine, ethylpyrazine, 2,6-dimethylpyrazine, 2,5-dimethylpyrazine, 2,3-dimethylpyrazine, 2-ethyl-3-methylpyrazine, 2,3-diethylpyrazine, 2-methyl-3-propylpyrazine, 5,6,7,8-tetrahydroquinoxaline, 2,3,5-trimethylpyrazine, 2,3-diethyl-5-methylpyrazine, tetramethylpyrazine, chloropyrazine, 2-methoxypyrazine, 2-methoxy-3-methylpyrazine, 2-ethyl-3-methoxypyrazine, 2-isopropyl-3-methoxypyrazine, 2-sec-butyl-3-methoxypyrazine, 2-isobutyl-3-methoxypyrazine, 2-methyl-6-propoxypyrazine, 3-chloro-2,5-dimethylpyrazine, acetylpyrazine, 2-pyrazinecarboxylic acid, 5-methyl-2-pyrazinecarboxylic acid, 2,3-pyrazinedicarboxylic acid, pyrazinamide, 2,3-pyrazinedicarboxamide, 2,3-bis(2-pyridyl)pyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinol, 2-chloropyrimidine, 5-bromopyrimidine, 2,4,6-trichloropyrimidine, 2,4,5,6-tetrachloropyrimidine, 2,4-dichloro-6-methylpyrimidine, 2,4-dichloro-6-methylpyrimidine, 6-chloro-2,4-dimethoxypyrimidine, 2-hydroxypyrimidine, 4,6-dimethyl-2-hydroxypyrimidine, 2,4-dimethyl-6-hydroxypyrimidine, 4,6-dimethyl-2-hydroxypyrimidine, 2-isopropyl-6-methyl-4-pyrimidinol, 4,6-dihydroxypyrimidine, 2,4-dihydroxy-5,6-dimethylpyrimidine, 2,4-dihydroxy-6-methylpyrimidine, 4,6-dihydroxy-2-methylpyrimidine, 2,4,5-trihydroxypyrimidine, 4,6-dichloro-5-nitropyrimidine, 4,6-dihydroxy-5-nitropyrimidine, 2,4-dihydroxypyrimidine-5-carboxylic acid, 1,3,5-triazine, 2-chloro-4,6-dimethoxy-1,3,5-triazine, 2,4,6-triphenoxy-1,3,5-triazine, 2,4,6-triphenyl-1,3,5-triazine, 2,4,6-tri(2-pyridyl)-1,3,5-triazine, (−)-cotinine (1-methyl-5-(3-pyridyl)-2-pyrrolidinone), quinoline, 2,2'-biquinoline, quinaldine, lepidine, 6-methylquinoline, 7-methylquinoline, 8-methylquinoline, 2,4-dimethylquinoline, 2,6-dimethylquinoline, 2,7-dimethylquinoline, 2,8-dimethylquinoline, 2-phenylquinoline, 7,8-benzoquinoline, 2-chloroquinoline, alpha,alpha,alpha-tribromoquinaldine, 4-chloroquinoline, 6-chloroquinoline, 4-chloro-7-(trifluoromethyl)quinoline, 4-chloro-8-(trifluoromethyl)quinoline, 4-chloro-2,8-bis(trifluoromethyl)quinoline, 4-chloroquinaldine, 7-chloroquinaldine, 2-chlorolepidine, 3-bromoquinoline, 4,7-dichloroquinoline, 4-bromo-2,8-bis(trifluoromethyl)quinoline, 6-methoxyquinoline, 6-methoxyquinaldine, 2-hydroxy-4-methylquinoline, 4-hydroxyquinoline, 7-chloro-4-hydroxyquinoline, 8-(trifluoromethyl)-4-quinolinol, 2,4-quinolinediol, 2-hydroxyquinoline, 5-hydroxyquinoline, 6-hydroxyquinoline, 8-hydroxyquinoline, 8-hydroxyquinaldine, 4-hydroxy-2-methylquinoline, 7-(trifluoromethyl)-4-quinolinol, 2,8-bis(trifluoromethyl)-4-quinolinol, 5-chloro-8-hydroxyquinoline, 5,7-dichloro-8-hydroxyquinoline, 5,7-dibromo-8-hydroxyquinoline, 5,7-dibromo-2-methyl-8-quinolinol, 5,7-dichloro-2-methyl-8-quinolinol, 5-nitroquinoline, 6-nitroquinoline, 8-nitroquinoline, 8-nitroquinaldine, 8-methyl-5-nitroquinoline, 8-hydroxy-5-nitroquinoline, 6-methoxy-8-nitroquinoline, quinaldic acid, 3-quinolinecarboxylic acid, 4-quinolinecarboxylic acid, 8-quinolinecarboxylic acid, 1,2,3,4-tetrahydro-9-acridinecarboxylic acid, 4-methoxy-2-quinolinecarboxylic acid, 4-hydroxyquinoline-2-carboxylic acid, 4-hydroxy-7-trifluoromethyl-3-quinolinecarboxylic acid, 4,8-dihydroxyquinoline-2-carboxylic acid, 2-phenyl-4-quinolinecarboxylic acid, ethyl 4-hydroxy-7- trifluoromethyl-3-quinolinecarboxylate, methyl 2-phenyl-4-quinolinecarboxylate, 2-quinolinecarbonitrile, 3-quinolinecarbonitrile, 2,8-bis(trifluoromethyl)-4-quinolinecarbonitrile, 5,6,7,8-tetrahydroisoquinoline, 3-methyl-5,6,7,8-tetrahydroquinoline, 1,2,3,4,5,6,7,8-octahydroacridine, acridine, 5-triazolo(4,3-A)quinoline, 6,9-dichloro-2-methoxyacridine, 9-hydroxy-4-methoxyacridine, 9-acridinecarboxylic acid, 4,9-acridinedicarboxylic acid, 1,3-dihydroxy-9-acridinecarboxylic acid, phenyl 9-acridinecarboxylate, isoquinoline, 3-methylisoquinoline, 4-bromoisoquinoline, 1,3-dichloroisoquinoline, papaverine, isocarbostyril, 3-hydroxyisoquinoline, 5-hydroxyisoquinoline, 1,5-isoquinolinediol, 5-nitroisoquinoline, 1-isoquinolinyl phenyl ketone, protopapaverine, 1-isoquinolinecarboxylic acid, 3-isoquinolinecarboxylic acid, methyl 3-isoquinolinecarboxylate, 1-isoquinolinecarbonitrile, 3-isoquinolinecarbonitrile, benz[g]isoquinoline-5,10-dione, 3,8-dinitro-6-phenylphenanthridine, cinnoline, phenanthridine, 3,8-diamino- 6-phenylphenanthridine, benzo[c]cinnoline, cinnoline-4-carboxylic acid, phthalazine, 1,4-dichlorophthalazine, 1(2H)-phthalazinone, quinazoline, 4-hydroxyquinazoline, 2-methyl-4(3H)-quinazolinone, quinoxaline, 2-methylquinoxaline, 5-methylquinoxaline, 2,3-dimethylquinoxaline, ethyl 2-quinoxalinecarboxylate, 2,3-diphenylquinoxaline, 6,7-dimethyl-2,3-di-(2-pyridyl)quinoxaline, phenazine, 2,3-dichloroquinoxaline, 2,3,6,7-tetrachloroquinoxaline, 2,3-bis(bromomethyl)-quinoxaline, 2-quinoxalinol, 3-methyl-2-quinoxalinol, 2,3-dihydroxyquinoxaline, 2-quinoxalinecarboxylic acid, 3-hydroxy-2-quinoxalinecarboxylic acid, 4-hydroxy-7-methyl-1,8-naphthyridine-3-carboxylic acid, 2,2'-pyridyl, 2,2'-dipyridyl, 4,4'-dimethyl-2,2'-dipyridyl, 4,4'-diphenyl-2,2'dipyridyl, 6-chloro-2,2'-bipyridine, 2,4'-dipyridyl, 4,4'-dipyridyl, di-2-pyridyl ketone, 2,2':6',2"-terpyridine, 1,7-phenanthroline, 1,10-phenanthroline, 4,7-phenanthroline, phenazine, 4-methyl-1,10-phenanthroline, 5-methyl-1,10-phenanthroline, neocuproine, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,9-dimethyl-4,7-diphenyl-1,10-phenanthroline, 5-chloro-1,10-phenanthroline, 6,7-dihydro-5,8-dimethyldibenzo-(1-10)-phenanthroline, 5-nitro-1,10-phenylanthroline, 7-oxo-7-H-benzo[e]perimidine-4-carboxylic acid, lumazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-phenylpyrazole, 3-methyl-1-phenylpyrazole, 3-methyl-1-phenyl-2-pyrazolin-5-one, 4-benzoyl-3-methyl-1-phenyl-2-pyrazolin-5-one, 4-(3-methyl-5-oxo-2-pyrazolin-1-yl)-benzoic acid, 3,5-dimethylpyrazole-1-carboxamide, 1-nitropyrazole, oxazole, 2,5-diphenyloxazole, 2,4,5-trimethyloxazole, 1,4-bis(5-phenyloxazol-2-yl)-benzene, 1,4-bis(4-methyl-5-phenyloxazol-2-yl)benzene, 5-phenyl-2-(4-pyridyl)-oxazole, 2-(4-biphenylyl)-5-phenyloxazole, 2,5-bis(4-biphenylyl)oxazole, 2-methyl-4,5-diphenyloxazole, 9,10-dihydro-2-methyl-4H-benzo(5,6)cyclohept(1,2)-oxazol-4-ol, N1-(4,5-dimethyloxazol-2-yl)-sulfanilamide, 2,5-diphenyl-1,3,4-oxadiazole, 2-(4-biphenylyl)-5-phenyl-1,3,4-oxadiazole, 2-(4-biphenylyl)-5-(4-tert-butylphenyl)-1,3,4-oxadiazole, 2,5-bis(4-aminophenyl)-1,3,4-oxadiazole, 2,5-bis(4-diethylaminophenyl)-1,3,4-oxadiazole, benzoxazole, 2-methylbenzoxazole, 2,5-dimethylbenzoxazole, 2-methyl-5-phenylbenzoxazole, 2-(4-biphenylyl)-6-phenylbenzoxazole, 2-chlorobenzoxazole, 2-phenylbenzoxazole, 2-(2'-hydroxyphenyl)-benzoxazole, 2,4,4-trimethyl-2-oxazoline, isoxazole, 1,2-benzisoxazole, 3,5-dimethylisoxazole, 5-methylisoxazole, 3,5-dimethylisoxazole, 4-(chloromethyl)-3,5-dimethylisoxazole, 3,5-dimethyl-4-nitroisoxazole, 5-methyl-3-phenylisoxazole-4-carboxylic acid, N,5-dimethyl-3-phenylisoxazole-4-carboxamide, N,5-dimethyl-3-(4-fluorophenyl)-4-isoxazolecarboxamide, 2,5-diphenyloxazole, 2,6-bis[(4S)-isopropyl-2-oxazolin-2-yl]pyridine, 1,5-pentamethylenetetrazole, 1,2-dimethylimidazole, 1-methylimidazole, 1-ethylimidazole, 1-propylimidazole, 1-butylimidazole, 1-phenylimidazole, 1-benzylimidazole, 1-benzyl-2-1-(2,3,4,6-tetrafluorophenyl)-imidazole, 1-(2-chloroethyl)-2-methyl-5-nitroimidazole, metronidazole, 2-methyl-4-nitro-1-imidazolepropionic acid, 2-methyl-4-nitro-1-imidazolepropionitrile, 1,5-dicyclohexylimidazole, 5-chloro-1-methylimidazole, 5-chloro-1-ethyl-2-methylimidazole, 4-(imidazol-1-yl)phenol, imidazo(1,2-A)pyridine, anthranil, 2,3,3-trimethylindolenine, caffeine and 6-chloropurine riboside.

When used at a concentration greater than or equal to 2.0 mole percent with respect to 1 mole of the olefin substrate, the accelerant has demonstrated significant improvement in the MTO epoxidation of non cyclic olefins, endocyclic olefins and exocyclic olefins (see discussion covering substrate scope vida infra).

For terminal alkenes, 3-cyanopyridine has shown to be superior to pyridine. Its advantage is most likely based on the preservation of the catalyst lifetime. For most other alkenes, however, pyridine works better because it suppresses side reactions such as hydrolytic ring opening more effectively than the 3-cyanopyridine. Terminal alkenes are less susceptible to these kinds of side reactions. The reaction procedure for the 3-cyanopyridine is the same as that for pyridine (preferred embodiment 10 mol % accelerant used instead of 12 mol %, 0.5% MTO, 2.0 equivalents hydrogen peroxide.

Organorhenium Oxide

The preferred embodiment uses methyl rhenium oxide (MTO) as the catalyst for oxidation at a concentration of 0.5 mole percent with respect to the olefin substrate. The operable range (of which the improved acceleration effect from the accelerant is observed) is in a range from 0.10 mole percent to 1.0 mole percent of the organo rheniumoxide with respect to the olefin substrate wherein the preferred embodiment uses 0.5 mole percent. MTO is commercially available from Aldrich, and the remaining organorhenium oxides are synthesized as disclosed vida infra and are highly applicable in use with the accelerated method for MTO/accelerant-catalyzed epoxidation of an olefin as disclosed herein. These applicable organorhenium oxides, used in the concentration range outlined, are the following compounds as represented by the formula $R_1ReO_3$ wherein $R_1$=methyl, ethyl, n-propyl, n-butyl, n-pentyl, n-hexyl, heptyl, octyl, isopropyl, t-butyl, adamantyl, phenyl, benzyl, cyclopropyl, cyclobutyl, cyclopentyl, cyclohexyl, 1-bicyclo(2.2.2)octanyl, 1-bicyclo(2.2.1)heptanyl, 1-bicyclo(2.1.1)hexanyl, 1-bicyclo(1.1.1)pentanyl, 1-bicyclo(3.2.1)octanyl, 1-bicyclo(1.1.3)heptanyl, cubyl, sec-butyl, neo-pentyl, 3-methylbutyl, (S)-2-methylbutyl, (R,S)-2-ethylhexyl, trimethylsilylmethyl, γ-diethylamino-n-propyl, tolyl, 2,6-dimethylphenyl, 2,4,6-trimethylphenyl, pentafluorophenyl, 4-hydroxy-2,6-dimethylphenyl, 4-trimethylsiloxy-2,6-dimethylphenyl, ethynyl, phenylethynyl, methylallyl, methylvinyl, 2,4-pentadienyl, and ethylacetyl.

Substrate

As illustrated in FIG. 3, equation 1, the process is compatable with most non-cyclic olefins which have mono, di, tri and tetra substitutions. A representative but nonexhaustive example of substitutions on a non-cyclic olefin are included as follows, wherein $R_1$, $R_2$, $R_3$ and $R_4$ of said olefin, FIG. 3, equation 1, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, Br, OH, and $C_1$-$C_6$ alkyl containing the following substitutions: F, Cl, Br, CN, OH, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, OR, NRR', etc.

As illustrated in FIG. 3, equation 2, the process is compatable with most endocyclic olefins which have mono and di substitutions. A representative but nonexhaustive example of substitutions on an endocyclic olefin are included as follows, wherein $R_1$ and $R_2$ of said olefin, FIG. 3, equation 2, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, Br, OH, and $C_1$-$C_6$ alkyl containing the following substitutions: F, Cl, Br, CN, OH, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, OR, NRR', etc. The variable "x" represents a range of rings including $C_4H_4$ to $C_8H_{16}$ (cyclobutane to cyclodecene-derivatives [cis and trans]), etc.

As illustrated in FIG. 3, equation 3, the process is compatable with most exocyclic olefins which have mono and di substitutions. A representative but nonexhaustive example of substitutions on an endocyclic olefin are included as follows, wherein $R_1$ and $R_2$ of said olefin, FIG. 3, equation 3, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$(sulfonamides), CN, F, Cl, Br, OH, and $C_1$-$C_6$ alkyl containing the following substitutions: F, Cl, Br, CN, OH, COOH, C(O)OR (esters, lactones), C(O)N (amide, lactam), $SO_3H$ (sulfonic acid), $SO_2O$—$C_1$-$C_6$ (sulfonic acid esters), $SO_2NH$—$C_1$-$C_6$ (sulfonamides), CN, F, Cl, OR, NRR', etc. The variable "x" represents a range of rings including $C_4H_4$ to $C_8H_{16}$ (cyclobutane to cyclodecene-derivatives [cis and trans]), etc.

The process is also compatible with dienes, trienes, and polyolefines including conjugated and isolated double bond compounds like allenes. Furthermore, double bonds in natural products and drug precursors like terpenes, e.g. pinene derivatives, steroids, e.g. cholesterol and cholesterol acetate, and unsaturated fatty acids and their esters are equally accessible for conversion to epoxides using the process. Examples for the fatty acids are palmitoleic acid (cis-9-hexadienoic acid) and its esters (methyl, ethyl, propyl-isomers, butyl-isomers, glyceryl etc.), oleic acid (cis-9-octadecenoic acid) and its esters (methyl, ethyl, propyl-isomers, butyl-isomers, glyceryl etc.), ricinoleic acid (cis-12-hydroxy-octadecenoic acid) and its esters (methyl, ethyl, propyl-isomers, butyl-isomers, glyceryl etc.), linoleic acid (cis,cis-9,12-octadecadienoic acid) and its esters (methyl, ethyl, propyl-isomers, butyl-isomers, glyceryl etc.), and linolenic acid (cis,cis,cis-9,12,15-octadecatrienoic acid) and its esters (methyl, ethyl, propyl-isomers, butyl-isomers, glyceryl etc.). Raw materials such as olive oil (~80% oleic acid), corn oil (~60% linoleic acid), linseed oil (~55% linolenic acid), castor oil hydrolyzate (~80% ricinoleic acid) can also be used in place of the pure acids.

Oxidant

The process uses hydrogen peroxide as the primary oxidant wherein the process works in amounts ranging from 1.0 equivalents to 3.0 equivalents of commercially available 30% hydrogen peroxide with respect to the olefin substrate (alternative concentrations from 10% to 85% hydrogen peroxide in amounts ranging from 1.0 equivalents to 3.0 equivalents are also reasonable; preferred embodiment 1.5 equivalents of 30% hydrogen peroxide for monoenes).

Solvent

The following solvents are highly applicable in use with the accelerant accelerated method for MTO/accelerant-catalyzed epoxidation of an olefin. The applicable solvents and solvent mixtures used in in concentrations ranging from 0.0025 Molar to Neat substrate eg. no solvent (preferred embodiment at 1.5 Molar) are as follows: nitromethane, nitroethane, methylene chloride, chloroform, carbon tetrachloride, freon-12, chloroethane, 1,2-dichloroethane, pentachloroethane, 1-chloropropane, 1-chlorobutane, chlorobenzene, dichlorobenzene, trichlorobenzene, fluorobenzene, difluorobenzene, trifluorobenzene, trifluoromethylbenzene, fluoroethane, acetonitrile, acetone, benzene, toluene, 2-fluorotoluene, 4-fluorotoluene, nitrobenzene, o-xylene, m-xylene, p-xylene, mesitylene, 1,2,3-trimethyl benzene, 1,2,4-trimethyl benzene, methanol, ethanol, propanol, isopropanol, butanol, t-butanol, ethyleneglycol, diethylether, dioxane, tetrahydrofuran, and supercritical $CO_2$.

The acceleration effect of accelerants is most pronounced in aprotic and noncoordinating solvents such as $CH_2Cl_2$ and $CH_3NO_2$.

The following mixtures in any ratio combination can also be used: nitromethane/t-butanol, nitromethane/n-propanol, nitromethane/i-propanol, nitromethane/ethanol, nitromethane/methanol, methylene chloride/t-butanol, methylene chloride/n-propanol, methylene chloride/i-propanol, methylene chloride/ethanol, methylene chloride/methanol, chloroform/t-butanol, chloroform/n-propanol, chloroform/i-propanol, chloroform/ethanol, and chloroform/methanol.

Experimental Protocals

General $^1H$ and $^{13}C$ nmr spectra were recorded either on a Bruker AM-250, a Bruker AMX-400 or a Bruker AMX-500 spectrometer. Residual protic solvent $CHCl_3$ ($\delta_H$=7.26 ppm, $\delta_C$=77.0), TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel $F_{254}$) and visualized by cerium molybdophosphate or ninhydrin. Diethyl ether, tetrahydrofuran (THF) and toluene ($PhCH_3$) were distilled from sodium-benzophenone ketyl, dichloromethane (DCM) and acetonitrile from calcium hydride. Other solvents and reagents were purified by standard procedures if necessary. TLC was performed on pre-coated Kieselgel 60 $F_{254}$ plates (Merck). Column chromatography was carried out on Kieselgel 60 (70–230 mesh and 230–400 mesh) and MCI gel CHP-20P (Mitsubishi Chemical, Ind.). The varying concentrations of hydrogen peroxide are purchased commercially from Fisher, Sigma, Aldrich, Fluka, etc.

General Methodology for the MTO-catalyzed/accelerant-accelerated epoxidation of an olefin In a standard reaction vessel, the olefin substrate (1.0 equivalent; applicable olefins are listed vida infra) is dissolved in the solvent (the process works in concentrations ranging from 0.0025 Molar to Neat (preferred embodiment at 1.5 Molar); applicable solvents are listed vida infra) and the organorhenium oxide is added (the process works in catalytic amounts ranging from 0.10 mole percent to 1.0 mole percent of the organo rheniumoxide with respect to the olefin substrate (preferred embodiment 0.5 mole percent); applicable organorhenium oxides are listed vida infra).

To this solution is added the accelerant wherein the process works in amounts ranging from 2.0 mole percent to mole 100 mole percent of the accelerant with respect to the olefin substrate (preferred embodiment 12.0 mole percent accelerant); applicable accelerants are listed vida infra. The process works optimally in a range from −10° C. to +30° C. wherein the temperature is stabilized by using a cooling bath (note that the process can be carried out at room temperature). External cooling with cold water is generally recommended, especially in large scale applications. Applying temperatures of approximately 5–10° C. in the initial state of the reaction gives, in some cases better results (the lifetime of catalyst might be enhanced). Applying temperatures in the range of 50° C. and higher diminishes the catalyst activity dramatically.

To this solution is added dropwise hydrogen peroxide wherein the process works in amounts ranging from 1.0 equivalents to 3.0 equivalents of commercially available 30% hydrogen peroxide with respect to the olefin substrate (alternative concentrations from 10% to 85% hydrogen peroxide in amounts ranging from 1.0 equivalents to 3.0 equivalents are also reasonable; preferred embodiment 1.5 equivalents of 30% hydrogen peroxide for monoenes). The color of the solution turns yellow which indicates the formation of the catalyticly active ligand-rhenium-peroxo species. When the yellow color has disappeared no further conversion is observed. In addition, the order of addition does not seem to play a role, except that $H_2O_2$ has to be added at last.

Workup: The excess $H_2O_2$ is quenched by adding a small portion of $MnO_2$ (generally 0.010 equivalents while cooling at large scale), leading to rapid disproportionation to oxygen and water. Other standard quenching methods include the addition of mild reducing agents such as $NaHSO_3$, $Na_2SO_3$, etc. Quenching can also be left out. The solution is dried by adding $Na_2SO_4$ and seperated from inorganic material by filtering through a small deactivated silica column (wash with ethyl acetate). A further purification which may include a column purification, distillation, recrystallization, etc. can be used if incomplete conversion to product. Generally, the formation of side products is not observed in most cases leading to complete consumption of the starting olefin substrate and generating a near quantitative epoxide yield.

Applicable Accelerants for General Method for MTO/accelerant-catalyzed epoxidation of an olefin The following accelerants are commercially available from Aldrich, Sigma and Fluka and are highly applicable in use with the general method for MTO/accelerant-catalyzed epoxidation of an olefin as disclosed vida supra. The applicable accelerants used in the concentration range outlined in the general method are as follows: pyridine, 3-cyanopyridine, 2-cyanopyridine, cotinine, 2-picoline, 2-ethylpyridine, 2-propylpyridine, 2-phenylpyridine, 2-(p-tolyl)pyridine, 2-benzylpyridine, 2-acetylpyridine, 2-benzoylpyridine, 2-fluoropyridine, 2-chloropyridine, 2-bromopyridine, 2-hydroxypyridine, 2-pyridylcarbinol, 2-pyridineethanol, 2-pyridinepropanol, 2-pyridylacetic acid, 2-pyridylacetonitrile, pyridine-2-carboxylic acid, methyl picolinate, ethyl picolinate, n-propyl picolinate, i-propyl picolinate, n-butyl picolinate, t-butyl picolinate, phenyl picolinate, benzyl picolinate, picolinamide, 3-hydroxypicolinamide, N-methylpicolinamide, N-ethylpicolinamide, N,N-dimethylpicolinamide, N,N-diethylpicolinamide, 3-methylpyridine, 3-ethylpyridine, 3-butylpyridine, 3-phenylpyridine, 3-benzylpyridine, 3-acetylpyridine, 3-benzoylpyridine, 3-fluoropyridine, 3-chloropyridine, 3-bromopyridine, 3-pyridylcarbinol, 3-hydroxypyridine, 3-pyridinepropanol, 3-pyridylacetonitrile, 3-pyridylacetic acid, pyridine-3-carboxylic acid, methyl nicotinate, ethyl nicotinate, n-propyl nicotinate, i-propyl nicotinate, n-butyl nicotinate, t-butyl nicotinate, phenyl nicotinate, benzyl nicotinate, nicotinamide, 6-methylnicotinamide, thionicotinamide, N-methylnicotinamide, N-ethylnicotinamide, N,N-dimethylnicotinamide, N,N-diethylnicotinamide, N-(hydroxymethyl)-nicotinamide, 6-chloronicotinamide, 2-chloronicotinamide, 4-methylpyridine, 4-fluoropyridine, 4-chloropyridine, 4-bromopyridine, 4-cyanopyridine, 4-ethylpyridine, 4-isopropylpyridine, 4-t-butylpyridine, 4-(1-butylpentyl)pyridine, 4-phenylpyridine, 4-benzylpyridine, 4-(4-chlorobenzyl)pyridine, 4-pyridylacetic acid, 4-acetylpyridine, 4-benzoylpyridine, 4-(4-chlorobenzoyl)pyridine, 4-pyridylacetonitrile, isonicotinic acid, methyl isonicotinate, ethyl isonicotinate, n-propyl isonicotinate, i-propyl isonicotinate, n-butyl isonicotinate, t-butyl isonicotinate, phenyl isonicotinate, benzyl isonicotinate, isonicotinamide, N-methylisonicotinamide, N-ethylisonicotinamide, N,N-dimethylisonicotinamide, N,N-diethylisonicotinamide, thioisonicotinamide, N-(2-hydroxymethyl)-isonicotinamide, N,N-bis(2-hydroxymethyl)-isonicotinamide, 4-hydroxypyridine, 4-methoxypyridine, 4-nitropyridine, 4-pyridylcarbinol, pyridine-4-carboxylic acid, 2,3-lutidine, 2,4-lutidine, 2,5-lutidine, 2,6-lutidine, 3,4-lutidine, 3,5-lutidine, 3-methyl-2-phenylpyridine, 5-ethyl-2-methylpyridine, 2,6-di-tert-butylpyridine, 2,6-di-tert-butyl-4-methylpyridine, 2,6-diacetylpyridine, 2,6-difluoropyridine, pentafluoropyridine, 2,3,5,6-tetrafluoropyridine, pentachloropyridine, 2,3-dichloropyridine, 2,5-dichloropyridine, 2,6-dichloropyridine, 3,5-dichloropyridine, 2,3,5-trichloropyridine, 2,5-dibromopyridine, 2,6-dibromopyridine, 3,4-dicyanopyridine, 5-chloro-3-pyridinol, 2,3-pyridinedicarboxylic acid, dimethyl 2,3-pyridinedicarboxylate, diethyl 2,3-pyridinedicarboxylate, dipropyl 2,3-pyridinedicarboxylate, dibutyl 2,3-pyridinedicarboxylate, 2,4-pyridinedicarboxylic acid, dimethyl 2,4-pyridinedicarboxylate, diethyl 2,4-pyridinedicarboxylate, dipropyl 2,4-pyridinedicarboxylate, dibutyl 2,4-pyridinedicarboxylate, 2,5-pyridinedicarboxylic acid, dimethyl 2,5-pyridinedicarboxylate, diethyl 2,5-pyridinedicarboxylate, dipropyl 2,5-pyridinedicarboxylate, dibutyl 2,5-pyridinedicarboxylate, 3,5-pyridinedicarboxylic acid, dimethyl 3,5-pyridinedicarboxylate, diethyl 3,5-pyridinedicarboxylate, dipropyl 3,5-pyridinedicarboxylate, dibutyl 3,5-pyridinedicarboxylate, 2,6-pyridinedicarboxylic acid, dimethyl 2,6-pyridinedicarboxylate, diethyl 2,6-pyridinedicarboxylate, dipropyl 2,6-pyridinedicarboxylate, dibutyl 2,6-pyridinedicarboxylate, 2,6-diphenylpyridine, 2,6-di-p-tolylpyridine, 3,4-pyridinedicarboxylic acid, dimethyl 3,4-pyridinedicarboxylate, diethyl 3,4-pyridinedicarboxylate, dipropyl 3,4-pyridinedicarboxylate, dibutyl 3,4-pyridinedicarboxylate, 2-pyridine-ethansulfonic acid, 4-pyridineethanesulfonic acid, 2,3-cyclopentenopyridine, 2,3-cyclohexenopyridine, 2,3-cycloheptenopyridine, diphenyl-2-pyridylmethane, diphenyl-4-pyridylmethane, 6-chloro-2-picoline, 2-chloro-5-(trifluoromethyl)-pyridine, 2-chloro-3,5-bis(trifluoromethyl)pyridine, 2-chloro- 4,5-bis(trifluoromethyl)pyridine, 2-chloro-4,6-bis(trifluoromethyl)pyridine, 4-chloro-2,6-bis(trifluoromethyl)pyridine, 2,3-dichloro-5-(trifluoromethyl)pyridine, 2,3,5,6-tetrafluoro-4-methylpyridine,3-chloro-2,4,5,6-tetrafluoropyridine, 3,5-dichloro-2,4,6-trifluoropyridine, 4-bromo-2,3,4,6-tetrafluoropyridine, 2-(2-isopropoxyethyl)-pyridine, 2-(2-propoxyethyl)pyridine, 2-(2-hydroxyethyl)pyridine, 2,3-di-2-pyridyl-2,3-butanediol, 2,3-di-3-pyridyl-2,3-butanediol, α-4-pyridylbenzhydrol, 2-hydroxy-4-methylpyridine, 2-hydroxy-6-methylpyridine, 6-methyl-2-pyridinepropanol, 2-[3-(6-methyl-2-pyridyl)propoxy]ethanol, 3-hydroxy-2-methylpyridine, 6-chloro-2-pyridinol, 5-chloro-2-pyridinol, 2,3-dihydroxypyridine, 2,6-dihydroxypyridine, 5-chloro-2, 3-pyridinediol, 2,2'-bipyridine-3,3'-diol, 2,4-dihydroxypyridine, 5-hydroxy-2-methylpyridine, 5-chloro-3-pyridinol, 2-chloro-3-pyridinol, 2-bromo-3-pyridinol, 3-hydroxy-2-(hydroxymethyl)-pyridine, 2,6-pyridinedimethanol, 2,6-lutidine-2,3-diol, pyridoxine, 4-amino-3,5-dichloro-2,6-difluoropyridine, 4-(4-nitrobenzyl)pyridine, 2-chloro-3-nitropyridine, 2-chloro-5-nitropyridine, 2-bromo-5-nitropyridine, 2-hydroxy-3-nitropyridine, 3-ethoxy-2-nitropyridine, 2-chloro-4-methyl-3-nitropyridine, 3-hydroxy-2-nitropyridine, 2,6-dichloro-3-nitropyridine, 2-hydroxy-4-methyl-3-nitropyridine, 2-chloro-3,5-dinitropyridine, 2-hydroxy-5-nitropyridine, 2-hydroxy-4-methyl-5-nitropyridine, 2-chloro-4-methyl-5-nitropyridine, 3-hydroxy-6-methyl-2-nitropyridine, α-pyridoin, 2-methyl-1,2-di-3-pyridyl-1-propanone, 3-acetyl-2,6-bis(tert-butylamino)-4-methylpyridine, 2,2'-bipyridine-4,4'dicarboxylic acid, 2-methylnicotinic acid, 6-methylnicotinic acid, fusaric acid, 2-chloronicotinic acid, 5-bromonicotinic acid, 6-chloronicotinic acid, 2-chloro-6-methylnicotinic acid, 2,6-dichloronicotinic acid, 5,6-dichloronicotinic acid, 6-hydroxynicotinic acid, 3-hydroxpicolinic acid, 2-hydroxynicotinic acid, 2-hydroxy-6-methylpyridine-3-carboxylic acid, 5-chloro-6-hydroxynicotinic acid, 4-pyridoxic acid, 2,6-dimethoxynicotinic acid, citrazinic acid, 6-methyl-2,3-pyridinedicarboxylic acid, methyl-2-pyridylacetate, ethyl 2-pyridylacetate, 3-acetoxypyridine, methyl 6-methylnicotinate, ethyl 2-methylpicolinate, ethyl 3-pyridylacetate, 3,4-pyridinedicarboxamide, 3,4-pyridinedicarboximide, methyl 3-pyridylcarbamate, 1-(3-pyridylmethyl)urea, 1,3-bis(3-pyridylmethyl)-2-thiourea, trans-4-cotininecarboxylic acid, 3-(3-pyridylmethylamino)-propionitrile, 3,4-pyridinedicarbonitrile, 2-chloro-6-methyl-3-pyridinecarbonitrile, 3-cyano-4,6-dimethyl-2-hydroxypyridine, 2,6-dihydroxy-4-methyl-3-pyridinecarbonitrile, 2,3,5,6-tetrafluoro-4-pyridinecarbonitrile, 2,4,6-collidine, pyrazine, 2,3-pyrazinedicarbonitrile, pyrazinecarbonitrile, 2,6-dichloropyrazine, pyrazinecarboxylic, methyl pyrazinecarboxylate, ethyl pyrazinecarboxylate, propyl pyrazinecarboxylate, butyl pyrazinecarboxylate, 2,3-dimethylpyrazine, 2,5-dimethylpyrazine, 2,6-dimethylpyrazine, 2,3-di-2-pyridylpyrazine, 2-methylpyrazine, ethylpyrazine, 2,6-dimethylpyrazine, 2,5-dimethylpyrazine, 2,3-dimethylpyrazine, 2-ethyl-3-methylpyrazine, 2,3-diethylpyrazine, 2-methyl-3-propylpyrazine, 5,6,7,8-tetrahydroquinoxaline, 2,3,5-trimethylpyrazine, 2,3-diethyl-5-methylpyrazine, tetramethylpyrazine, chloropyrazine, 2-methoxypyrazine, 2-methoxy-3-methylpyrazine, 2-ethyl-3-methoxypyrazine, 2-isopropyl-3-methoxypyrazine, 2-sec-butyl-3-methoxypyrazine, 2-isobutyl-3-methoxypyrazine, 2-methyl-6-propoxypyrazine, 3-chloro-2,5-dimethylpyrazine, acetylpyrazine, 2-pyrazinecarboxylic acid, 5-methyl-2-pyrazinecarboxylic acid, 2,3-pyrazinedicarboxylic acid, pyrazinamide, 2,3-pyrazinedicarboxamide, 2,3-bis(2-pyridyl)pyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinol, 2-chloropyrimidine, 5-bromopyrimidine, 2,4,6-trichloropyrimidine, 2,4,5,6-tetrachloropyrimidine, 2,4-dichloro-6-methylpyrimidine, 2,4-dichloro-6-methylpyrimidine, 6-chloro-2,4-dimethoxypyrimidine, 2-hydroxypyrimidine, 4,6-dimethyl-2-hydroxypyrimidine, 2,4-dimethyl-6-hydroxypyrimidine, 4,6-dimethyl-2-hydroxypyrimidine, 2-isopropyl-6-methyl-4-pyrimidinol, 4,6-dihydroxypyrimidine, 2,4-dihydroxy-5,6-dimethylpyrimidine, 2,4-dihydroxy-6-methylpyrimidine, 4,6-dihydroxy-2-methylpyrimidine, 2,4,5-trihydroxypyrimidine, 4,6-dichloro-5-nitropyrimidine, 4,6-dihydroxy-5-nitropyrimidine, 2,4-dihydroxypyrimidine-5-carboxylic acid, 1,3,5-triazine, 2-chloro-4,6-dimethoxy-1,3, 5-triazine, 2,4,6-triphenoxy-1,3,5-triazine, 2,4,6-triphenyl-1,3,5-triazine, 2,4,6-tri(2-pyridyl)-1,3,5-triazine, (−)-cotinine (1-methyl-5-(3-pyridyl)-2-pyrrolidinone), quinoline, 2,2'-biquinoline, quinaldine, lepidine, 6-methylquinoline, 7-methylquinoline, 8-methylquinoline, 2,4-dimethylquinoline, 2,6-dimethylquinoline, 2,7-dimethylquinoline, 2,8-dimethylquinoline, 2-phenylquinoline, 7,8-benzoquinoline, 2-chloroquinoline, alpha,alpha,alpha-tribromoquinaldine, 4-chloroquinoline, 6-chloroquinoline, 4-chloro-7-(trifluoromethyl)quinoline, 4-chloro-8-(trifluoromethyl)quinoline, 4-chloro-2,8-bis(trifluoromethyl)quinoline, 4-chloroquinaldine, 7-chloroquinaldine, 2-chlorolepidine, 3-bromoquinoline, 4,7-dichloroquinoline, 4-bromo-2,8-bis(trifluoromethyl)quinoline, 6-methoxyquinoline, 6-methoxyquinaldine, 2-hydroxy-4-methylquinoline, 4-hydroxyquinoline, 7-chloro-4-hydroxyquinoline, 8-(trifluoromethyl)-4-quinolinol, 2,4-quinolinediol, 2-hydroxyquinoline, 5-hydroxyquinoline, 6-hydroxyquinoline, 8-hydroxyquinoline, 8-hydroxyquinaldine, 4-hydroxy-2-methylquinoline, 7-(trifluoromethyl)-4-quinolinol, 2,8-bis(trifluoromethyl)-4-quinolinol, 5-chloro-8-hydroxyquinoline, 5,7-dichloro-8-hydroxyquinoline, 5,7-dibromo-8-hydroxyquinoline, 5,7-dibromo-2-methyl-8-quinolinol, 5,7-dichloro-2-methyl-8-quinolinol, 5-nitroquinoline, 6-nitroquinoline, 8-nitroquinoline, 8-nitroquinaldine, 8-methyl-5-nitroquinoline, 8-hydroxy-5-nitroquinoline, 6-methoxy-8-nitroquinoline, quinaldic acid, 3-quinolinecarboxylic acid, 4-quinolinecarboxylic acid, 8-quinolinecarboxylic acid, 1,2,3,4-tetrahydro-9-acridinecarboxylic acid, 4-methoxy-2-quinolinecarboxylic acid, 4-hydroxyquinoline-2-carboxylic acid, 4-hydroxy-7-trifluoromethyl-3-quinolinecarboxylic acid, 4,8- dihydroxyquinoline-2-carboxylic acid, 2-phenyl-4-quinolinecarboxylic acid, ethyl 4-hydroxy-7-trifluoromethyl-3-quinolinecarboxylate, methyl 2-phenyl-4-quinolinecarboxylate, 2-quinolinecarbonitrile, 3-quinolinecarbonitrile, 2,8-bis(trifluoromethyl)-4-quinolinecarbonitrile, 5,6,7,8-tetrahydroisoquinoline, 3-methyl-5,6,7,8-tetrahydroquinoline, 1,2,3,4,5,6,7,8-octahydroacridine, acridine, 5-triazolo(4,3-A)quinoline, 6,9-dichloro-2-methoxyacridine, 9-hydroxy-4-methoxyacridine, 9-acridinecarboxylic acid, 4,9-acridinedicarboxylic acid, 1,3-dihydroxy-9-acridinecarboxylic acid, phenyl 9-acridinecarboxylate, isoquinoline, 3-methylisoquinoline, 4-bromoisoquinoline, 1,3-dichloroisoquinoline, papaverine, isocarbostyril, 3-hydroxyisoquinoline, 5-hydroxyisoquinoline, 1,5-isoquinolinediol, 5-nitroisoquinoline, 1-isoquinolinyl phenyl ketone, protopapaverine, 1-isoquinolinecarboxylic acid, 3-isoquinolinecarboxylic acid, methyl 3-isoquinolinecarboxylate, 1-isoquinolinecarbonitrile, 3-isoquinolinecarbonitrile, benz[g]isoquinoline-5,10-dione, 3,8-dinitro-6-phenylphenanthridine, cinnoline, phenanthridine, 3,8-diamino-6-phenylphenanthridine, benzo[c]cinnoline, cinnoline-4-carboxylic acid, phthalazine, 1,4-dichlorophthalazine, 1(2H)-phthalazinone, quinazoline, 4-hydroxyquinazoline, 2-methyl-4(3H)-quinazolinone, quinoxaline, 2-methylquinoxaline, 5-methylquinoxaline, 2,3-dimethylquinoxaline, ethyl 2-quinoxalinecarboxylate, 2,3-diphenylquinoxaline, 6,7-dimethyl-2,3-di-(2-pyridyl) quinoxaline, phenazine, 2,3-dichloroquinoxaline, 2,3,6,7-tetrachloroquinoxaline, 2,3-bis(bromomethyl)-quinoxaline, 2-quinoxalinol, 3-methyl-2-quinoxalinol, 2,3-dihydroxyquinoxaline, 2-quinoxalinecarboxylic acid, 3-hydroxy-2-quinoxalinecarboxylic acid, 4-hydroxy-7-methyl-1,8-naphthyridine-3-carboxylic acid, 2,2'-pyridyl, 2,2'-dipyridyl, 4,4'-dimethyl-2,2'-dipyridyl, 4,4'-diphenyl-2,2'dipyridyl, 6-chloro-2,2'-bipyridine, 2,4'-dipyridyl, 4,4'-dipyridyl, di-2-pyridyl ketone, 2,2':6',2"-terpyridine, 1,7-phenanthroline, 1,10-phenanthroline, 4,7-phenanthroline, phenazine, 4-methyl-1,10-phenanthroline, 5-methyl-1,10-phenanthroline, neocuproine, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,9-dimethyl-4,7-diphenyl-1,10-phenanthroline, 5-chloro-1,10-phenanthroline, 6,7-dihydro-5,8-dimethyldibenzo-(1-10)-phenanthroline, 5-nitro-1,10-phenylanthroline, 7-oxo-7-H-benzo[e]perimidine-4-carboxylic acid, lumazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-phenylpyrazole, 3-methyl-1-phenylpyrazole, 3-methyl-1-phenyl-2-pyrazolin-5-one, 4-benzoyl-3-methyl-1-phenyl-2-pyrazolin-5-one, 4-(3-methyl-5-oxo-2-pyrazolin-1-yl)-benzoic acid, 3,5-dimethylpyrazole-1-carboxamide, 1-nitropyrazole, oxazole, 2,5-diphenyloxazole, 2,4,5-trimethyloxazole, 1,4-bis(5-phenyloxazol-2-yl)-benzene, 1,4-bis(4-methyl-5-phenyloxazol-2-yl)benzene, 5-phenyl-2-(4-pyridyl)-oxazole, 2-(4-biphenylyl)-5-phenyloxazole, 2,5-bis(4-biphenylyl)oxazole, 2-methyl-4,5-diphenyloxazole, 9,10-dihydro-2-methyl-4H-benzo(5,6)cyclohept(1,2)-oxazol-4-ol, N1-(4,5-dimethyloxazol-2-yl)-sulfanilamide, 2,5-diphenyl-1,3,4-oxadiazole, 2-(4-biphenylyl)-5-phenyl-1,3,4-oxadiazole, 2-(4-biphenylyl)-5-(4-tert-butylphenyl)-1,3,4-oxadiazole, 2,5-bis(4-aminophenyl)-1,3,4-oxadiazole, 2,5-bis(4-diethylaminophenyl)-1,3,4-oxadiazole, benzoxazole, 2-methylbenzoxazole, 2,5-dimethylbenzoxazole, 2-methyl-5-phenylbenzoxazole, 2-(4-biphenylyl)-6-phenylbenzoxazole, 2-chlorobenzoxazole, 2-phenylbenzoxazole, 2-(2'-hydroxyphenyl)-benzoxazole, 2,4,4-trimethyl-2-oxazoline, isoxazole, 1,2-benzisoxazole, 3,5-dimethylisoxazole, 5-methylisoxazole, 3,5-dimethylisoxazole, 4-(chloromethyl)-3,5-dimethylisoxazole, 3,5-dimethyl-4-nitroisoxazole, 5-methyl-3-phenylisoxazole-4-carboxylic acid, N,5-dimethyl-3-phenylisoxazole-4-carboxamide, N,5-dimethyl-3-(4-fluorophenyl)-4-isoxazolecarboxamide, 2,5-diphenyloxazole, 2,6-bis[(4S)-isopropyl-2-oxazolin-2-yl] pyridine, 1,5-pentamethylenetetrazole, 1,2-dimethylimidazole, 1-methylimidazole, 1-ethylimidazole, 1-propylimidazole, 1-butylimidazole, 1-phenylimidazole, 1-benzylimidazole, 1-benzyl-2-1-(2,3,4,6-tetrafluorophenyl)-imidazole, 1-(2-chloroethyl)-2-methyl-5-nitroimidazole, metronidazole, 2-methyl-4-nitro-1-imidazolepropionic acid, 2-methyl-4-nitro-1-imidazolepropionitrile, 1,5-dicyclohexylimidazole, 5-chloro-1-methylimidazole, 5-chloro-1-ethyl-2-methylimidazole, 4-(imidazol-1-yl)phenol, imidazo(1,2-A) pyridine, anthranil, 2,3,3-trimethylindolenine, caffeine and 6-chloropurine riboside.

Applicable Solvents for General Method for MTO/accelerant-catalyzed epoxidation of an olefin The following solvents are commercially available from Aldrich and are highly applicable in use with the above general method for MTO/accelerant-catalyzed epoxidation of an olefin as disclosed vida supra. The applicable solvents and solvent mixtures used in the concentration range outlined in the general method are as follows: nitromethane, nitroethane, methylene chloride, chloroform, carbon tetrachloride, freon-12, chloroethane, 1,2-dichloroethane, pentachloroethane, 1-chloropropane, 1-chlorobutane, chlorobenzene, dichlorobenzene, trichlorobenzene, fluorobenzene, difluorobenzene, trifluorobenzene, trifluoromethylbenzene, fluoroethane, acetonitrile, acetone, benzene, toluene, 2-fluorotoluene, 4-fluorotoluene, nitrobenzene, o-xylene, m-xylene, p-xylene, mesitylene, 1,2,3-trimethyl benzene, 1,2,4-trimethyl benzene, methanol, ethanol, propanol, isopropanol, butanol, t-butanol, ethyleneglycol, diethylether, dioxane, tetrahydrofuran, and supercritical $CO_2$.

The following mixtures in any ratio combination can also be used: nitromethane/t-butanol, nitromethane/n-propanol, nitromethane/i-propanol, nitromethane/ethanol, nitromethane/methanol, methylene chloride/t-butanol, methylene chloride/n-propanol, methylene chloride/i-propanol, methylene chloride/ethanol, methylene chloride/methanol, chloroform/t-butanol, chloroform/n-propanol, chloroform/i-propanol, chloroform/ethanol, and chloroform/methanol.

Applicable Olefin Substrates for General Method for MTO/accelerant-catalyzed epoxidation of an olefin The general method is compatible with most non-cyclic olefins which have mono, di, tri and tetra substitutions (FIG. 3, equation 1). A representative but nonexhaustive example of substitutions on a non-cyclic olefin are included as follows, wherein $R_1$, $R_2$, $R_3$ and $R_4$ of said olefin, FIG. 3, equation 1, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), $SO_3H$ (sulfonic acid), $SO_2O$—$C_1$–$C_6$ (sulfonic acid esters), $SO_2NH$—$C_1$–$C_6$ (sulfonamides), CN, F, Cl, Br, OH, and $C_1$–$C_6$ alkyl containing the following substitutions: F, Cl, Br, CN, OH, COOH, C(O)OR (esters, lactones), C(O)N (amide, lactam), SO$_3$H (sulfonic acid), SO$_2$O—C$_1$–C$_6$ (sulfonic acid esters), SO$_2$NH—C$_1$–C$_6$ (sulfonamides), CN, F, Cl, OR, NRR', etc.

The process is also compatable with endocyclic olefins which have mono and di substitutions (FIG. 3, equation 2). A representative but nonexhaustive example of substitutions on an endocyclic olefin are included as follows, wherein R$_1$ and R$_2$ of said olefin, FIG. 3, equation 2, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), SO$_3$H (sulfonic acid), SO$_2$O—C$_1$–C$_6$ (sulfonic acid esters), SO$_2$NH—C$_1$–C$_6$ (sulfonamides), CN, F, Cl, Br, OH, and C$_1$–C$_6$ alkyl containing the following substitutions: F, Cl, Br, CN, OH, COOH, C(O)OR (esters, lactones), C(O)N (amide, lactam), SO$_3$H (sulfonic acid), SO$_2$O—C$_1$–C$_6$ (sulfonic acid esters), SO$_2$NH—C$_1$–C$_6$ (sulfonamides), CN, F, Cl, OR, NRR', etc. The variable "x" represents a range of rings including C$_4$H$_4$ to C$_8$H$_{16}$ (cyclobutane to cyclodecene-derivatives [cis and trans]), etc.

Exocyclic olefins which have mono and di substitutions are also compatible with the general methodology disclosed vida supra (FIG. 3, equation 3). A representative but nonexhaustive example of substitutions on an endocyclic olefin are included as follows, wherein R$_1$ and R$_2$ of said olefin, FIG. 3, equation 3, are selected from the group consisting of hydrogen, methyl, ethyl, propyl, isopropyl, cyclopropyl, butyl, isobutyl, sec-butyl, tert-butyl, cyclobutyl, methylcyclopropyl, pentyl, hexyl, heptyl, octyl, nonyl, decyl, benzyl, nitrobenzyl, COOH, C(O)OR (esters, lactones), C(O)N (amide, lactam), SO$_3$H (sulfonic acid), SO$_2$O—C$_1$–C$_6$ (sulfonic acid esters), SO$_2$NH—C$_1$–C$_6$ (sulfonamides), CN, F, Cl, Br, OH, and C$_1$–C$_6$ alkyl containing the following substitutions: F, Cl, Br, CN, OH, COOH, C(O)OR (esters, lactones), C(O)N (amide, lactam), SO$_3$H (sulfonic acid), SO$_2$O—C$_1$–C$_6$ (sulfonic acid esters), SO$_2$NH—C$_1$–C$_6$ (sulfonamides), CN, F, Cl, OR, NRR', etc. The variable "x" represents a range of rings including C$_4$H$_4$ to C$_8$H$_{16}$ (cyclobutane to cyclodecene-derivatives [cis and trans]), etc.

Lastly, the process is also compatable with dienes, trienes, and polyolefines including conjugated and isolated double bond compounds like allenes. Furthermore, double bonds in natural products and drug precursors like terpenes, e.g. pinene derivatives, steroids, e.g. cholesterol and cholesterol acetate, and unsaturated fatty acids and their esters are equally accessible for conversion to epoxides using the process. Examples for the fatty acids are palmitoleic acid (cis-9-hexadienoic acid) and its esters (methyl, ethyl, propyl-isomers, butyl-isomers, glyceryl etc.), oleic acid (cis-9-octadecenoic acid) and its esters (methyl, ethyl, propyl-isomers, butyl-isomers, glyceryl etc.), ricinoleic acid (cis-12-hydroxy-octadecenoic acid) and its esters (methyl, ethyl, propyl-isomers, butyl-isomers, glyceryl etc.), linoleic acid (cis,cis-9,12-octadecadienoic acid) and its esters (methyl, ethyl, propyl-isomers, butyl-isomers, glyceryl etc.), and linolenic acid (cis,cis,cis-9,12,15-octadecatrienoic acid) and its esters (methyl, ethyl, propyl-isomers, butyl-isomers, glyceryl etc.). Raw materials such as olive oil (~80% oleic acid), corn oil (~60% linoleic acid), linseed oil (~55% linolenic acid), castor oil hydrolyzate (~80% ricinoleic acid) can also be used in place of the pure acids.

Applicable Organorhenium oxides for General Method for MTO/accelerant-catalyzed epoxidation of an olefin Only MTO is commercially available from Aldrich, the others are synthesized as disclosed vida infra and are highly applicable in use with the above general method for MTO/accelerant-catalyzed epoxidation of an olefin as disclosed vida supra. The applicable organorhenium oxides used in the concentration range outlined in the general method are as follows: the organorhenium oxide is represented by the formula R$_1$ReO$_3$ wherein R$_1$=methyl, ethyl, n-propyl, n-butyl, n-pentyl, n-hexyl, heptyl, octyl, isopropyl, t-butyl, adamantyl, phenyl, benzyl, cyclopropyl, cyclobutyl, cyclopentyl, cyclohexyl, 1-bicyclo(2.2.2)octanyl, 1-bicyclo(2.2.1)heptanyl, 1-bicyclo(2.1.1)hexanyl, 1-bicyclo(1.1.1)pentanyl, 1-bicyclo(3.2.1)octanyl, 1-bicyclo(1.1.3)heptanyl, cubyl, sec-butyl, neo-pentyl, 3-methylbutyl, (S)-2-methylbutyl, (R,S)-2-ethylhexyl, trimethylsilylmethyl, γ-diethylamino-n-propyl, tolyl, 2,6-dimethylphenyl, 2,4,6-trimethylphenyl, pentafluorophenyl, 4-hydroxy-2,6-dimethylphenyl, 4-trimethylsiloxy-2,6-dimethylphenyl, ethynyl, phenylethynyl, methylallyl, methylvinyl, 2,4-pentadienyl, and ethylacetyl.

Synthesis of Organorhenium oxides

Compounds R⁻ReO$_3$ wherein R=Methyl, Ethyl, n-propyl, n-butyl, sec-butyl, n-pentyl, neo-pentyl, n-hexyl, 3-methylbutyl, (S)-2-methylbutyl, (R,S)-2-ethylhexyl, cyclopropyl, trimethylsilylmethyl, γ-diethylamino-n-propyl, phenyl, tolyl, (2,6-dimethylphenyl), (2,4,6-trimethylphenyl), pentafluorophenyl, (4-hydroxy-2,6-dimethylphenyl), (4-trimethylsiloxy-2,6-dimethylphenyl), ethynyl, phenylethynyl, methylallyl, methylvinyl, (2,4-pentadienyl), benzyl, ethylacetyl, ethyl(η-C$_5$H$_5$), (η-C$_5$Me$_5$), (η-C$_5$Et$_5$) are synthesized according to procedures described vida infra which are well known in the art wherein representative references for the synthesis of organorhenium oxides include Herrmann et al. *Chem. Ber.* 1993, 126, 45; Herrmann et al. *Inorg. Chem.* 1992, 31, 4431; Herrmann et al. *Angew. Chem. Int. Ed. Engl.* 1991, 30, 185; C. de Meric de Bellefon et al. *Organometallics* 1992, 11, 1072; Herrmann et al. *J. Mol. Catal.* 1994, 86, 243; Herrmann et al. *J. Organomet. Chem.* 1995, 495, 209; Herrmann et al. *J. Organomet. Chem.* 1994, 481, 227; Herrmann et al. *Organometallics* 1994, 13, 1601.

Procedure A for the preparation of organorhenium oxides

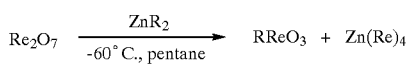

A solution of ZnR$_2$ (1.00 mmol; R group defined vida supra; commercially available substrate) in 10 mL n-pentane is added slowly at −60° C. to a stirred solution of 1.00 g (2.06 mmol) Re$_2$O$_7$ in 15 mL THF. After 40–60 minutes, stirring the solvent is removed in vacuo at −55° C. The dark brown residue is extracted with 35 mL cold n-pentane. The solvent of the extract is further removed until a volume of 1–2 mL is reached. This residue is allowed to stay for 12 h at −78° C. Many derivatives crystallize out. Yield: 20–50%.

Alternative: instead of pentane THF is preferred: A solution of sublimed Re$_2$O$_7$ (489 mg, 1 mmol) in 15 mL of THF (<1 ppm H$_2$O) was treated at dry-ice temperature with exactly 0.5 mmol of ZnR$_2$ (1M solution in THF). The colorless stirred solution was warmed to −5° C. (R=C$_2$H$_5$), −30° C. (R=i-C$_4$H$_9$), or 20° C. (R=CH$_2$Si(CH$_3$)$_3$, C$_6$H$_5$). The THF was evaporated in vacuo, and the residue was extracted with cold n-pentane. The yellow extract filtered through a cannula and concentrated to about 10 mL at −30° C. under vacuum. Cooling the solution to dry-ice temperature afforded colorless crystals, which were dried under high vacuum at −30° C. Yield: 60–70%.

Procedure B for the preparation of organorhenium oxides

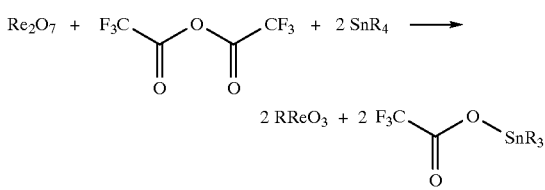

A solution of $Re_2O_7$ (5.0 g, 10.30 mmol) in 60 mL of acetonitrile is treated with 2.45 g of perfluoroglutaric anhydride (10.30 mmol (instead of trifluoroacetic anhydride, perfluoroglutaric anhydride can also be taken)) at room temperature. After a few minutes, 3.85 g of $SnMe_4$ (20.60 mmol) is added and the mixture is stirred for 2.5 h at room temperature. Acetonitrile is the carefully removed in an oil-pump vacuum at room temperature, and MTO is consecutively sublimed as colorless crystals at 65° C./$10^{-3}$ mmHg; isolated yield 4.26 g (83%).

Procedure B for the preparation of organorhenium oxides

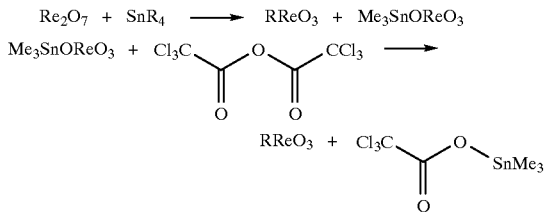

A solution of $Re_2O_7$ (5 g, 10.3 mmol) and tetramethyltin (1.6 mL, 11.6 mmol) in 70 mL of dry THF was heated in a 240 mL Schlenk flask at 67° C. (reflux) for 4 hours. The solvent was subsequently removed in an oil-pump vacuum at 25° C. This step has to take care that no MTO is distilled off with the solvent. The desired product was sublimed from the grey-white residue at 60–80° C./$10^{-3}$ mmHg; i onto a cold finger (0° C.) as colorless fine crystals. Isolated yield: 2.4 g (93%).

2) The route described yields stannylperrhenate $Me_3SnOReO_3$ as the by-product. It constitutes the sublimation residue and is recrystallized from acetonitrile (4.0 g, 94%). This material can be utilized for the preparation of MTO as follows: A solution of $Me_3SnOReO_3$ (4 g, 9.7 mmol) and trichloroacetic anhydride (1.77 mL, 9.7 mmol) in 60 mL dry acetonitrile was stirred at 25° C. for 4 hours. Tetramethyltin (1.5 mL, 10.80 mmol) was the added to the pale-green solution which was then stirred over night at 25° C. The solvent was then carefully removed in an oil-pump vacuum at 25° C. The crude product was consecutively sublimed at 90–100° C./$10^{-3}$ mmHg on a cold finger (0° C.), thus resulting in dark-red crystals. The sublimed material was stirred over night in n-pentane. The then yellow solution containing the by-products was separated by filtration through a syringe. The white residue was washed with cold n-pentane (0° C.) and was sublimed once again, as described above. This procedure was repeated twice to finally yield 2.00 g (83%) of pure MTO. The total yield of MTO, based upon rhenium, amounts to 86% from the combined steps 1) and 2). A scale-up of this procedure to synthesize 25 g (0.10 mol) of MTO in one run is possible by using appropriate sizes of Schlenk and sublimation flasks.

The $CD_3$ derivative $CD_3ReO_3$ is synthesized from $Re_2O_7$ and $(n-C_4H_9)_3SnCD_3$ in dry acetonitrile (80% yield).

Preparation of dialkylzinc compounds used in the above preparations of organorhenium oxides Procedures adapted from review articles in Hauben-Weyl et al. Methoden der Organischen Chemie, 4. Aufl., Bd XIII/2a); Organozinc reagents in organic synthesis, E. Erdik (ed.), CRC press, 1996. Dimethylzinc and diethylzinc a commercially available. Dialkylzinc compounds can be prepared using common transmetallation procedures (or other methods):

$2\ RMgBr+ZnCl_2 \rightarrow ZnR_2+MgBr_2+MgCl_2$ $2\ RLi+ZnCl_2 \rightarrow ZnR_2+2\ LiCl$ Dicyclopropylzinc, dicyclobutylzinc, dicyclopentylzinc, diyclohexylzinc has been prepared by Thiele et al *J. Organomet. Chem.* 1968, 14, 13 as follows, wherein:

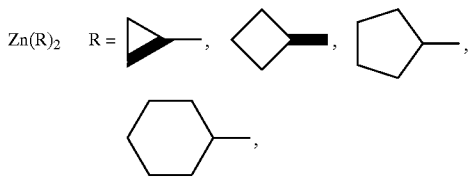

additionally, the dialkyl zinc of cyclopentyl, cyclohexyl, 1-bicyclo(2.2.2)octanyl, 1-bicyclo(2.2.1)heptanyl, 1-bicyclo(2.1.1)hexanyl, 1-bicyclo(1.1.1)pentanyl, 1-bicyclo(3.2.1)octanyl, 1-bicyclo(1.1.3)heptanyl and cubyl are equally accessable from the lithium derivative (RLi) as precursors to the corresponding compounds which are substrates for the synthesis of the corresponding Rhenium compounds.

An etherial solution of cyclopropylmagnesiumbromide is prepared by adding 24.2 g Mg to 121 g (1 mole) cyclopropylbromide. This solution contains only ~35% active Grignard compound. To this is added an etherial solution of 23.6 g (0.17 mole) of zincchloride. After filtration the most of the ether is removed, 200 mL heptane is added following a destillation in vacuo. Yield: ~8 g (32%); $Bp_4$: 60° C.

Preparation of dicyclobutylzinc: Lit.: Thiele et al. *J. Organomet. Chem.* 1968, 14, 13.Cyclobutylbromide (67 g, 0.5 mole) is added to a suspension of 12 g Mg in diethylether to give a solution of cyclobutylmagnesiumbromide. To this solution containing ~55–60% active Grignard compound is added an etherial solution of 18.5 g (0.14 mole) zincchloride. After reaction completion and seperation of the precipitated magnesium salts, half of the solvent of the bright yellow solution is removed in vacuo, and the same volume of n-hexane is added and a further filtration is done followed by destillation. Pure dicyclobutylzinc is obtained at a bath temperature of 80–100° C. (0.8 mm at 42–44° C.). Yield: 7 g (28%).

Preparation of dicyclohexylzinc Lit.: Thiele et al. *J. Organomet. Chem.* 1968, 14, 13; 30 g activated magnesium turnings, 145 g cyclohexylchloride (1.25 mole) and 300 mL diethylether are added together to give a cyclohexylmagnesiumchloride solution. This mixture contains ~70% active Grignard compound. To this stirred solution is added a solution of 54 g (0.4 mole) anhydrous zincchloride in 150 mL diethylether. After stirring for 1 h, 200 mL xylene is added and the magnesium salts are filtered off and discarded. Afterwards the ether and most of the xylene is removed in vacuo. A second filtration is done followed by a destination at high vacuum.

At $10^{-4}$ mm (after solvent remainders) and at 40–50° C. first higher boiling hydrocarbons (bicyclohexyl!) are obtained. The subsequently at 64–66° C. destilled pure dicyclohexylzinc becomes solid in the trap (mp. 55° C.) and is transfered to a Schlenk flask by careful heating. Yield: 20 g (18%).

An alternative way of preparing dicyclopropylzinc derivatives is described by Lehmkuhl et al. *J. Organomet. Chem.* 1981, 221, 123).

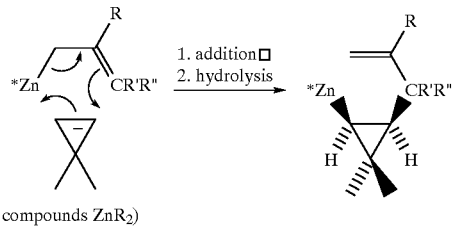
(*all compounds ZnR$_2$)

General procedures for additions of bis(alk-2-enyl)zinc compounds on 3,3-dimethylcyclopropene: In a 250 mL three neck flask which was equipped with a stirrer and with a reflux condenser (cooled to −30° C.) and a dropping funnel was added 30–200 mmol bis(alk-2-enyl)zinc compound (a: R, R', R"=H or R=Me, R', R"=H, or R, R"=H, R'=Me or R=H, R', R"=Me) in 20–80 mL diethylether. To this is added dropwise an equivalent amount (60–400 mmole) of 3,3-dimethylcyclopropene in 20–40 mL ether. The reaction temperature is allowed to come to ambient temperature and kept there for 12 hours. Solvent and non-reacted 3,3-dimethylcyclopropene is removed at 20° C./1 Torr and the residue is destilled at 80–120° C. (bath)/0.0001 Torr.

Bis(1-norbornyl)zinc, bis(2-norbornylzinc), bis(7-norbornylzinc), and bis(1-camphenyl)zinc have also been prepared by Thiele et al as follows:

Preparation of bis(2-norbornylzinc). Lit.: Thiele et al. *Z. Anorg. Allg. Chem. Chem.* 1981, 483, 145. To a suspension of 4 g 1-norbonyllithium in 100 mL n-pentane is added dropwise a solution of 2.6 g zincchloride in 150 mL diethylether (keep the speed of addition in such a way that the solution is boiling smoothly). This solution is stirred for 1 h, the precipitate is filtered and washed with little n-pentane and discarded. The solvent of the combined filtrates is completely removed in vacuo. The residue is solved in n-pentane, and remaining LiCl is seperated. The solution is then cooled to −78° C. The precipitated crystalls are filtered at low temperature and dried in vacuo. Yield: 3.7 g (72%).

Preparation of bis(1-camphenyl)zinc: Thiele et al. *Anorg. Allg. Chem. Chem.* 1988, 561, 73. To a stirred suspension of 18.4 g 1-camphenyllithium in 250 mL n-pentane is added dropwise a solution of 9 g zincchloride in 300 mL diethylether at room temperature (keep the speed of addition in such a way that the solution is boiling smoothly). This reaction mixture is stirred for 3 h and is subsequently allowed to stand overnight. The precipitated LiCl is filtered off and the solvent of the filtrate is completely removed. The residue is solved in n-pentane and remaining LiCl is separated. The solution is the cooled to −78° C. The precipitated crystalls are filtered at low temperature and dried in vacuo. Yield: 12.5 g (60%).

Figure 1:
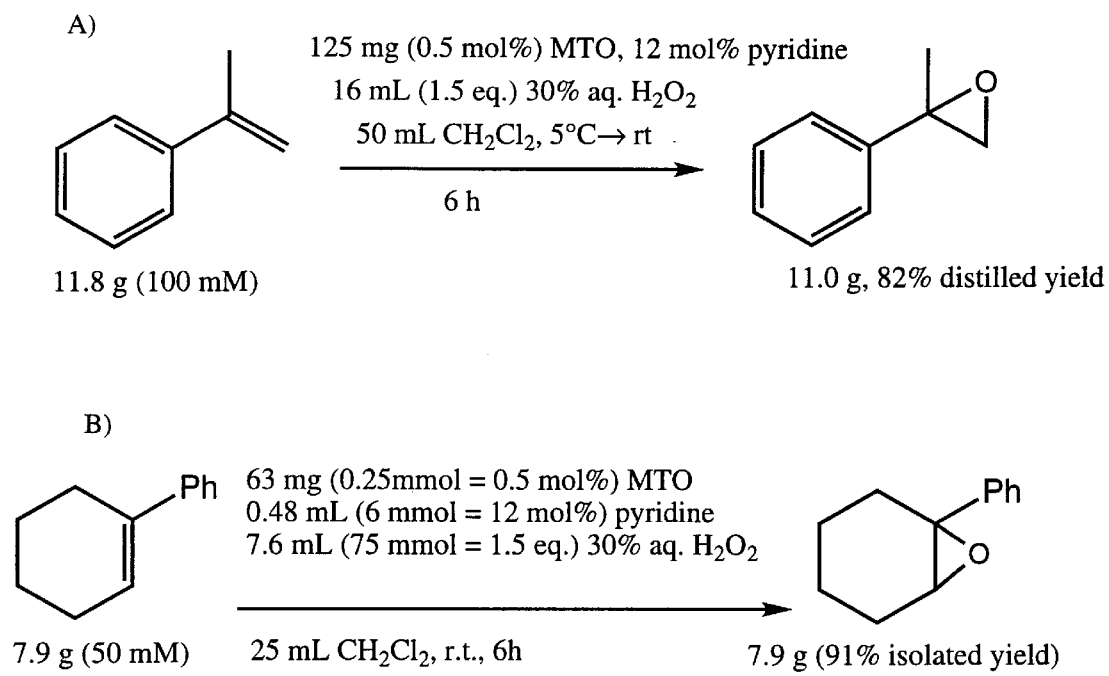
FIG. 1 illustrates the following.

Epoxidation of 1-phenyl-cyclohexene as illustrated in FIG. 1

In a 50 mL flask equipped with a magnetic stirrer, 7.9 g (50 mmol) of 1-phenylcyclohexene and 63 mg (0.25 mmol, 0.5 mol %) of MTO are dissolved in 1.5 Molar CH$_2$Cl$_2$ and to this solution is added 0.48 mL (6 mmol, 12 mol %) of pyridine followed by 7.6 mL (75 mmol; 1.5 equivalents) of 30% aqueous H$_2$O$_2$ added dropwise from a syringe (circa 5–10 minutes). During the H$_2$O$_2$-addition the temperature is kept at 20–25° C. by applying an external cooling bath. The reaction is complete after 6 h and the aqueous phase is seperated and discarded. The remaining H$_2$O$_2$ in the yellow organic phase is decomposed to O$_2$ and H$_2$O by stirring with a catalytic amount of MnO$_2$ (circa 10 mg). After the yellow color has completely disappeared the mixture is dried over Na$_2$SO$_4$, concentrated, and purified by filtration through a short column of silica gel which has been deactivated with NEt$_3$. The column is washed with hexane/CH$_2$Cl$_2$ and concentration of the eluate affords 7.9 g (91%) of 1-phenyl-1,2-epoxycyclohexane as a colorless oil.

Epoxidation of 1-propene wherein substrate is shown in entry 1, FIG. 5

In a 5 mL scintillation vial equipped with a magnetic stirrer, (2 mmol) of 1-propene and (10 μmol, 0.5 mol %) of MTO (methyl-rhenium oxide) are dissolved in 1.5 Molar CH$_2$Cl$_2$. To this solution is added (228 μmol, 12 mol %) of pyridine followed by (3 mmol, 1.5 equivalents) of 30% aqueous H$_2$O$_2$ added at once from a syringe. The reaction is stopped after it is determined finished by following by TLC or gas chromatography (looking for overall disappearance of starting material and appearance of product) and the remaining H$_2$O$_2$ is decomposed to O$_2$ and H$_2$O by stirring with a catalytic amount of MnO$_2$ (ca 0.010 equivalents). After the yellow color has disappeared the mixture is dried over Na$_2$SO$_4$, concentrated, and purified by filtration through a small column of silica gel which has been deactivated with NEt$_3$. The column is washed with Et$_2$O and concentration of the eluate affords the title epoxide wherein the yield is reported as illustrated in the figure under the conversion (%) column.

Epoxidation of 1-decene wherein substrate is shown in entry 2, FIG. 5

In a 5 mL scintillation vial equipped with a magnetic stirrer, (2 mmol) of 1-decene and (10 μmol, 0.5 mol %) of MTO (methyl-rhenium oxide) are dissolved in 1.5 Molar CH$_2$Cl$_2$. To this solution is added (228 μmol, 12 mol %) of pyridine followed by (3 mmol, 1.5 equivalents) of 30% aqueous H$_2$O$_2$ added at once from a syringe. The reaction is stopped after it is determined finished by following by TLC or gas chromatography (looking for overall disappearance of starting material and appearance of product) and the remaining H$_2$O$_2$ is decomposed to O$_2$ and H$_2$O by stirring with a catalytic amount of MnO$_2$ (ca 0.010 equivalents). After the yellow color has disappeared the mixture is dried over Na$_2$SO$_4$, concentrated, and purified by filtration through a small column of silica gel which has been deactivated with NEt$_3$. The column is washed with Et$_2$O and concentration of the eluate affords the title epoxide wherein the yield is reported as illustrated in the figure under the conversion (%) column.

Epoxidation of styrene wherein substrate is shown in entry 3, FIG. 5

In a 5 mL scintillation vial equipped with a magnetic stirrer, (2 mmol) of styrene and (10 μmol, 0.5 mol %) of MTO (methyl-rhenium oxide) are dissolved in 1.5 Molar CH$_2$Cl$_2$. To this solution is added (228 μmol, 12 mol %) of pyridine followed by (3 mmol, 1.5 equivalents) of 30% aqueous H$_2$O$_2$ added at once from a syringe. The reaction is stopped after it is determined finished by following by TLC or gas chromatography (looking for overall disappearance of starting material and appearance of product) and the remaining H$_2$O$_2$ is decomposed to O$_2$ and H$_2$O by stirring with a catalytic amount of MnO$_2$ (ca 0.010 equivalents). After the yellow color has disappeared the mixture is dried over Na$_2$SO$_4$, concentrated, and purified by filtration through a small column of silica gel which has been deactivated with NEt₃. The column is washed with Et₂O and concentration of the eluate affords the title epoxide wherein the yield is reported as illustrated in the figure under the conversion (%) column.

Epoxidation of α-methylstyrene wherein substrate is shown in entry 4, FIG. 5

In a 100 mL flask equipped with a magnetic stirrer, 11.8 g (100 mmol) of α-methylstyrene and 125 mg (0.5 mmol, 0.5 mol %) MTO are dissolved in 50 mL $CH_2Cl_2$. To this solution is added 0.96 mL (12 mmol, 12 mol %) of pyridine followed by 16 mL (1.5 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 6 h and the aqueous phase is separated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified by distillation. Isolated yield: 82%.

Epoxidation of methylenecyclohexane wherein substrate is shown in entry 5, FIG. 5

In a 50 mL flask equipped with a magnetic stirrer, 4.6 g (47.8 mmol) of methylenecyclohexane and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with NEt₃. The column is washed with Et₂O and concentration of the eluate affords the title epoxide wherein the yield is reported as illustrated in the figure under the conversion (%) column.

Epoxidation of 1,1-diphenyl-ethylene wherein substrate is shown in entry 6, FIG. 5

In a 5 mL scintillation vial equipped with a magnetic stirrer, (2 mmol) of 1,1-diphenyl-ethylene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with NEt₃. The column is washed with Et₂O and concentration of the eluate affords the title epoxide wherein the yield is reported as illustrated in the figure under the conversion (%) column.

Epoxidation of trans-4-octene wherein substrate is shown in entry 7, FIG. 6

In a 5 mL scintillation vial equipped with a magnetic stirrer, (2 mmol) of trans-4-octene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with NEt₃. The column is washed with Et₂O and concentration of the eluate affords the title epoxide wherein the yield is reported as illustrated in the figure under the conversion (%) column.

Epoxidation of trans-β-methylstyrene wherein substrate is shown in entry 8, FIG. 6

In a 5 mL scintillation vial equipped with a magnetic stirrer, (2 mmol) of trans-β-methylstyrene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with NEt₃. The column is washed with Et₂O and concentration of the eluate affords the title epoxide wherein the yield is reported as illustrated in the figure under the conversion (%) column.

Epoxidation of trans-stilbene wherein substrate is shown in entry 9, FIG. 6

In a 5 mL scintillation vial equipped with a magnetic stirrer, (2 mmol) of trans-stilbene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with NEt₃. The column is washed with Et₂O and concentration of the eluate affords the title epoxide wherein the yield is reported as illustrated in the figure under the conversion (%) column.

Epoxidation of cis-4-octene wherein substrate is shown in entry 10, FIG. 6

In a 50 mL flask equipped with a magnetic stirrer, 5.6 g (50 mmol) of cis-4-octene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of cis-β-methylstyrene wherein substrate is shown in entry 11, FIG. 6

In a 5 mL scintillation vial equipped with a magnetic stirrer, (2 mmol) of cis-β-methylstyrene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of cis-stilbene wherein substrate is shown in entry 12, FIG. 6

In a 5 mL scintillation vial equipped with a magnetic stirrer, (2 mmol) of cis-stilbene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of indene wherein substrate is shown in entry 13, FIG. 6

In a 5 mL scintillation vial equipped with a magnetic stirrer, (2 mmol) of indene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of cyclohexene wherein substrate is shown in entry 14, FIG. 6

In a 5 mL scintillation vial equipped with a magnetic stirrer, (2 mmol) of cyclohexene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 1,2-dihydronaphthalene wherein substrate is shown in entry 15, FIG. 6

In a 50 mL flask equipped with a magnetic stirrer, 6.5 g (50 mmol) of 1,2-dihydronaphthalene and 63 mg (0.25 mmol, 0.5 mol %) MTO are dissolved in 25 mL $CH_2Cl_2$. To this solution is added 0.48 mL (6 mmol, 12 mol %) of pyridine followed by 7.6 mL (1.5 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 5 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified by filtration through a short column of silica gel. The column is washed with $Et_2O$ and concentration of the eluate affords 7.0 g (96%) of the product.

Epoxidation of 6-cyano-2.2-dimethylchromene wherein substrate is shown in entry 16, FIG. 6

In a 5 mL scintillation vial equipped with a magnetic stirrer, (2 mmol) of 6-cyano-2.2-dimethylchromene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of norbornene wherein substrate is shown in entry 17, FIG. 6

In a 5 mL scintillation vial equipped with a magnetic stirrer, (2 mmol) of norbornene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of cycloheptene wherein substrate is shown in entry 18, FIG. 6

In a 5 mL scintillation vial equipped with a magnetic stirrer, (2 mmol) of cycloheptene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of cis-cyclooctene wherein substrate is shown in entry 19, FIG. 6 and FIG. 2

In a 50 mL flask equipped with a magnetic stirrer, 5.5 g (50 mmol) of cis-cyclooctene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 1-phenyl-cyclohexene wherein substrate is shown in entry 20, FIG. 7

In a 5 mL scintillation vial equipped with a magnetic stirrer, (2 mmol) of 1-phenyl-cyclohexene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 3-menthene wherein substrate is shown in entry 21, FIG. 7

In a 5 mL scintillation vial equipped with a magnetic stirrer, (2 mmol) of 3-menthene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of cholesteryl acetate wherein substrate is shown in entry 22, FIG. 7

In a 5 mL scintillation vial equipped with a magnetic stirrer, (2 mmol) of cholesteryl acetate and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 2,3-dimethyl-2-octene wherein substrate is shown in entry 23, FIG. 7

In a 5 mL scintillation vial equipped with a magnetic stirrer, (2 mmol) of 2,3-dimethyl-2-octene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 2-menthene wherein substrate is shown in entry 24, FIG. 7

In a 5 mL scintillation vial equipped with a magnetic stirrer, (2 mmol) of 2-menthene and (10 μmol, 0.5 mol %)

of MTO (methyl-rhenium oxide) are dissolved in 1.5 Molar $CH_2Cl_2$. To this solution is added (228 µmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 1,3-cyclohexadiene wherein substrate is shown in entry 25, FIG. 8

In a 5 mL scintillation vial equipped with a magnetic stirrer, (2 mmol) of 1,3-cyclohexadiene and (10 µmol, 0.5 mol %) of MTO (methyl-rhenium oxide) are dissolved in 0.010 Molar $CH_2Cl_2$. To this solution is added (228 µmol, 12 mol %) of pyridine followed by (5 mmol, 2.5 equivalents) of 50% aqueous $H_2O_2$ added at once from a syringe. The reaction is complete after 6 h and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported in the figure under % conversion; anti-1,2;3,4-diepoxycyclohexane 25: $^1$H-NMR (400 MHz, $CDCl_3$), δ 3.33 (d, J=3.5 Hz, 2H), 3.14 (d, J=3.5 Hz, 2H), 1.88 (s, 4H); $^{13}$C-NMR (100 MHz, $CDCl_3$), δ 53.1, 50.0, 18.9; MS (EI): 83 (100%), 55 (85%), 68 (80%), 112 ($M^+$).

Epoxidation of 1,4-cyclohexadiene wherein substrate is shown in entry 26, FIG. 8

In a 5 mL scintillation vial equipped with a magnetic stirrer, 160 mg (2 mmol) of 1,4-cyclohexadiene and 2.5 mg (10 µmol, 0.5 mol %) of MTO are dissolved in 1 mL $CH_2Cl_2$. To this solution is added 18.4 µL (228 µmol, 12 mol %) of pyridine followed by 275 µL (5 mmol, 2.5 equivalents) of 50% aqueous $H_2O_2$ added at once from a syringe. The reaction is complete after 6 h and the remaining $H_2O_2$ is decomposed to $O_2$ and $H_2O$ by stirring with a catalytic amount of $MnO_2$ (circa 1 mg). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords 211 mg (94%) of a 96:4-mixture of anti- and syn- 1,2;4,5-diepoxycyclohexane as a crystalline solid. Physical data of anti-1,2;4,5-diepoxycyclohexane: $^1$H-NMR (400 MHz, $CDCl_3$), δ 3.05 (s, 4H), 2.30 (s, 4H); $^{13}$C-NMR (100 MHz, $CDCl_3$), δ 48.9, 23.8. MS:, MS (EI): 55 (100%), 39 (65%), 83 (60%), 112 ($M^+$), Anal. Calcd for $C_6H_8O_2$: C, 64.27; H, 7.19. Found: C, 64.12; H, 7.26; m.p. 107° C.; anti-1,2;4,5-diepoxycyclohexane 26 $^1$H-NMR (400 MHz, $CDCl_3$), δ 3.05 (s, 4H), 2.30 (s, 4H); $^{13}$C-NMR (100 MHz, $CDCl_3$), δ48.9, 23.8. MS:, MS (EI): 55 (100%), 39 (65%), 83 (60%), 112 ($M^+$), Anal. Calcd for $C_6H_8O_2$: C, 64.27; H, 7.19. Found: C, 64.12; H, 7.26; m.p. 107° C.

Epoxidation of 1,3-cyclooctadiene wherein substrate is shown in entry 27, FIG. 8

In a 5 mL scintillation vial equipped with a magnetic stirrer, (2 mmol) of 1,3-cyclooctadiene and (10 µmol, 0.5 mol %) of MTO (methyl-rhenium oxide) are dissolved in 0.010 Molar $CH_2Cl_2$. To this solution is added (228 µmol, 12 mol %) of pyridine followed by (5 mmol, 2.5 equivalents) of 50% aqueous $H_2O_2$ added at once from a syringe. The reaction is complete after 6 h and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported in the figure under % conversion; anti-1,2;3,4-diepoxycyclooctane 27: $^1$H-NMR (400 MHz, $CDCl_3$), δ 3.09 (d, J=3.9 Hz, 2H), 2.95 (dt, J=9.8, 3.6 Hz, 2H), 2.34 (m, 2H), 1.79 (t, J=9.9 Hz, 2H), 1.30 (t, J=8.4 Hz, 2H), 0.97 (m, 2H); $^{13}$C-NMR (100 MHz, $CDCl_3$), δ 56.9, 52.6, 29.1, 23.4; Anal. Calcd for $C_8H_{12}O_2$: C, 68.55; H, 8.63. Found: C, 67.79; H, 8.77; m.p. 74–76° C.

Epoxidation of 1,5-cyclooctadiene wherein substrate is shown in entry 28, FIG. 8

In a 5 mL scintillation vial equipped with a magnetic stirrer, (2 mmol) of 1,5-cyclooctadiene and (10 µmol, 0.5 mol %) of MTO (methyl-rhenium oxide) are dissolved in 0.010 Molar $CH_2Cl_2$. To this solution is added (228 µmol, 12 mol %) of pyridine followed by (5 mmol, 2.5 equivalents) of 50% aqueous $H_2O_2$ added at once from a syringe. The reaction is complete after 6 h and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported in the figure under % conversion; syn-1,2;5,6-diepoxycyclooctane 28: $^1$H-NMR (400 MHz, $CDCl_3$), δ 2.95 (m, 4H), 1.95, 1.91 (2 m, 8H), ; $^{13}$C-NMR (100 MHz, $CDCl_3$), δ 56.1, 22.0; HRMS (FAB): Calcd for $C_8H_{12}O_2$: [$(M+H)^+$]: 141.0916. Found: 141.0911, Anal. Calcd for $C_8H_{12}O_2$: C, 68.55; H, 8.63. Found: C, 68.60; H, 8.60.

Epoxidation of 2,6-dimethyl-1,5-cyclooctadiene wherein substrate is shown in entry 29, FIG. 8

In a 5 mL scintillation vial equipped with a magnetic stirrer, (2 mmol) of 2,6-dimethyl-1,5-cyclooctadiene and (10 µmol, 0.5 mol %) of MTO (methyl-rhenium oxide) are dissolved in 1.5 Molar $CH_2Cl_2$. To this solution is added (228 µmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of (S)-carvone is shown in entry 30, FIG. 8

In a 5 mL scintillation vial equipped with a magnetic stirrer, (2 mmol) of (S)-carvone and (10 µmol, 0.5 mol %) of MTO (methyl-rhenium oxide) are dissolved in 1.5 Molar $CH_2Cl_2$. To this solution is added (228 µmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of terpinolene wherein substrate is shown in entry 31, FIG. 8

In a 5 mL scintillation vial equipped with a magnetic stirrer, (2 mmol) of terpinolene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of (S)-limonene wherein substrate is shown in entry 32, FIG. 8

In a 5 mL scintillation vial equipped with a magnetic stirrer, (2 mmol) of (S)-limonene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of 5-methylene-2-norbornene wherein substrate is shown in entry 33, FIG. 8

In a 5 mL scintillation vial equipped with a magnetic stirrer, (2 mmol) of 5-methylene-2-norbornene and (10 μmol, 0.5 mol %) of MTO (methyl-rhenium oxide) are dissolved in 1.5 Molar $CH_2Cl_2$. To this solution is added (228 μmol, 12 mol %) of pyridine followed by (3 mmol, 1.5 equivalents) of 30% aqueous $H_2O_2$ added at once from a syringe. The reaction is stopped after it is determined finished by following by TLC or gas chromatography (looking for overall disappearance of starting material and appearance of product) and the remaining $H_2O_2$ is decomposed to $O_2$ and $H_2O$ by stirring with a catalytic amount of $MnO_2$ (ca 0.010 equivalents). After the yellow color has disappeared the mixture is dried over $Na_2SO_4$, concentrated, and purified by filtration through a small column of silica gel which has been deactivated with $NEt_3$. The column is washed with $Et_2O$ and concentration of the eluate affords the title epoxide wherein the yield is reported as illustrated in the figure under the conversion (%) column.

Epoxidation of styrene wherein substrate is shown in entry 1, FIG. 15 (case for 3-cyanopyridine accelerant on terminal alkenes)

In a 50 mL flask equipped with a magnetic stirrer, 50 mmol of styrene and 63 mg (0.25 mmol, 0.5 mol %) MTO are dissolved in 10 mL $CH_2Cl_2$. To this solution is added a mixture of 10 mol % of 3-cyanopyridine and 10 mol % pyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 85%.

Epoxidation of 1-decene wherein substrate is shown in entry 2, FIG. 15 (case for 3-cyanopyridine accelerant on terminal alkenes)

In a 50 mL flask equipped with a magnetic stirrer, 50 mmol of 1-decene and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 17 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 97%.

Epoxidation of vinylcyclohexane wherein substrate is shown in entry 3, FIG. 15 (case for 3-cyanopyridine accelerant on terminal alkenes)

In a 50 mL flask equipped with a magnetic stirrer, 50 mmol of vinylcyclohexane and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 30 h and the aqueous phase is separated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 86%.

Epoxidation of 3,3-dimethyl-1-hexane wherein substrate is shown in entry 4, FIG. 15 (case for 3-cyanopyridine accelerant on terminal alkenes)

In a 50 mL flask equipped with a magnetic stirrer, 50 mmol of 3,3-dimethyl-1-hexane and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 30 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 78%.

Epoxidation of allylcyclohexane wherein substrate is shown in entry 5, FIG. 15 (case for 3-cyanopyridine accelerant on terminal alkenes)

In a 50 mL flask equipped with a magnetic stirrer, 50 mmol of allylcyclohexane and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 20 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 89%.

Epoxidation of 9-decen-1-ol wherein substrate is shown in entry 6, FIG. 15 (case for 3-cyanopyridine accelerant on terminal alkenes)

In a 50 mL flask equipped with a magnetic stirrer, 50 mmol of 9-decen-1-ol and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 19 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 89%.

Epoxidation of 1-octen-3-ol wherein substrate is shown in entry 7, FIG. 15 (case for 3-cyanopyridine accelerant on terminal alkenes)

In a 50 mL flask equipped with a magnetic stirrer, 50 mmol of 1-octen-3-ol and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 27 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 94%.

Epoxidation of 1-nonen-4-ol wherein substrate is shown in entry 8, FIG. 15 (case for 3-cyanopyridine accelerant on terminal alkenes)

In a 50 mL flask equipped with a magnetic stirrer, 50 mmol of 1-nonen-4-ol and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 17 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 88%.

Epoxidation of 4-penten-1-ol wherein substrate is shown in entry 9, FIG. 15 (case for 3-cyanopyridine accelerant on terminal alkenes)

In a 50 mL flask equipped with a magnetic stirrer, 50 mmol of 4-penten-1-ol and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 18 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. In this case the epoxide reacted further to give the corresponding tetrahydrofurfuryl alcohol. Isolated yield of the tetrahydrofurfuryl alcohol: 97%.

Epoxidation of 4-penten-1-acetate wherein substrate is shown in entry 10, FIG. 15 (case for 3-cyanopyridine accelerant on terminal alkenes)

In a 50 mL flask equipped with a magnetic stirrer, 50 mmol of 4-penten-1-acetate and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 20 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 94%.

Epoxidation of 10-chloro-1-decene wherein substrate is shown in entry 11, FIG. 15 (case for 3-cyanopyridine accelerant on terminal alkenes)

In a 50 mL flask equipped with a magnetic stirrer, 50 mmol of 10-chloro-1-decene and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 30 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 86%.

Epoxidation of ethyl-1-undecenoate wherein substrate is shown in entry 12, FIG. 15 (case for 3-cyanopyridine accelerant on terminal alkenes)

In a 50 mL flask equipped with a magnetic stirrer, 50 mmol of ethyl-1-undecenoate and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 20 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 89%.

Epoxidation of N,N-diethyl-1-undecenamide wherein substrate is shown in entry 13, FIG. 15 (case for 3-cyanopyridine accelerant on terminal alkenes)

In a 50 mL flask equipped with a magnetic stirrer, 50 mmol of N,N-diethyl-1-undecenamide and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 19 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 90%.

Epoxidation of 11-oxo-tridecene wherein substrate is shown in entry 14, FIG. 15 (case for 3-cyanopyridine accelerant on terminal alkenes)

In a 50 mL flask equipped with a magnetic stirrer, 50 mmol of 11-oxo-tridecene and 63 mg (0.25 mmol, 0.5 mol %) MTO are dissolved in 25 mL $CH_2Cl_2$. To this solution is added 10 mol % of 3-cyanopyridine followed by 10 mL (2 equivalents) 30% aqueous $H_2O_2$ added dropwise from a syringe (circa 10 minutes). During the $H_2O_2$ addition the temperature is kept at 20–25° C. by applying an external cooling bath. The reaction is complete after 24 h and the aqueous phase is seperated and discarded. The remaining $H_2O_2$ in the yellow organic phase is decomposed to $O_2$ and $H_2O$ by stirring with acatalytic amount of $MnO_2$ (circa 10 mg). After the yellow color has completely disappeared the mixture is dried over $Na_2SO_4$, concentrated, and purified. Isolated yield: 96%.

Epoxidation of trans-4-octene wherein substrate is shown in entry 1, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 8 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 89%.

Epoxidation of trans-3-decene wherein substrate is shown in entry 2, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 7 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 91%.

Epoxidation of trans-2,2-dimethyl-3-hexene wherein substrate is shown in entry 3, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 15 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 89%.

Epoxidation of trans-3,5-dimethyl-3-hexene wherein substrate is shown in entry 4, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 8 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 85%.

Epoxidation of trans-β-methylstyrene wherein substrate is shown in entry 5, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.1 mmol, 5 mol %) of pyridine and (0.2 mmol, 10 mol %) of 3-cyanopyridine followed by (4 mmol, 2 equivalents) of 30% aqueous $H_2O_2$ added at once from a syringe. The reaction is complete after 2 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 84%.

Epoxidation of trans-stilbene wherein substrate is shown in entry 6, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.1 mmol, 5 mol %)

of pyridine and (0.2 mmol, 10 mol %) of 3-cyanopyridine followed by (4 mmol, 2 equivalents) of 30% aqueous $H_2O_2$ added at once from a syringe. The reaction is complete after 17 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. Concentration of the eluate and purification by crystallization affords the title epoxide with an isolated yield of 92%.

Epoxidation of trans-hexen-1-ol wherein substrate is shown in entry 7, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 6 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 80%.

Epoxidation of trans-3-hexen-1-ol wherein substrate is shown in entry 8, FIG. 16 (case for 3-cyanopyridine accelerant on trans alkenes)

In a 5 mL scintillation vial equipped with a magnetic stirrer, (2 mmol) of above olefin substrate and (5 μmol, 0.25 mol %) of MTO (methyl-rhenium oxide) are dissolved in 1 mL $CH_2Cl_2$. To this solution is added (0.1 mmol, 5 mol %) of 3-cyanopyridine followed by (4 mmol, 2 equivalents) of 30% aqueous $H_2O_2$ added at once from a syringe. The reaction is complete after 3 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 78%.

Epoxidation of cinnamyl alcohol wherein substrate is shown in entry 9, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.1 mmol, 5 mol %) of pyridine and (0.2 mmol, 10 mol %) of 3-cyanopyridine followed by (4 mmol, 2 equivalents) of 30% aqueous $H_2O_2$ added at once from a syringe. The reaction is complete after 3 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 93%.

Epoxidation of cinnamyl acetate wherein substrate is shown in entry 10, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.1 mmol, 5 mol %) of pyridine and (0.2 mmol, 10 mol %) of 3-cyanopyridine followed by (4 mmol, 2 equivalents) of 30% aqueous $H_2O_2$ added at once from a syringe. The reaction is complete after 26 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 80%.

Epoxidation of ethyl cinnamate wherein substrate is shown in entry 11, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 17 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 20%.

Epoxidation of trans ethyl 3-hexenoate wherein substrate is shown in entry 12, FIG. 16 (case for 3-cyanopyridine accelerant on trans alkenes)

In a 5 mL scintillation vial equipped with a magnetic stirrer, (2 mmol) of above olefin substrate and (10 μmol, 0.5 mol %) of MTO (methyl-rhenium oxide) are dissolved in 1 mL $CH_2Cl_2$. To this solution is added (0.2 mmol, 10 mol %) of 3-cyanopyridine followed by (4 mmol, 2 equivalents) of 30% aqueous $H_2O_2$ added at once from a syringe. The reaction is complete after 25 h and the remaining $H_2O_2$ is decomposed to $O_2$ and $H_2O$ by stirring with a catalytic amount of $MnO_2$ (circa 0.010 equivalents). After the yellow color has disappeared the mixture is dried over $Na_2SO_4$, concentrated, and purified by filtration through a small column of silica gel which has been deactivated with $NEt_3$. The title epoxide is obtained with a GLC yield of 86%.

Kinetic measurements for the reaction profile of MTO/pyridine catalyzed epoxidation of cyclooctene, the following experimental conditions were applied A solution containing 10 mL of the solvent, 9.57 mg (38.4 μmol) of MTO, various amounts of accelerant (0 mol %, 1 mol %, 12 mol % or other) and 7.68 mmol of the substrate (in case of cyclooctene: 1 mL) is prepared in a 15 mL scintillation vial. This vial is surrounded by a room temperature water bath. To the vigorously stirred solution is added a $H_2O_2$ solution (e.g. 2 equivalents 30% aqueous= 1.57 mL; 1.3 equivalents 50% aqueous=550 μL) at once and the reaction time is measured with a stop watch. The samples (150 μL each time) are taken out with an Eppendorf pipette and immediately quenched by giving them into small tubes (Fisherbrand, 12×75 mm) containing an excess (~30 mg) of $MnO_2$. To provide a rapid and complete quenching additional shaking is recommended. Samples can be taken out in the following sequence (depending on reaction speed): 15s, 30s, 45s, 1', 1'15, 1'30, 1'45, 2', 2'30, 3, 3'30, 4, 5, 6, 7, 8, 9, 10, 11, 12, 13, 14, 15, 16, 17, 19, 21, 23, 25, 27, 30 minutes or every minute. Each sample tube is filled up with 300 μL EtOAc and filtered through a mini column (pasteur pipet containing silica gel and $Na_2SO_4$ at the top) followed by two additional washings with small amounts of EtOAc. Each filtrate is directly filled into an autosampler GC flask.

What is claimed:

1. An improved method for catalyzing an epoxidation reaction, the method being of a type employing a step for admixing a solvent, an olefinic substrate, a catalytic organorhenium oxide, and hydrogen peroxide for forming a reaction admixture, the reaction admixture having conditions appropriate for converting the olefinic substrate to an epoxide product, wherein the improvement comprises:

in said admixing step, an accelerant having a nitrogenous aromatic heterocyclic structure is admixed into the reaction admixture at a concentration within a range from 2.0 mole percent to 100 mole percent of the accelerant with respect to 1 mole of the olefinic substrate for accelerating the catalysis of the epoxidation reaction and increasing the conversion of the olefinic substrate to the epoxide product.

2. A method as described in claim 1 wherein the accelerant is selected from a group consisting of pyridine, 3-cyanopyridine, 2-cyanopyridine, cotinine, 2-picoline, 2-ethylpyridine, 2-propylpyridine, 2-phenylpyridine, 2-(p-tolyl)pyridine, 2-benzylpyridine, 2-acetylpyridine, 2-benzoylpyridine, 2-fluoropyridine, 2-chloropyridine, 2-bromopyridine, 2-hydroxypyridine, 2-pyridylcarbinol, 2-pyridineethanol, 2-pyridinepropanol, 2-pyridylacetic acid, 2-pyridylacetonitrile, pyridine-2-carboxylic acid, methyl picolinate, ethyl picolinate, n-propyl picolinate, i-propyl picolinate, n-butyl picolinate, t-butyl picolinate, phenyl picolinate, benzyl picolinate, picolinamide, 3-hydroxypicolinamide, N-methylpicolinamide, N-ethylpicolinamide, N,N-dimethylpicolinamide, N,N-diethylpicolinamide, 3-methylpyridine, 3-ethylpyridine, 3-butylpyridine, 3-phenylpyridine, 3-benzylpyridine, 3-acetylpyridine, 3-benzoylpyridine, 3-fluoropyridine, 3-chloropyridine, 3-bromopyridine, 3-pyridylcarbinol, 3-hydroxypyridine, 3-pyridinepropanol, 3-pyridylacetonitrile, 3-pyridylacetic acid, pyridine-3-carboxylic acid, methyl nicotinate, ethyl nicotinate, n-propyl nicotinate, i-propyl nicotinate, n-butyl nicotinate, t-butyl nicotinate, phenyl nicotinate, benzyl nicotinate, nicotinamide, 6-methylnicotinamide, thionicotinamide, N-methylnicotinamide, N-ethylnicotinamide, N,N-dimethylnicotinamide, N,N-diethylnicotinamide, N-(hydroxymethyl)-nicotinamide, 6-chloronicotinamide, 2-chloronicotinamide, 4-methylpyridine, 4-fluoropyridine, 4-chloropyridine, 4-bromopyridine, 4-cyanopyridine, 4-ethylpyridine, 4-isopropylpyridine, 4-t-butylpyridine, 4-(1-butylpentyl)pyridine, 4-phenylpyridine, 4-benzylpyridine, 4-(4-chlorobenzyl)pyridine, 4-pyridylacetic acid, 4-acetylpyridine, 4-benzoylpyridine, 4-(4-chlorobenzoyl)pyridine, 4-pyridylacetonitrile, isonicotinic acid, methyl isonicotinate, ethyl isonicotinate, n-propyl isonicotinate, i-propyl isonicotinate, n-butyl isonicotinate, t-butyl isonicotinate, phenyl isonicotinate, benzyl isonicotinate, isonicotinamide, N-methylisonicotinamide, N-ethylisonicotinamide, N,N-dimethylisonicotinamide, N,N-diethylisonicotinamide, thioisonicotinamide, N-(2-hydroxymethyl)-isonicotinamide, N,N-bis(2-hydroxymethyl)-isonicotinamide, 4-hydroxypyridine, 4-methoxypyridine, 4-nitropyridine, 4-pyridylcarbinol, pyridine-4-carboxylic acid, 2,3-lutidine, 2,4-lutidine, 2,5-lutidine, 2,6-lutidine, 3,4-lutidine, 3,5-lutidine, 3-methyl-2-phenylpyridine, 5-ethyl-2-methylpyridine, 2,6-di-tert-butylpyridine, 2,6-di-tertbutyl-4-methylpyridine, 2,6-diacetylpyridine, 2,6-difluoropyridine, pentafluoropyridine, 2,3,5,6-tetrafluoropyridine, pentachloropyridine, 2,3-dichloropyridine, 2,5-dichloropyridine, 2,6-dichloropyridine, 3,5-dichloropyridine, 2,3,5-trichloropyridine, 2,5-dibromopyridine, 2,6-dibromopyridine, 3,4-dicyanopyridine, 5-chloro-3-pyridinol, 2,3-pyridinedicarboxylic acid, dimethyl 2,3-pyridinedicarboxylate, diethyl 2,3-pyridinedicarboxylate, dipropyl 2,3-pyridinedicarboxylate, dibutyl 2,3-pyridinedicarboxylate, 2,4-pyridinedicarboxylic acid, dimethyl 2,4-pyridinedicarboxylate, diethyl 2,4-pyridinedicarboxylate, dipropyl 2,4-pyridinedicarboxylate, dibutyl 2,4-pyridinedicarboxylate, 2,5-pyridinedicarboxylic acid, dimethyl 2,5-pyridinedicarboxylate, diethyl 2,5-pyridinedicarboxylate, dipropyl 2,5-pyridinedicarboxylate, dibutyl 2,5-pyridinedicarboxylate, 3,5-pyridinedicarboxylic acid, dimethyl 3,5-pyridinedicarboxylate, diethyl 3,5-pyridinedicarboxylate, dipropyl 3,5-pyridinedicarboxylate, dibutyl 3,5-pyridinedicarboxylate, 2,6-pyridinedicarboxylic acid, dimethyl 2,6-pyridinedicarboxylate, diethyl 2,6-pyridinedicarboxylate, dipropyl 2,6-pyridinedicarboxylate, dibutyl 2,6-pyridinedicarboxylate, 2,6-diphenylpyridine, 2,6-di-p-tolylpyridine, 3,4-pyridinedicarboxylic acid, dimethyl 3,4-pyridinedicarboxylate, diethyl 3,4-pyridinedicarboxylate, dipropyl 3,4-pyridinedicarboxylate, dibutyl 3,4-pyridinedicarboxylate, 2-pyridine-ethansulfonic acid, 4-pyridineethanesulfonic acid, 2,3-cyclopentenopyridine, 2,3-cyclohexenopyridine, 2,3-cycloheptenopyridine, diphenyl-2-pyridylmethane, diphenyl-4-pyridylmethane, 6-chloro-2-picoline, 2-chloro-5-(trifluoromethyl)-pyridine, 2-chloro-3,5-bis(trifluoromethyl)pyridine, 2-chloro-4,5-bis(trifluoromethyl)pyridine, 2-chloro-4,6-bis(trifluoromethyl)pyridine, 4-chloro-2,6-bis(trifluoromethyl)pyridine, 2,3-dichloro-5-(trifluoromethyl)pyridine, 2,3,5,6-tetrafluoro-4-methylpyridine, 3-chloro-2,4,5,6-tetrafluoropyridine, 3,5-dichloro-2,4,6-trifluoropyridine, 4-bromo-2,3,4,6-tetrafluoropyridine, 2-(2-isopropoxyethyl)-pyridine, 2-(2-propoxyethyl)pyridine, 2-(2-hydroxyethyl)pyridine, 2,3-di-2-pyridyl-2,3-butanediol, 2,3-di-3-pyridyl-2,3-butanediol, α-4-pyridylbenzhydrol, 2-hydroxy-4-methylpyridine, 2-hydroxy-6-methylpyridine, 6-methyl-2-pyridinepropanol, 2-[3-(6-methyl-2-pyridyl)propoxy]ethanol, 3-hydroxy-2-methylpyridine, 6-chloro-2-pyridinol, 5-chloro-2-pyridinol, 2,3-dihydroxypyridine, 2,6-dihydroxypyridine, 5-chloro-2,3-pyridinediol, 2,2'-bipyridine-3,3'-diol, 2,4-dihydroxypyridine, 5-hydroxy-2-methylpyridine, 5-chloro-3-pyridinol, 2-chloro-3-pyridinol, 2-bromo-3-pyridinol, 3-hydroxy-2-(hydroxymethyl)-pyridine, 2,6-pyridinedimethanol, 2,6-lutidine-2,3-diol, pyridoxine, 4-amino-3,5-dichloro-2,6-difluoropyridine, 4-(4-nitrobenzyl)pyridine, 2-chloro-3-nitropyridine, 2-chloro-5-nitropyridine, 2-bromo-5-nitropyridine, 2-hydroxy-3-nitropyridine, 3-ethoxy-2-nitropyridine, 2-chloro-4-methyl-3-nitropyridine, 3-hydroxy-2-nitropyridine, 2,6-dichloro-3-nitropyridine, 2-hydroxy-4-methyl-3-nitropyridine, 2-chloro-3,5-dinitropyridine, 2-hydroxy-5-nitropyridine, 2-hydroxy-4-methyl-5-nitropyridine, 2-chloro-4-methyl-5-nitropyridine, 3-hydroxy-6-methyl-2-nitropyridine, α-pyridoin, 2-methyl-1,2-di-3-pyridyl-1-propanone, 3-acetyl-2,6-bis(tert-butylamino)-4-methylpyridine, 2,2'-bipyridine-4,4'dicarboxylic acid, 2-methylnicotinic acid, 6-methylnicotinic acid, fusaric acid, 2-chloronicotinic acid, 5-bromonicotinic acid, 6-chloronicotinic acid, 2-chloro-6-methylnicotinic acid, 2,6-dichloronicotinic acid, 5,6-dichloronicotinic acid, 6-hydroxynicotinic acid, 3-hydroxypicolinic acid, 2-hydroxynicotinic acid, 2-hydroxy-6-methylpyridine-3-carboxylic acid, 5-chloro-6-hydroxynicotinic acid, 4-pyridoxic acid, 2,6-dimethoxynicotinic acid, citrazinic acid, 6-methyl-2,3-pyridinedicarboxylic acid, methyl-2-pyridylacetate, ethyl 2-pyridylacetate, 3-acetoxypyridine, methyl 6-methylnicotinate, ethyl 2-methylpicolinate, ethyl 3-pyridylacetate, 3,4-pyridinedicarboxamide, 3,4-pyridinedicarboximide, methyl 3-pyridylcarbamate, 1-(3-pyridylmethyl)urea, 1,3-bis(3-pyridylmethyl)-2-thiourea, trans-4-cotininecarboxylic acid, 3-(3-pyridylmethylamino)-propionitrile, 3,4-pyridinedicarbonitrile, 2-chloro-6-methyl-3-pyridinecarbonitrile, 3-cyano-4,6-dimethyl-2-hydroxypyridine, 2,6-dihydroxy-4-methyl-3-pyridinecarbonitrile, 2,3,5,6-tetrafluoro-4-pyridinecarbonitrile, 2,4,6-collidine, pyrazine, 2,3-pyrazinedicarbonitrile, pyrazinecarbonitrile, 2,6-dichloropyrazine, pyrazinecarboxylic, methyl pyrazinecarboxylate, ethyl pyrazinecarboxylate, propyl pyrazinecarboxylate, butyl pyrazinecarboxylate, 2,3-dimethylpyrazine, 2,5-dimethylpyrazine, 2,6-dimethylpyrazine, 2,3-di-2-pyridylpyrazine, 2-methylpyrazine, ethylpyrazine, 2,6-dimethylpyrazine, 2,5-dimethylpyrazine, 2,3-dimethylpyrazine, 2-ethyl-3-methylpyrazine, 2,3-diethylpyrazine, 2-methyl-3-propylpyrazine, 5,6,7,8-tetrahydroquinoxaline, 2,3,5-trimethylpyrazine, 2,3-diethyl-5-methylpyrazine, tetramethylpyrazine, chloropyrazine, 2-methoxypyrazine, 2-methoxy-3-methylpyrazine, 2-ethyl-3-methoxypyrazine, 2-isopropyl-3-methoxypyrazine, 2-sec-butyl-3-methoxypyrazine, 2-isobutyl-3-methoxypyrazine, 2-methyl-6-propoxypyrazine, 3-chloro-2,5-dimethylpyrazine, acetylpyrazine, 2-pyrazinecarboxylic acid, 5-methyl-2-pyrazinecarboxylic acid, 2,3-pyrazinedicarboxylic acid, pyrazinamide, 2,3-pyrazinedicarboxamide, 2,3-bis(2-pyridyl)pyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinol, 2-chloropyrimidine, 5-bromopyrimidine, 2,4,6-trichloropyrimidine, 2,4,5,6-tetrachloropyrimidine, 2,4-dichloro-6-methylpyrimidine, 2,4-dichloro-6-methylpyrimidine, 6-chloro-2,4-dimethoxypyrimidine, 2-hydroxypyrimidine, 4,6-dimethyl-2-hydroxypyrimidine, 2,4-dimethyl-6-hydroxypyrimidine, 4,6-dimethyl-2-hydroxypyrimidine, 2-isopropyl-6-methyl-4-pyrimidinol, 4,6-dihydroxypyrimidine, 2,4-dihydroxy-5,6-dimethylpyrimidine, 2,4-dihydroxy-6-methylpyrimidine, 4,6-dihydroxy-2-methylpyrimidine, 2,4,5-trihydroxypyrimidine, 4,6-dichloro-5-nitropyrimidine, 4,6-dihydroxy-5-nitropyrimidine, 2,4-dihydroxypyrimidine-5-carboxylic acid, 1,3,5-triazine, 2-chloro-4,6-dimethoxy-1,3,5-triazine, 2,4,6-triphenoxy-1,3,5-triazine, 2,4,6-triphenyl-1,3,5-triazine, 2,4,6-tri(2-pyridyl)-1,3,5-triazine, (−)-cotinine (1-methyl-5-(3-pyridyl)-2-pyrrolidinone), quinoline, 2,2'-biquinoline, quinaldine, lepidine, 6-methylquinoline, 7-methylquinoline, 8-methylquinoline, 2,4-dimethylquinoline, 2,6-dimethylquinoline, 2,7-dimethylquinoline, 2,8-dimethylquinoline, 2-phenylquinoline, 7,8-benzoquinoline, 2-chloroquinoline, alpha,alpha,alpha-tribromoquinaldine, 4-chloroquinoline, 6-chloroquinoline, 4-chloro-7-(trifluoromethyl)quinoline, 4-chloro-8-(trifluoromethyl)quinoline, 4-chloro-2,8-bis(trifluoromethyl)quinoline, 4-chloroquinaldine, 7-chloroquinaldine, 2-chlorolepidine, 3-bromoquinoline, 4,7-dichloroquinoline, 4-bromo-2,8-bis(trifluoromethyl)quinoline, 6-methoxyquinoline, 6-methoxyquinaldine, 2-hydroxy-4-methylquinoline, 4-hydroxyquinoline, 7-chloro-4-hydroxyquinoline, 8-(trifluoromethyl)-4-quinolinol, 2,4-quinolinediol, 2-hydroxyquinoline, 5-hydroxyquinoline, 6-hydroxyquinoline, 8-hydroxyquinoline, 8-hydroxyquinaldine, 4-hydroxy-2-methylquinoline, 7-(trifluoromethyl)-4-quinolinol, 2,8-bis(trifluoromethyl)-4-quinolinol, 5-chloro-8-hydroxyquinoline, 5,7-dichloro-8-hydroxyquinoline, 5,7-dibromo-8-hydroxyquinoline, 5,7-dibromo-2-methyl-8-quinolinol, 5,7-dichloro-2-methyl-8-quinolinol, 5-nitroquinoline, 6-nitroquinoline, 8-nitroquinoline, 8-nitroquinaldine, 8-methyl-5-nitroquinoline, 8-hydroxy-5-nitroquinoline, 6-methoxy-8-nitroquinoline, quinaldic acid, 3-quinolinecarboxylic acid, 4-quinolinecarboxylic acid, 8-quinolinecarboxylic acid, 1,2,3,4-tetrahydro-9-acridinecarboxylic acid, 4-methoxy-2-quinolinecarboxylic acid, 4-hydroxyquinoline-2-carboxylic acid, 4-hydroxy-7-trifluoromethyl-3-quinolinecarboxylic acid, 4,8-dihydroxyquinoline-2-carboxylic acid, 2-phenyl-4-quinolinecarboxylic acid, ethyl 4-hydroxy-7-trifluoromethyl-3-quinolinecarboxylate, methyl 2-phenyl-4-quinolinecarboxylate, 2-quinolinecarbonitrile, 3-quinolinecarbonitrile, 2,8-bis(trifluoromethyl)-4-quinolinecarbonitrile, 5,6,7,8-tetrahydroisoquinoline, 3-methyl-5,6,7,8-tetrahydroquinoline, 1,2,3,4,5,6,7,8-octahydroacridine, acridine, 5-triazolo(4,3-A)quinoline, 6,9-dichloro-2-methoxyacridine, 9-hydroxy-4-methoxyacridine, 9-acridinecarboxylic acid, 4,9-acridinedicarboxylic acid, 1,3-dihydroxy-9-acridinecarboxylic acid, phenyl 9-acridinecarboxylate, isoquinoline, 3-methylisoquinoline, 4-bromoisoquinoline, 1,3-dichloroisoquinoline, papaverine, isocarbostyril, 3-hydroxyisoquinoline, 5-hydroxyisoquinoline, 1,5-isoquinolinediol, 5-nitroisoquinoline, 1-isoquinolinyl phenyl ketone, protopapaverine, 1-isoquinolinecarboxylic acid, 3-isoquinolinecarboxylic acid, methyl 3-isoquinolinecarboxylate, 1-isoquinolinecarbonitrile, 3-isoquinolinecarbonitrile, benz[g]isoquinoline-5,10-dione, 3,8-dinitro-6-phenylphenanthridine, cinnoline, phenanthridine, 3,8-diamino-6-phenylphenanthridine, benzo[c]cinnoline, cinnoline-4-carboxylic acid, phthalazine, 1,4-dichlorophthalazine, 1(2H)-phthalazinone, quinazoline, 4-hydroxyquinazoline, 2-methyl-4(3H)-quinazolinone, quinoxaline, 2-methylquinoxaline, 5-methylquinoxaline, 2,3-dimethylquinoxaline, ethyl 2-quinoxalinecarboxylate, 2,3-diphenylquinoxaline, 6,7-dimethyl-2,3-di-(2-pyridyl)quinoxaline, phenazine, 2,3-dichloroquinoxaline, 2,3,6,7-tetrachloroquinoxaline, 2,3-bis(bromomethyl)-quinoxaline, 2-quinoxalinol, 3-methyl-2-quinoxalinol, 2,3-dihydroxyquinoxaline, 2-quinoxalinecarboxylic acid, 3-hydroxy-2-quinoxalinecarboxylic acid, 4-hydroxy-7-methyl-1,8-naphthyridine-3-carboxylic acid, 2,2'-pyridyl, 2,2'-dipyridyl, 4,4'-dimethyl-2,2'-dipyridyl, 4,4'-diphenyl-2,2'dipyridyl, 6-chloro-2,2'-bipyridine, 2,4'-dipyridyl, 4,4'-dipyridyl, di-2-pyridyl ketone, 2,2':6',2''-terpyridine, 1,7-phenanthroline, 1,10-phenanthroline, 4,7-phenanthroline, phenazine, 4-methyl-1,10-phenanthroline, 5-methyl-1,10-phenanthroline, neocuproine, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,9-dimethyl-4,7-diphenyl-1,10-phenanthroline, 5-chloro-1,10-phenanthroline, 6,7-dihydro-5,8-dimethyldibenzo-(1-10)-phenantlhroline, 5-nitro-1,10-phenylanthroline, 7-oxo-7-H-benzo[e]perimidine-4-carboxylic acid, lumazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-phenylpyrazole, 3-methyl-1-phenylpyrazole, 3-methyl-1-phenyl-2-pyrazolin-5-one, 4-benzoyl-3-methyl-1-phenyl-2-pyrazolin-5-one, 4-(3-methyl-5-oxo-2-pyrazolin-1-yl)-benzoic acid, 3,5- dimethylpyrazole-1-carboxamide, 1-nitropyrazole, oxazole, 2,5-diphenyloxazole, 2,4,5-trimethyloxazole, 1,4-bis(5-phenyloxazol-2-yl)-benzene, 1,4-bis(4-methyl-5-phenyloxazol-2-yl)benzene, 5-phenyl-2-(4-pyridyl)-oxazole, 2-(4-biphenylyl)-5-phenyloxazole, 2,5-bis(4-biphenylyl)oxazole, 2-methyl-4,5-diphenyloxazole, 9,10-dihydro-2-methyl-4H-benzo(5,6)cyclohept(1,2)-oxazol-4-ol, N1-(4,5-dimethyloxazol-2-yl)-sulfanilamide, 2,5-diphenyl-1,3,4-oxadiazole, 2-(4-biphenylyl)-5-phenyl-1,3,4-oxadiazole, 2-(4-biphenylyl)-5-(4-tert-butylphenyl)-1,3,4-oxadiazole, 2,5-bis(4-aminophenyl)-1,3,4-oxadiazole, 2,5-bis(4-diethylaminophenyl)- 1,3,4-oxadiazole, benzoxazole, 2-methylbenzoxazole, 2,5-dimethylbenzoxazole, 2-methyl-5-phenylbenzoxazole, 2-(4-biphenylyl)-6-phenylbenzoxazole, 2-chlorobenzoxazole, 2-phenylbenzoxazole, 2-(2'-hydroxyphenyl)-benzoxazole, 2,4,4-trimethyl-2-oxazoline, isoxazole, 1,2-benzisoxazole, 3,5-dimethylisoxazole, 5-methylisoxazole, 3,5-dimethylisoxazole, 4-(chloromethyl)-3,5-dimethylisoxazole, 3,5-dimethyl-4-nitroisoxazole, 5-methyl-3-phenylisoxazole-4-carboxylic acid, N,5-dimethyl-3-phenylisoxazole-4-carboxamide, N,5-dimethyl-3-(4-fluorophenyl)-4-isoxazolecarboxamide, 2,5-diphenyloxazole, 2,6-bis[(4S)-isopropyl-2-oxazolin-2-yl]pyridine, 1,5-pentamethylenetetrazole, 1,2-dimethylimidazole, 1-methylimidazole, 1-ethylimidazole, 1-propylimidazole, 1-butylimidazole, 1-phenylimidazole, 1-benzylimidazole, 1-benzyl-2-1-(2,3,4,6-tetrafluorophenyl)-imidazole, 1-(2-chloroethyl)-2-methyl-5-nitroimidazole, metronidazole, 2-methyl-4-nitro-1-imidazolepropionic acid, 2-methyl-4-nitro-1-imidazolepropionitrile, 1,5-dicyclohexylimidazole, 5-chloro-1-methylimidazole, 5-chloro-1-ethyl-2-methylimidazole, 4-(imidazol-1-yl)phenol, imidazo(1,2-A)pyridine, anthranil, 2,3,3-trimethylindolenine, caffeine and 6-chloropurine riboside.

3. A method for catalyzing an epoxidation reaction by admixing a solvent, an olefinic substrate, a catalytic organorhenium oxide, hydrogen peroxide, and an accelerant for forming a reaction admixture having conditions appropriate for converting the olefinic substrate to an epoxidation product, the accelerant having a nitrogenous aromatic heterocyclic structure and being admixed into the reaction admixture at a concentration within a range from 2.0 mole percent to 100 mole percent of the accelerant with respect to 1 mole of the olefinic substrate.

4. A method as described in claim 3 wherein the organorhenium oxide is represented by the formula $R_1ReO_3$ wherein $R_1$ is selected form a group of radicals consisting of methyl, ethyl, n-propyl, n-butyl, n-pentyl, n-hexyl, heptyl, octyl, isopropyl, t-butyl, adamantyl, phenyl, benzyl, cyclopropyl, cyclobutyl, cyclopentyl, cyclohexyl, 1-bicyclo(2.2.2)octanyl, 1-bicyclo(2.2.1)heptanyl, 1-bicyclo(2.1.1)hexanyl, 1-bicyclo(1.1.1)pentanyl, 1-bicyclo(3.2.1)octanyl, 1-bicyclo(1.1.3)heptanyl, cubyl, sec-butyl, neo-pentyl, 3-methylbutyl, (S)-2-methylbutyl, (R,S)-2-ethylhexyl, trimethylsilylmethyl, γ-diethylamino-n-propyl, tolyl, 2,6-dimethylphenyl, 2,4,6-trimethylphenyl, pentafluorophenyl, 4-hydroxy-2,6-dimethylphenyl, 4-trimethylsiloxy-2,6-dimethylphenyl, ethynyl, phenylethynyl, methylallyl, methylvinyl, 2,4-pentadienyl, and ethylacetyl.

5. A method as described in claim 3 wherein the solvent is selected from a group consisting of nitromethane, nitroethane, methylene chloride, chloroform, carbon tetrachloride, freon-12, chloroethane, 1,2-dichloroethane, pentachloroethane, 1-chloropropane, 1-chlorobutane, chlorobenzene, dichlorobenzene, trichlorobenzene, fluorobenzene, difluorobenzene, trifluorobenzene, trifluoromethylbenzene, fluoroethane, acetonitrile, acetone, benzene, toluene, 2-fluorotoluene, 4-fluorotoluene, nitrobenzene, o-xylene, m-xylene, p-xylene, mesitylene, 1,2,3-trimethyl benzene, 1,2,4-trimethyl benzene, methanol, ethanol, propanol, isopropanol, butanol, t-butanol, ethyleneglycol, diethylether, dioxane, tetrahydrofuran, and supercritical $CO_2$.

6. A method as described in claim 3 wherein the solvent is a mixture selected from a group consisting of nitromethane/t-butanol, nitromethane/n-propanol, nitromethane/i-propanol, nitromethane/ethanol, nitromethane/methanol, methylene chloride/t-butanol, methylene chloride/n-propanol, methylene chloride/i-propanol, methylene chloride/ethanol, methylene chloride/methanol, chloroform/t-butanol, chloroform/n-propanol, chloroform/i-propanol, chloroform/ethanol, and chloroform/methanol.

7. A method as described in claim 3 wherein the hydrogen peroxide is aqueous and has a concentration been 10 and 85%.

8. A method as described in claim 3 wherein the accelerant is present in 12 mole percent overall concentration with respect to 1 mole of the olefin substrate.

9. A method as described in claim 3 wherein the accelerant is selected from a group consisting of pyridine, 3-cyanopyridine, 2-cyanopyridine, cotinine, 2-picoline, 2-ethylpyridine, 2-propylpyridine, 2-phenylpyridine, 2-(p-tolyl)pyridine, 2-benzylpyridine, 2-acetylpyridine, 2-benzoylpyridine, 2-fluoropyridine, 2-chloropyridine, 2-bromopyridine, 2-hydroxypyridine, 2-pyridylcarbinol, 2-pyridineethanol, 2-pyridinepropanol, 2-pyridylacetic acid, 2-pyridylacetonitrile, pyridine-2-carboxylic acid, methyl picolinate, ethyl picolinate, n-propyl picolinate, i-propyl picolinate, n-butyl picolinate, t-butyl picolinate, phenyl picolinate, benzyl picolinate, picolinamide, 3-hydroxypicolinamide, N-methylpicolinamide, N-ethylpicolinamide, N,N-dimethylpicolinamide, N,N-diethylpicolinamide, 3-methylpyridine, 3-ethylpyridine, 3-butylpyridine, 3-phenylpyridine, 3-benzylpyridine, 3-acetylpyridine, 3-benzoylpyridine, 3-fluoropyridine, 3-chloropyridine, 3-bromopyridine, 3-pyridylcarbinol, 3-hydroxypyridine, 3-pyridinepropanol, 3-pyridylacetonitrile, 3-pyridylacetic, acid, pyridine-3-carboxylic acid, methyl nicotinate, ethyl nicotinate, n-propyl nicotinate, i-propyl nicotinate, n-butyl nicotinate, t-butyl nicotinate, phenyl nicotinate, benzyl nicotinate, nicotinamide, 6-methylnicotinamide, thionicotinamide, N-methylnicotinamide, N-ethylnicotinamide, N, N-dimethylnicotinamide, N,N-diethylnicotinamide, N-(hydroxymethyl)-nicotinamide, 6-chloronicotinamide, 2-chloronicotinamide, 4-methylpyridine, 4-fluoropyridine, 4-chloropyridine, 4-bromopyridine, 4-cyanopyridine, 4-ethylpyridine, 4-isopropylpyridine, 4-t-butylpyridine, 4-(1-butylpentyl)pyridine, 4-phenylpyridine, 4-benzylpyridine, 4-(4-chlorobenzyl)pyridine, 4-pyridylacetic acid, 4-acetylpyridine, 4-benzoylpyridine, 4-(4-chlorobenzoyl)pyridine, 4-pyridylacetonitrile, isonicotinic acid, methyl isonicotinate, ethyl isonicotinate, n-propyl isonicotinate, i-propyl isonicotinate, n-butyl isonicotinate, t-butyl isonicotinate, phenyl isonicotinate, benzyl isonicotinate, isonicotinamide, N-methylisonicotinamide, N-ethylisonicotinamide, N,N-dimethylisonicotinamide, N,N-diethylisonicotinamide, thioisonicotinamide, N-(2-hydroxymethyl)-isonicotinamide, N,N-bis(2-hydroxymethyl)-isonicotinamide, 4-hydroxypyridine, 4-methoxypyridine, 4-nitropyridine, 4-pyridylcarbinol, pyridine-4-carboxylic acid, 2,3-lutidine, 2,4-lutidine, 2,5-lutidine, 2,6-lutidine, 3,4-lutidine, 3,5-lutidine, 3-methyl-2-phenylpyridine, 5-ethyl-2-methylpyridine, 2,6-di-tert-butylpyridine, 2,6-di-tert-butyl-4-methylpyridine, 2,6-diacetylpyridine, 2,6-difluoropyridine, pentafluoropyridine, 2,3,5,6-tetrafluoropyridine, pentachloropyridine, 2,3-dichloropyridine, 2,5-dichloropyridine, 2,6-dichloropyridine, 3,5-dichloropyridine, 2,3,5-trichloropyridine, 2,5-dibromopyridine, 2,6-dibromopyridine, 3,4-dicyanopyridine, 5-chloro-3-pyridinol, 2,3-pyridinedicarboxylic acid, dimethyl 2,3-pyridinedicarboxylate, diethyl 2,3-pyridinedicarboxylate, dipropyl 2,3-pyridinedicarboxylate, dibutyl 2,3-pyridinedicarboxylate, 2,4-pyridinedicarboxylic acid, dimethyl 2,4-pyridinedicarboxylate, diethyl 2,4-pyridinedicarboxylate, dipropyl 2,4-pyridinedicarboxylate, dibutyl 2,4-pyridinedicarboxylate, 2,5-pyridinedicarboxylic acid, dimethyl 2,5-pyridinedicarboxylate, diethyl 2,5-pyridinedicarboxylate, dipropyl 2,5-pyridinedicarboxylate, dibutyl 2,5-pyridinedicarboxylate, 3,5-pyridinedicarboxylic acid, dimethyl 3,5-pyridinedicarboxylate, diethyl 3,5-pyridinedicarboxylate, dipropyl 3,5-pyridinedicarboxylate, dibutyl 3,5-pyridinedicarboxylate, 2,6-pyridinedicarboxylic acid, dimethyl 2,6-pyridinedicarboxylate, diethyl 2,6-pyridinedicarboxylate, dipropyl 2,6-pyridinedicarboxylate, dibutyl 2,6-pyridinedicarboxylate, 2,6-diphenylpyridine, 2,6-di-p-tolylpyridine, 3,4-pyridinedicarboxylic acid, dimethyl 3,4-pyridinedicarboxylate, diethyl 3,4-pyridinedicarboxylate, dipropyl 3,4-pyridinedicarboxylate, dibutyl 3,4-pyridinedicarboxylate, 2-pyridine-ethansulfonic acid, 4-pyridineethanesulfonic acid, 2,3-cyclopentenopyridine, 2,3-cyclohexenopyridine, 2,3-cycloheptenopyridine, diphenyl-2-pyridylmethane, diphenyl-4-pyridylmethane, 6-chloro-2-picoline, 2-chloro-5-(trifluoromethyl)-pyridine, 2-chloro-3,5-bis(trifluoromethyl)pyridine, 2-chloro-4,5-bis(trifluoromethyl)pyridine, 2-chloro-4,6-bis(trifluoromethyl)pyridine, 4-chloro-2,6-bis(trifluoromethyl)pyridine, 2,3-dichloro-5-(trifluoromethyl)pyridine, 2,3,5,6-tetrafluoro-4-methylpyridine, 3-chloro-2,4,5,6-tetrafluoropyridine, 3,5-dichloro-2,4,6-trifluoropyridine, 4-bromo-2,3,4,6-tetrafluoropyridine, 2-(2-isopropoxyethyl)-pyridine, 2-(2-propoxyethyl)pyridine, 2-(2-hydroxyethyl)pyridine, 2,3-di-2-pyridyl-2,3-butanediol, 2,3-di-3-pyridyl-2,3-butanediol, α-4-pyridylbenzhydrol, 2-hydroxy-4-methylpyridine, 2-hydroxy-6-methylpyridine, 6-methyl-2-pyridinepropanol, 2-[3-(6-methyl-2-pyridyl)propoxy]ethanol, 3-hydroxy-2-methylpyridine, 6-chloro-2-pyridinol, 5-chloro-2-pyridinol, 2,3-dihydroxypyridine, 2,6-dihydroxypyridine, 5-chloro-2,3-pyridinediol, 2,2'-bipyridine-3,3'-diol, 2,4-dihydroxypyridine, 5-hydroxy-2-methylpyridine, 5-chloro-3-pyridinol, 2-chloro-3-pyridinol, 2-bromo-3-pyridinol, 3-hydroxy-2-(hydroxymethyl)-pyridine, 2,6-pyridinedimethanol, 2,6-lutidine-2,3-diol, pyridoxine, 4-amino-3,5-dichloro-2,6-difluoropyridine, 4-(4-nitrobenzyl)pyridine, 2-chloro-3-nitropyridine, 2-chloro-5-nitropyridine, 2-bromo-5-nitropyridine, 2-hydroxy-3-nitropyridine, 3-ethoxy-2-nitropyridine, 2-chloro-4-methyl-3-nitropyridine, 3-hydroxy-2-nitropyridine, 2,6-dichloro-3-nitropyridine, 2-hydroxy-4-methyl-3-nitropyridine, 2-chloro-3,5-dinitropyridine, 2-hydroxy-5-nitropyridine, 2-hydroxy-4-methyl-5-nitropyridine, 2-chloro-4-methyl-5-nitropyridine, 3-hydroxy-6-methyl-2-nitropyridine, α-pyridoin, 2-methyl-1,2-di-3-pyridyl-1-propanone, 3-acetyl-2,6-bis(tert-butylamino)-4-methylpyridine, 2,2'-bipyridine-4,4'dicarboxylic acid, 2-methylnicotinic acid, 6-methylnicotinic acid, fusaric acid, 2-chloronicotinic acid, 5-bromonicotinic acid, 6-chloronicotinic acid, 2-chloro-6-methylnicotinic acid, 2,6-dichloronicotinic acid, 5,6-dichloronicotinic acid, 6-hydroxynicotinic acid, 3-hydroxypicolinic acid, 2-hydroxynicotinic acid, 2-hydroxy-6-methylpyridine-3-carboxylic acid, 5-chloro-6-hydroxynicotinic acid, 4-pyridoxic acid, 2,6-dimethoxynicotinic acid, citrazinic acid, 6-methyl-2,3-pyridinedicarboxylic acid, methyl-2-pyridylacetate, ethyl 2-pyridylacetate, 3-acetoxypyridine, methyl 6-methylnicotinate, ethyl 2-methylpicolinate, ethyl 3-pyridylacetate, 3,4-pyridinedicarboxamide, 3,4-pyridinedicarboximide, methyl 3-pyridylcarbamate, 1-(3-pyridylmethyl)urea, 1,3-bis(3-pyridylmethyl)-2-thiourea, trans-4-cotininecarboxylic acid, 3-(3-pyridylmethylamino)-propionitrile, 3,4-pyridinedicarbonitrile, 2-chloro-6-methyl-3-pyridinecarbonitrile, 3-cyano-4,6-dimethyl-2-hydroxypyridine, 2,6-dihydroxy-4-methyl-3-pyridinecarbonitrile, 2,3,5,6-tetrafluoro-4-pyridinecarbonitrile, 2,4,6-collidine, pyrazine, 2,3-pyrazinedicarbonitrile, pyrazinecarbonitrile, 2,6-dichloropyrazine, pyrazinecarboxylic, methyl pyrazinecarboxylate, ethyl pyrazinecarboxylate, propyl pyrazinecarboxylate, butyl pyrazinecarboxylate, 2,3-dimethylpyrazine, 2,5-dimethylpyrazine, 2,6-dimethylpyrazine, 2,3-di-2-pyridylpyrazine, 2-methylpyrazine, ethylpyrazine, 2,6-dimethylpyrazine, 2,5-dimethylpyrazine, 2,3-dimethylpyrazine, 2-ethyl-3-methylpyrazine, 2,3-diethylpyrazine, 2-methyl-3-propylpyrazine, 5,6,7,8-tetrahydroquinoxaline, 2,3,5-trimethylpyrazine, 2,3-diethyl-5-methylpyrazine, tetramethylpyrazine, chloropyrazine, 2-methoxypyrazine, 2-methoxy-3-methylpyrazine, 2-ethyl-3-methoxypyrazine, 2-isopropyl-3-methoxypyrazine, 2-sec-butyl-3-methoxypyrazine, 2-isobutyl-3-methoxypyrazine, 2-methyl-6-propoxypyrazine, 3-chloro-2,5-dimethylpyrazine, acetylpyrazine, 2-pyrazinecarboxylic acid, 5-methyl-2-pyrazinecarboxylic acid, 2,3-pyrazinedicarboxylic acid, pyrazinamide, 2,3-pyrazinedicarboxamide, 2,3-bis(2-pyridyl)pyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinol, 2-chloropyrimidine, 5-bromopyrimidine, 2,4,6-trichloropyrimidine, 2,4,5,6-tetrachloropyrimidine, 2,4-dichloro-6-methylpyrimidine, 2,4-dichloro-6-methylpyrimidine, 6-chloro-2,4-dimethoxypyrimidine, 2-hydroxypyrimidine, 4,6-dimethyl-2-hydroxypyrimidine, 2,4-dimethyl-6-hydroxypyrimidine, 4,6-dimethyl-2-hydroxypyrimidine, 2-isopropyl-6-methyl-4-pyrimidinol, 4,6-dihydroxypyrimidine, 2,4-dihydroxy-5,6-dimethylpyrimidine, 2,4-dihydroxy-6-methylpyrimidine, 4,6-dihydroxy-2-methylpyrimidine, 2,4,5-trihydroxypyrimidine, 4,6-dichloro-5-nitropyrimidine, 4,6-dihydroxy-5-nitropyrimidine, 2,4-dihydroxypyrimidine-5-carboxylic acid, 1,3,5-triazine, 2-chloro-4,6-dimethoxy-1,3,5-triazine, 2,4,6-triphenoxy-1,3,5-triazine, 2,4,6-triphenyl-1,3,5-triazine, 2,4,6-tri(2-pyridyl)-1,3,5-triazine, (−)-cotinine (1-methyl-5-(3-pyridyl)-2-pyrrolidinone), quinoline, 2,2'-biquinoline, quinaldine, lepidine, 6-methylquinoline, 7-methylquinoline, 8-methylquinoline, 2,4-dimethylquinoline, 2,6-dimethylquinoline, 2,7-dimethylquinoline, 2,8-dimethylquinoline, 2-phenylquinoline, 7,8-benzoquinoline, 2-chloroquinoline, alpha,alpha,alpha-tribromoquinaldine, 4-chloroquinoline, 6-chloroquinoline, 4-chloro-7-(trifluoromethyl)quinoline, 4-chloro-8-(trifluoromethyl)quinoline, 4-chloro-2,8-bis (trifluoromethyl)quinoline, 4-chloroquinaldine, 7-chloroquinaldine, 2-chlorolepidine, 3-bromoquinoline, 4,7-dichloroquinoline, 4-bromo-2,8-bis(trifluoromethyl)quinoline, 6-methoxyquinoline, 6-methoxyquinaldine, 2-hydroxy-4-methylquinoline, 4-hydroxyquinoline, 7-chloro-4-hydroxyquinoline, 8-(trifluoromethyl)-4-quinolinol, 2,4-quinolinediol, 2-hydroxyquinoline, 5-hydroxyquinoline, 6-hydroxyquinoline, 8-hydroxyquinoline, 8-hydroxyquinaldine, 4-hydroxy-2-methylquinoline, 7-(trifluoromethyl)-4-quinolinol, 2,8-bis(trifluoromethyl)-4-quinolinol, 5-chloro-8-hydroxyquinoline, 5,7-dichloro-8-hydroxyquinoline, 5,7-dibromo-8-hydroxyquinoline, 5,7-dibromo-2-methyl-8-quinolinol, 5,7-dichloro-2-methyl-8-quinolinol, 5-nitroquinoline, 6-nitroquinoline, 8-nitroquinoline, 8-nitroquinaldine, 8-methyl-5-nitroquinoline, 8-hydroxy-5-nitroquinoline, 6-methoxy-8-nitroquinoline, quinaldic acid, 3-quinolinecarboxylic acid, 4-quinolinecarboxylic acid, 8-quinolinecarboxylic acid, 1,2,3,4-tetrahydro-9-acridinecarboxylic acid, 4-methoxy-2-quinolinecarboxylic acid, 4-hydroxyquinoline-2-carboxylic acid, 4-hydroxy-7-trifluoromethyl-3-quinolinecarboxylic acid, 4,8-dihydroxyquinoline-2-carboxylic acid, 2-phenyl-4-quinolinecarboxylic acid, ethyl 4-hydroxy-7-trifluoromethyl-3-quinolinecarboxylate, methyl 2-phenyl-4-quinolinecarboxylate, 2-quinolinecarbonitrile, 3-quinolinecarbonitrile, 2,8-bis(trifluoromethyl)-4-quinolinecarbonitrile, 5,6,7,8-tetrahydroisoquinoline, 3-methyl-5,6,7,8-tetrahydroquinoline, 1,2,3,4,5,6,7,8-octahydroacridine, acridine, 5-triazolo(4,3-A)quinoline, 6,9-dichloro-2-methoxyacridine, 9-hydroxy-4-methoxyacridine, 9-acridinecarboxylic acid, 4,9-acridinedicarboxylic acid, 1,3-dihydroxy-9-acridinecarboxylic acid, phenyl 9-acridinecarboxylate, isoquinoline, 3-methylisoquinoline, 4-bromoisoquinoline, 1,3-dichloroisoquinoline, papaverine, isocarbostyril, 3-hydroxyisoquinoline, 5-hydroxyisoquinoline, 1,5-isoquinolinediol, 5-nitroisoquinoline, 1-isoquinolinyl phenyl ketone, protopapaverine, 1-isoquinolinecarboxylic acid, 3-isoquinolinecarboxylic acid, methyl 3-isoquinolinecarboxylate, 1-isoquinolinecarbonitrile, 3-isoquinolinecarbonitrile, benz[g]isoquinoline-5,10-dione, 3,8-dinitro-6-phenylphenanthridine, cinnoline, phenanthridine, 3,8-diamino-6-phenylphenanthridine, benzo[c]cinnoline, cinnoline-4-carboxylic acid, phthalazine, 1,4-dichlorophthalazine, 1(2H)-phthalazinone, quinazoline, 4-hydroxyquinazoline, 2-methyl-4(3H)-quinazolinone, quinoxaline, 2-methylquinoxaline, 5-methylquinoxaline, 2,3-dimethylquinoxaline, ethyl 2-quinoxalinecarboxylate, 2,3-diphenylquinoxaline, 6,7-dimethyl-2,3-di-(2-pyridyl)quinoxaline, phenazine, 2,3-dichloroquinoxaline, 2,3,6,7-tetrachloroquinoxaline, 2,3-bis(bromomethyl)-quinoxaline, 2-quinoxalinol, 3-methyl-2-quinoxalinol, 2,3-dihydroxyquinoxaline, 2-quinoxalinecarboxylic acid, 3-hydroxy-2-quinoxalinecarboxylic acid, 4-hydroxy-7-methyl-1,8-naphthyridine-3-carboxylic acid, 2,2'-pyridyl, 2,2'-dipyridyl, 4,4'-dimethyl-2,2'-dipyridyl, 4,4'-diphenyl-2,2'dipyridyl, 6-chloro-2,2'-bipyridine, 2,4'-dipyridyl, 4,4'-dipyridyl, di-2-pyridyl ketone, 2,2':6',2"-terpyridine, 1,7-phenanthroline, 1,10-phenanthroline, 4,7-phenanthroline, phenazine, 4-methyl-1,10-phenanthroline, 5-methyl-1,10-phenanthroline, neocuproine, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,9-dimethyl-4,7-diphenyl-1,10-phenanthroline, 5-chloro-1,10-phenanthroline, 6,7-dihydro-5,8-dimethyldibenzo-(1-10)-phenanthroline, 5-nitro-1,10-phenylanthroline, 7-oxo-7-H-benzo[e]perimidine-4-carboxylic acid, lumazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-phenylpyrazole, 3-methyl-1-phenylpyrazole, 3-methyl-1-phenyl-2-pyrazolin-5-one, 4-benzoyl-3-methyl-1-phenyl-2-pyrazolin-5-one, 4-(3-methyl-5-oxo-2-pyrazolin-1-yl)-benzoic acid, 3,5-dimethylpyrazole-1-carboxamide, 1-nitropyrazole, oxazole, 2,5-diphenyloxazole, 2,4,5-trimethyloxazole, 1,4-bis(5-phenyloxazol-2-yl)-benzene, 1,4-bis(4-methyl-5-phenyloxazol-2-yl)benzene, 5-phenyl-2-(4-pyridyl)-oxazole, 2-(4-biphenylyl)-5-phenyloxazole, 2,5-bis(4-biphenylyl)oxazole, 2-methyl-4,5-diphenyloxazole, 9,10-dihydro-2-methyl-4H-benzo(5,6)cyclohept(1,2)-oxazol-4-ol, N1-(4,5-dimethyloxazol-2-yl)-sulfanilamide, 2,5-diphenyl-1,3,4-oxadiazole, 2-(4-biphenylyl)-5-phenyl-1,3,4-oxadiazole, 2-(4-biphenylyl)-5-(4-tert-butylphenyl)-1,3,4-oxadiazole, 2,5-bis(4-aminophenyl)-1,3,4-oxadiazole, 2,5-bis(4-diethylaminophenyl)-1,3,4-oxadiazole, benzoxazole, 2-methylbenzoxazole, 2,5-dimethylbenzoxazole, 2-methyl-5-phenylbenzoxazole, 2-(4-biphenylyl)-6-phenylbenzoxazole, 2-chlorobenzoxazole, 2-phenylbenzoxazole, 2-(2'-hydroxyphenyl)-benzoxazole, 2,4,4-trimethyl-2-oxazoline, isoxazole, 1,2-benzisoxazole, 3,5-dimethylisoxazole, 5-methylisoxazole, 3,5-dimethylisoxazole, 4-(chloromethyl)-3,5-dimethylisoxazole, 3,5-dimethyl-4-nitroisoxazole, 5-methyl-3-phenylisoxazole-4-carboxylic acid, N,5-dimethyl-3-phenylisoxazole-4-carboxamide, N,5-dimethyl-3-(4-fluorophenyl)-4-isoxazolecarboxamide, 2,5-diphenyloxazole, 2,6-bis[(4S)-isopropyl-2-oxazolin-2-yl]pyridine, 1,5-pentamethylenetetrazole, 1,2-dimethylimidazole, 1-methylimidazole, 1-ethylimidazole, 1-propylimidazole, 1-butylimidazole, 1-phenylimidazole, 1-benzylimidazole, 1-benzyl-2-(2,3,4,6-tetrafluorophenyl)-imidazole, 1-(2-chloroethyl)-2-methyl-5-nitroimidazole, metronidazole, 2-methyl-4-nitro-1-imidazolepropionic acid, 2-methyl-4-nitro-1-imidazolepropionitrile, 1,5-dicyclohexylimidazole, 5-chloro-1-methylimidazole, 5-chloro-1-ethyl-2-methylimidazole, 4-(imidazol-1-yl)phenol, imidazo(1,2-A)pyridine, anthranil, 2,3,3-trimethylindolenine, caffeine and 6-chloropurine riboside.

* * * * *